United States Patent [19]

McCall

[11] 4,179,510

[45] Dec. 18, 1979

[54] METHODS OF TREATING PSYCHOSIS

[75] Inventor: John M. McCall, Kalamazoo, Mich.

[73] Assignee: The Upjohn Company, Kalamazoo, Mich.

[21] Appl. No.: 847,371

[22] Filed: Oct. 31, 1977

[51] Int. Cl.$^2$ .................. A61U 31/40; A61U 31/44; A61U 31/445; A61U 31/495

[52] U.S. Cl. .................. 424/267; 424/248.4; 424/248.57; 424/250; 424/263; 424/274; 424/282

[58] Field of Search .................. 424/250, 267, 248.4, 424/248.57, 263, 282, 274

[56] References Cited

U.S. PATENT DOCUMENTS 3,467,675  9/1969  Petersen et al. .................. 424/285

*Primary Examiner*—Stanley J. Friedman
*Attorney, Agent, or Firm*—Sidney B. Williams, Jr.

[57] ABSTRACT

Isochromans, isothiochromans, 2-benzoxepins and 2-benzothiepins are described. The compounds possess hypotensive and antipsychotic properties; methods and compositions using them are described.

16 Claims, No Drawings

METHODS OF TREATING PSYCHOSIS

BACKGROUND OF THE INVENTION

1. Field of the Invention

This invention concerns novel isochromans, isothiochromans, 2-benzoxepins and 2-benzothiepins, methods for preparing them, and their use as hypotensive agents and antipsychotic agents.

The compounds additionally have other effects on the central nervous system, such as antidepressant, antianxiety effects, and can also be used for such indications.

2. The Prior Art

1-Substituted isochromans are known for a variety of uses. For example, U.S. Pat. No. 3,467,675, Sept. 16, 1969 (Petersen), teaches isochromans which are disclosed to treat physiological-psychological abnormalities. Specifically, Petersen teaches the use of the compounds for treatment of endogenic depression. Japanese Pat. No. J5 1125-287, Nov. 1, 1976 (Takeda I) (Derwent 94938X) and Netherlands Pat. No. 7605-36, July 5, 1977 (Takeda) (Derwent 50610Y) also teach isochromans. The Takeda compounds are disclosed to be useful as anti-depression agents, analgesics, diuretics, anti-inflammatory agents, hypotensives and for the treatment of bronchial asthma.

SUMMARY OF THE INVENTION

The invention comprises compounds of the formula:

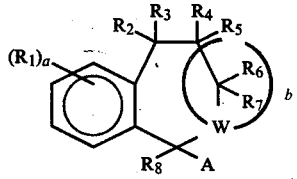

wherein $R_1$ is the same or different and is selected from the group consisting of alkyl of one through three carbons, alkoxy of one through three carbons, trihaloalkyl of one or two carbons, hydroxy, halo, trihaloalkoxy of one or two carbons and o-methylenedioxy with the proviso that at least one $R_1$ is hydroxy, alkoxy or o-methylenedioxy;

a is one through three;

b is zero or one;

$R_2$ through $R_7$ are the same or different and are selected from the group consisting of hydrogen, alkyl of one through three carbons, inclusive, hydroxy, alkoxy of one through three carbons; phenyl; halo; cycloalky of three through six carbons when $R_2$ and $R_3$, $R_4$ and $R_5$, or $R_6$ and $R_7$ are taken together with the carbon to which they are attached; cycloalkyl of four through seven carbons when $R_2$ and $R_4$ or $R_4$ and $R_6$ are taken together with the carbons to which they are attached; and cycloalky of five or six carbons, with the overall provisos that no more than one ring may be attached to any one carbon and that at least two of $R_2$ through $R_7$ are hydrogen.

$R_8$ is alkyl of one through three carbons, hydrogen, or phenyl unsubstituted or substituted with a maximum of three substituents selected from the group consisting of alkyl of one through three carbons, halo, alkoxy of one through three carbons, and trihaloalkyl of one or two carbons, W is oxygen or sulfur;

and A is selected from the group consisting of (i) —$(CH_2)_n NR_9 R_{10}$, wherein n is one to five with the proviso that when be is zero, and n is one or two, $R_2$ through $R_5$ cannot all be hydrogen at the same time.

(ii) —$(CH_2)_m$—$(OCH_2CH_2)_q$—$NR_{21}R_{22}$, wherein m and q are each one to three, and $R_{21}$ and $R_{22}$ can be same or different and are selected from the group consisting of H, alkyl of one through four carbons, and together with the N to which they are attached form heterocyclic rings of four to six ring atoms, morpholine, and $NR_9R_{10}$, (iii) —$(CH_2)_m$—$(OCH_2CH_2)_q$—OH wherein m and q are each one to three

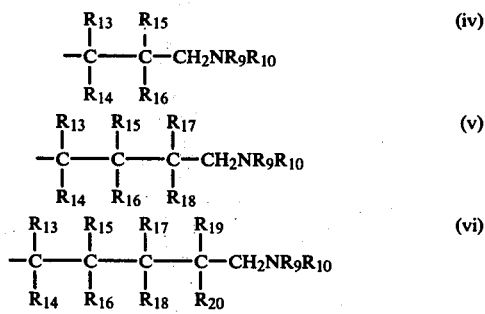

Wherein $NR_9R_{10}$ is a heterocyclic amine selected from the group consisting of

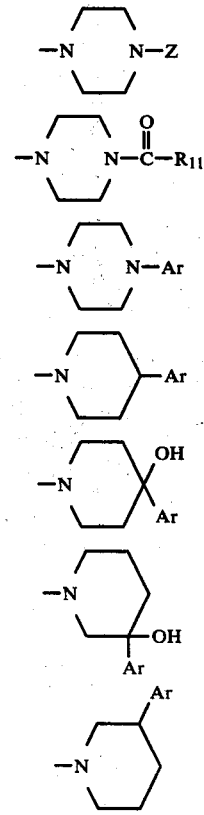

-continued

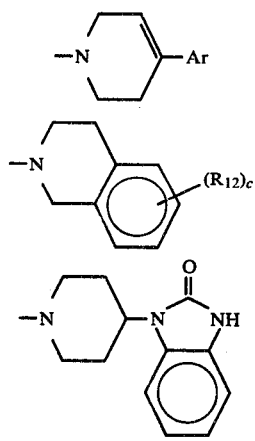

and
—NHCH$_2$CH$_2$AR' wherein R$_{11}$ is alkyl of one through four carbons, 2-furyl, Ar, or alkoxy of one to three carbon atoms;

Z is selected from the group consisting of pyridyl, pyrimidinyl, triazinyl, pyrazinyl, pyridazinyl, pyrrolyl, imidazolyl, pyrazolyl, furyl, tetrazyl, oxazolyl, quinoxalinyl, and quinazolinyl, wherein each member of the group can be unsubstituted or substituted with one or two substituents selected from the group consisting of alkyl of one through three carbons, inclusive, alkoxy of one through three carbons, inclusive, hydroxy, halo, and haloalkyl of one through three carbons, inclusive:

R$_{12}$ is alkyl or alkoxy of one through three carbons, hydroxy, halo, trihalomethyl, R$_{13}$ through R$_{20}$ may be the same or different and are selected from the group hydrogen and alkyl of from one to two carbon atoms, inclusive:

c is zero through two;

Ar and Ar' are phenyl unsubstituted or substituted with one through three substituents selected from the group consisting of alkyl or alkoxy of one through three carbons, inclusive, hydroxy, halo, and trihaloalkyl or trihaloalkoxy of one to two carbons, inclusive.

The preferred compounds of the invention are those having the formula

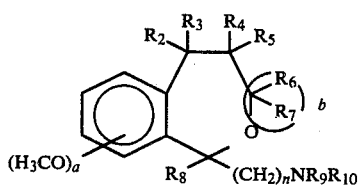

I' wherein b is zero or one,
a is two or three,
n is one to three

R$_2$ through R$_7$ are the same or different and are selected from the group consisting of hydrogen, alkyl of one through three carbons, and cycloalkyl of four through seven carbons when R$_2$ and R$_4$ or R$_4$ and R$_6$ are taken together with the carbons to which they are attached; and NR$_9$R$_{10}$ is selected from the group consisting of

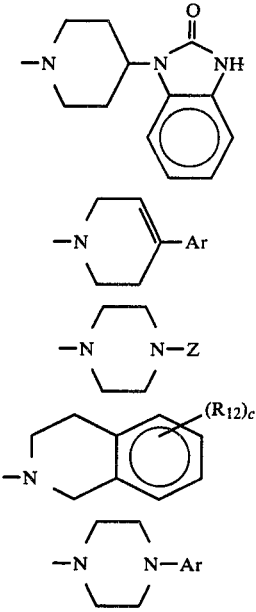

and —NHCH$_2$CH$_2$Ar' wherein Ar, Ar', R$_8$, R$_{12}$, Z and c are the same as defined above.

Specifically preferred are those compounds of formula I' wherein R$_2$ and R$_3$ are both alkyl of from one to three carbon atoms, inclusive, b is zero and R$_8$ is hydrogen.

The invention also comprises the pharmacologically acceptable acid addition salts of the formula I compounds. These include but are not limited to: hydrochlorides, hydrobromides, sulfates, phosphates, acetates, salicylates, pamoates and cyclohexanesulfamates.

The compounds or their acid addition salts in their crystalline state can be isolated as solvates, i.e., with a discreet quantity of solvent, e.g. water, ethanol, associated physically and thus removable without effective alteration of the chemical entity per se.

As used herein, the terms
alkyl (1-3 carbon atoms) refers to methyl, ethyl, propyl, isopropyl, trihaloalkyl of 1-2 carbons is for example trifluoromethyl, trichloromethyl, 2,2,2-trifluoroethyl, alkoxy of 1-3 carbon atoms is for example methoxy, ethoxy, propoxy and isopropoxy, halo refers to chloro, bromo, fluoro, cycloalkyl of 3 through 7 carbons is for example cyclopropyl, cyclopentyl, cyclohexyl, cycloheptyl, trihaloalkoxy of 1 to 2 carbons such as 2,2,2-trifluoromethoxy, trichloromethoxy, trifluoromethoxy, R$_1$ is o-methylenedioxy means that R$_1$ taken together with an adjacent carbon atom is the group $$\begin{array}{c} \text{CH}_2 \\ \diagup \quad \diagdown \\ \text{O} \qquad \text{O} \end{array}$$

There can be no more than one o-methylenedioxy on the free positions on the ring.

The description of this invention is not intended to be limiting for specific optically active isomers. All possible isomeric forms of the compounds are included.

The invention also comprises the use of compounds of formula I to reduce blood pressure in mammals, including man. The compounds wherein $R_2$ and $R_3$ are both lower alkyl are particularly effective for reducing blood pressure.

The invention also comprises the use of compound of formula I as antipsychotic agents.

The invention also comprises pharmaceutical dosage unit forms adapted for systemic administration to obtain antihypertensive and antipsychotic effects in mammals, including man, comprising an effective amount of a compound according to formulas I and Ia, or pharmaceutically acceptable acid addition salts thereof, in combination with pharmaceutical carriers which adapt such compounds for systemic administration.

The invention also comprises the preparation of compounds of formula I.

The compounds of formula I are also analgesic and antidepressant agents.

The compounds may be administered in conventional forms such as tablets or capsules, including the sustained oral release type, powders, elixirs, syrups, suppositories, and intramuscular or intravenous injections.

DETAILED DESCRIPTION OF THE INVENTION

The compounds of formula I wherein A is $-(CH_2)_n NR_9 R_{10}$ can be prepared according to the following schematic flow chart

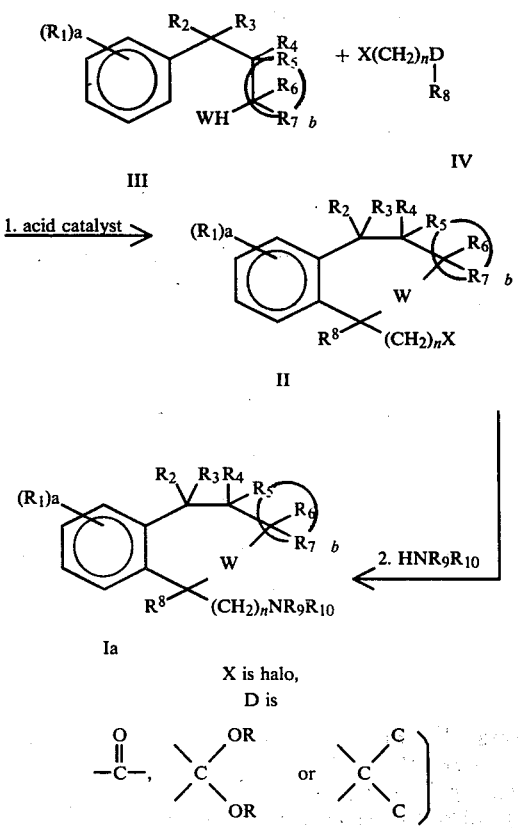

X is halo,
D is

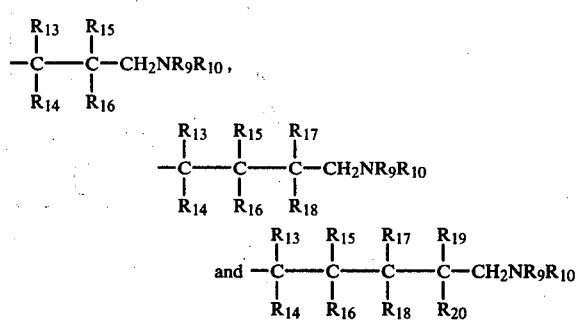

where R is alkyl of one through two carbons, i.e. ketal or acetal functionality, and all the other terms are as defined above. When n is 1 in a compound of formula I, it is preferred that X in structure II be bromo. When n is 2 to 5, it is preferred that X be chloro.

The compounds of formula I wherein A is selected from group consisting of

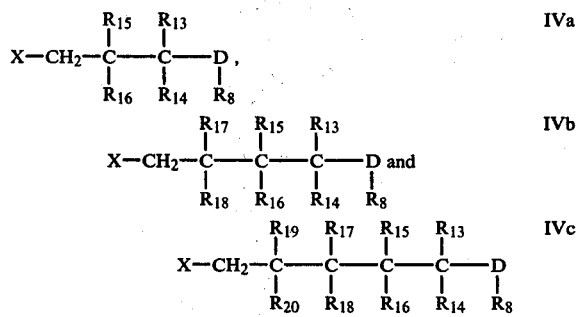

can also be prepared in accordance with the above flow chart by substituting $$X-CH_2-\underset{\underset{R_{16}}{|}}{\overset{\overset{R_{15}}{|}}{C}}-\underset{\underset{R_{14}}{|}}{\overset{\overset{R_{13}}{|}}{C}}-\underset{\underset{R_8}{|}}{\overset{}{D}} , \qquad IVa$$

$$X-CH_2-\underset{\underset{R_{18}}{|}}{\overset{\overset{R_{17}}{|}}{C}}-\underset{\underset{R_{16}}{|}}{\overset{\overset{R_{15}}{|}}{C}}-\underset{\underset{R_{14}}{|}}{\overset{\overset{R_{13}}{|}}{C}}-\underset{\underset{R_8}{|}}{\overset{}{D}} \text{ and} \qquad IVb$$

$$X-CH_2-\underset{\underset{R_{20}}{|}}{\overset{\overset{R_{19}}{|}}{C}}-\underset{\underset{R_{18}}{|}}{\overset{\overset{R_{17}}{|}}{C}}-\underset{\underset{R_{16}}{|}}{\overset{\overset{R_{15}}{|}}{C}}-\underset{\underset{R_{14}}{|}}{\overset{\overset{R_{13}}{|}}{C}}-\underset{\underset{R_8}{|}}{\overset{}{D}} \qquad IVc$$

wherein D, X, $R_8$ and $R_{13}$ through $R_{20}$ are the same as above, respectively, for the straight chain compounds of formula IV.

Step 1 can be performed in the absence of solvent but a solvent such as methylene chloride, nitromethane tetrahydrofuran (THF), ethylether, carbon disulfide, benzene, or toluene is preferred. Preferred temperature is about 25° but temperatures from 0° to 60° are acceptable.

Step 2 can be performed in the absence of solvent but use of a solvent such as methyl, ethyl, propyl, or butyl alcohol, ethylene glycol, dimethylformamide (DMF), or dimethylsulfoxide (DMSO) is preferred. An excess amount of base such as triethylamine is used in step 2 to absorb the acid produced.

The acid catalysts for step 1 include mineral acids and Lewis acids such as HCl, HBr and $H_2SO_4$, $BF_3.Et_2O$, p-toluenesulfonic acid (pTsOH), trifluoroacetic acid (TFA), acetic acid, and $SnCl_4$.

The compounds (I) obtained can be recovered and purified by conventional methods, for example, extraction, chromatography, crystallization, and combinations thereof.

The following is a preferred preparation for the 2-benzoxepines of formula I where n=2.

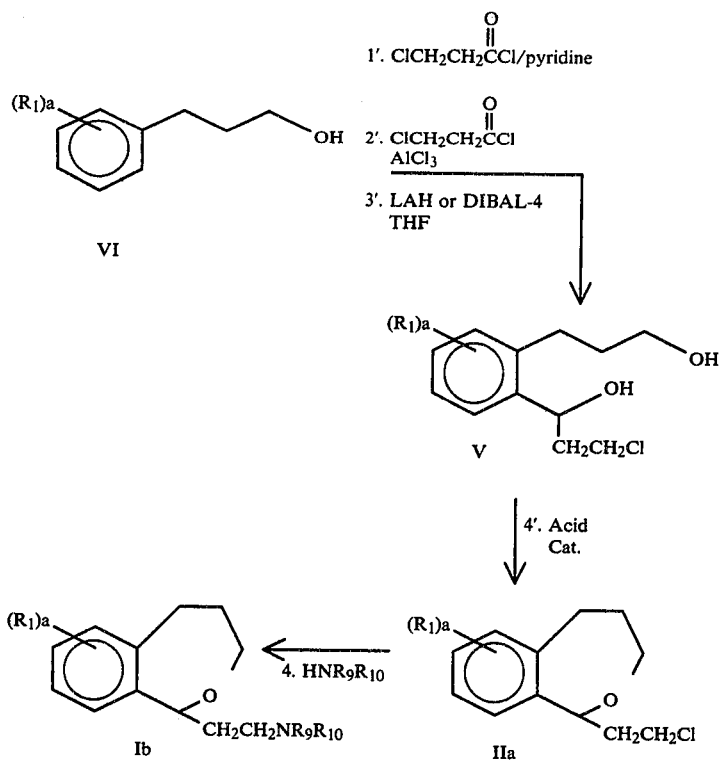

Step 1' is carried out in the presence of an acid scavenger, for example, pyridine, and is a conventional acylation reaction.

Step 2' is performed in an aromatic solvent such as toluene, in nitromethane or in a halocarbon such as methylene chloride. Other catalysts such as $SnCl_4$ or $FeCl_3$ are usable but $AlCl_3$ is preferred. Temperature can range from 10° to 100°.

Step 3' may be conducted in non-polar solvents such as THF, ether, or toluene.

The acid catalysts for step 4' are as described above for producing the compounds of structure II.

The compounds (II) obtained can be recovered and purified by conventional methods, for example, extraction, chromatography and crystallization.

The thiols of structure III (W=S) can be prepared from the alcohols via their bromides in accordance with the following flow chart, or by other literature methods for example, see Frank and Smith, J. Amer. Chem. Soc., 68, 2103 (1946).

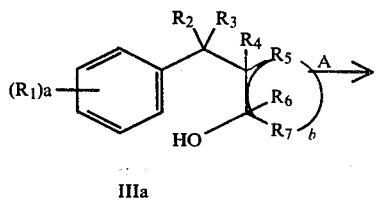

IIIa

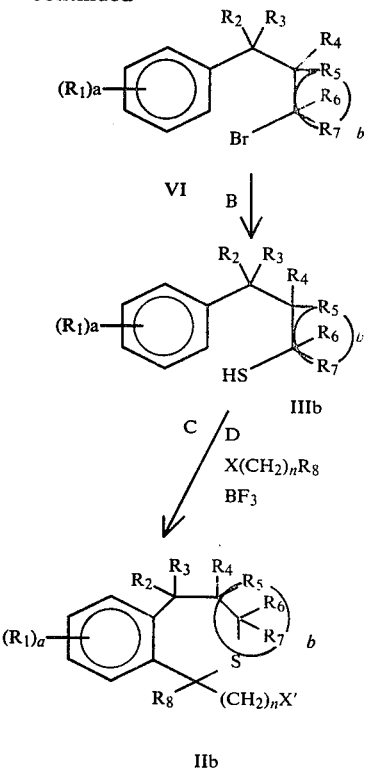

wherein n is 1 to 5 and a, b, $R_1$ through $R_8$ and D are as above, and X' is chloro or bromo. The compounds wherein A is the branched alkylene chain can be made using the appropriate starting materials IVa, IVb, and IVc.

In step A, the alcohol of formula IIIa can be converted to the bromide of formula VI by various procedures known to those skilled in the art. For example, it may be reacted with phosphorus tribromide or hydrogen bromide as is described in J. March, "Advanced Organic Chemistry", McGraw-Hill, 1968, p. 343.

In step B the bromide of formula Q is reacted with a mercaptide, for example sodium mercaptide, to give the thiol of formula IIIb.

In step C the thiol of formula IIIb is reacted with the appropriate acetal, ketal, ketone, or aldehyde in the presence of an acid catalyst to give the halide of formula IIb.

The halide IIb can be reacted with amines to form the compounds having the formula I'b in the manner described above for the preparation of compounds of Formula I.

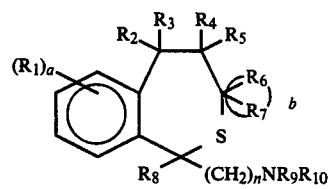

Similarly, by using the thiol IIIb with starting materials IVa, IVb or IVc followed by reaction with the desired amines there are obtained the appropriate 1-substituted 2-benzothiepins.

The compounds of structure III wherein at least one of $R_2$ through $R_7$ is other than hydrogen can be obtained by conventional chemical reactions, for example:

For the preparation of compounds of formula I wherein $R_2$ through $R_7$ are alkyl, halo, alkoxy cycloalkyl and b=0, the following reactions (1-4) can be followed as examples:

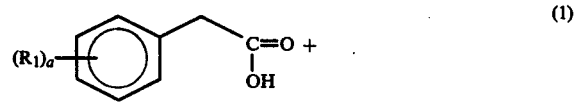

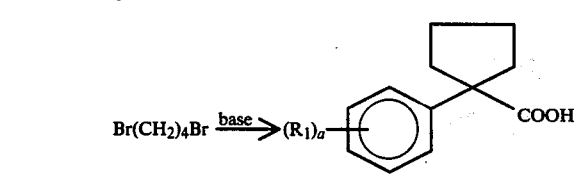

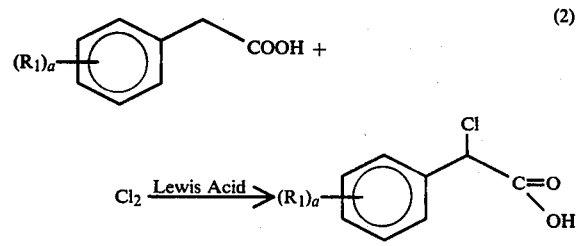

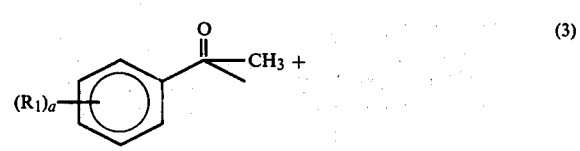

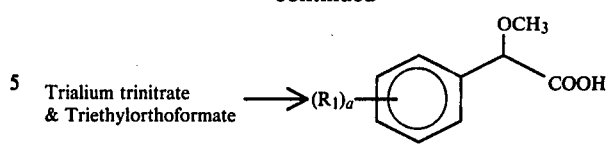

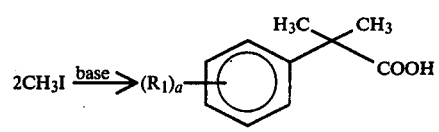

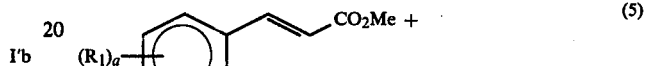

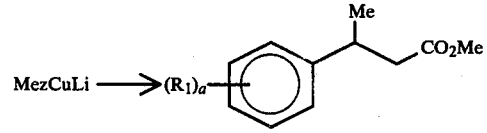

Each acid or ester can then be reduced by conventional procedures (e.g. with sodium borohydride-Ethanol) to the alcohol and subsequently treated with compounds IV, IVa, IVb or IVc to give the precursor 1-(haloalkyl)-1-$R_8$ isochromans or benzoxepins which can then be reacted as described above with amines to give the corresponding formula I compounds. When it is desired that W=S, the thiols can be prepared from the alcohols as shown in the flow scheme for preparing compounds of formula IIb.

The above reactions for placing substituents on the carbon alpha to the acid function in a chain are known in the art and are only given as representative. They are not to be construed as limiting.

Reaction type (I) has been described in Organic Syntheses (Wiley) collective volumes I–IV, and in J. March, Advanced Organic Chemistry, McGraw-Hill, (1968) p. 360. Reaction type (2) is also in Organic Syntheses and in J. March, p. 460 (it is known as the Hell-Volhard-Zelinskii reaction).

Reaction type (3) has been described in J. Amer. Chem. Soc., 98, 6750 (1976).

Reaction type (4) is known in the art for alkylation at acidic hydrogens sites—this type of reaction can be found in Organic Syntheses (Wiley), Volume 50, p. 58 (1970).

Reaction type (5) can be carried out according to Katzenellenbogen, J. Org. Chem. 38, 2733(1973).

Compounds of formula I wherein A contains oxygen can be prepared in accordance with the following flow diagram:

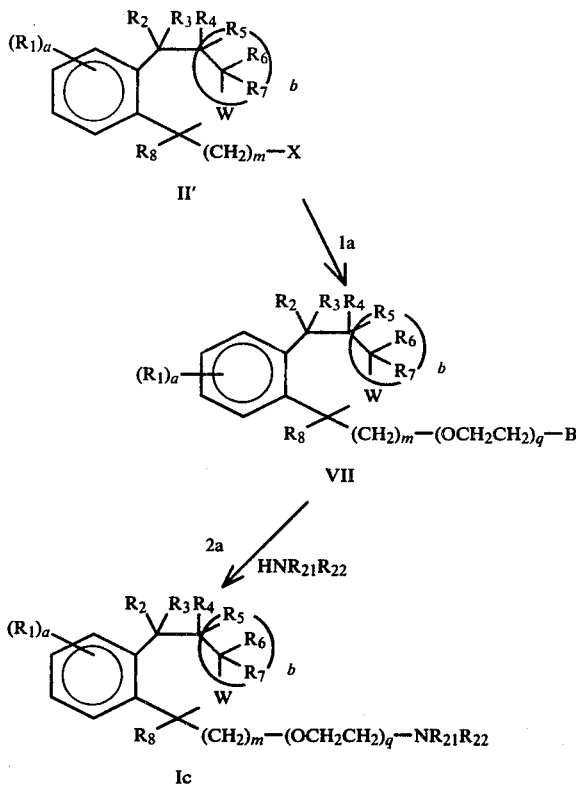

wherein a, b, R₁ through R₈ and NR₂₁R₂₂ are the same as above, m and q are each one to three and B' is selected from the group consisting of hydroxy, halo and the group

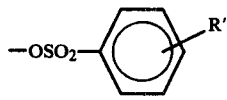

wherein R' is selected from the group consisting of hydrogen, lower alkyl of from one to three carbon atoms, NO₂, halo and trifluoromethyl.

The reaction of step 2a is preferably carried out with VII wherein B' is halo, (preferred is chlorine) p-nitrobenzenesulfonyl, or other leaving group. When B' is hydroxy a prior sulfonation reaction is performed, for example with p-nitrobenzenesulfonyl chloride, to give VII wherein B' is p-nitrobenzenesulfonyl; this compound then can be reacted with the amine as described below:

When B' is the group

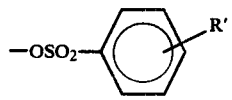

wherein R' is the same as above, the reaction of step 2a is conducted by using about 1-10 moles of amine to about 1 mole of the compound of formula VII, preferably two moles of amine to about one mole of the compound of formula VII. The reaction is conducted at a temperature of about 20° to 70° for a period of one to 40 hours.

When B' is halogen, the reaction of step 2a is conducted in the presence or absence of a solvent at a temperature of between 20° and 70° for a period of one to 40 hours. Solvents that can be utilized include, but are not limited to ethylene glycol, dimethyl formamide, (DMF), tetrahydrofuran, dimethyl sulfoxide (DMSO), with DMF being the preferred solvent.

Compounds of formula VII wherein B' is substituted benzenesulfonyl are prepared as follows:

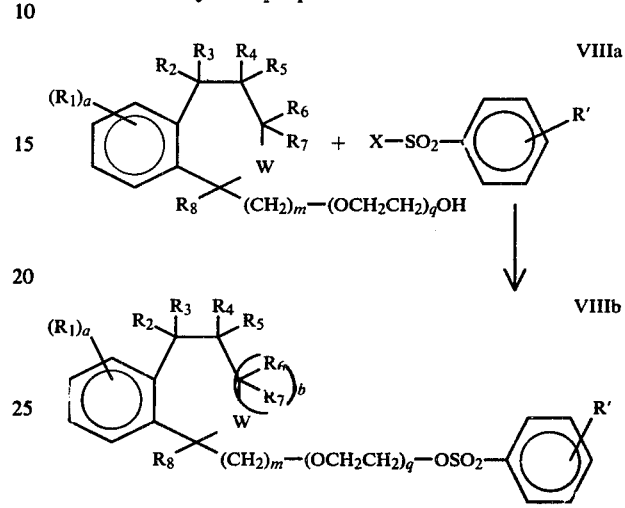

wherein a, b, m, q, W and R₁ through R₈ are the same as above, and R' is as above.

The above reaction may be carried out in the presence or absence of a solvent at a temperature between 20° and 50° for a period of about one hour to ten hours. Solvents that may be used include DMF, THF, methylene chloride and toluene.

The preferred solvent is methylene chloride. Suitable acid acceptors include the trialkylamines, e.g. triethylamine, inorganic salts, e.g. barium carbonate, and DBU. The preferred acid acceptor is triethylamine.

Compounds of formula VII where B' is halo are prepared in accordance with the following schematic flow chart.

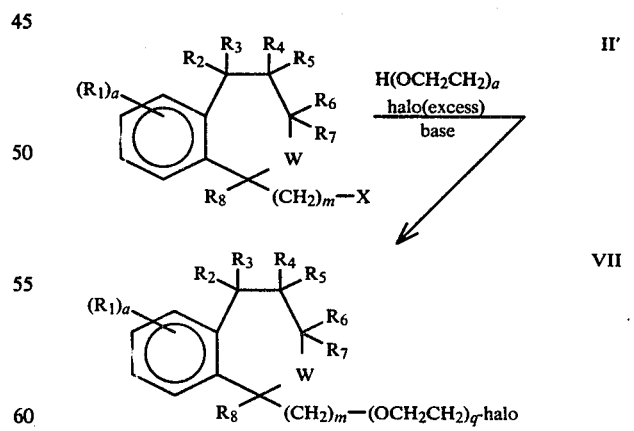

where a, b, m, q, R₁ through R₈ and W are the same as above.

The reaction may be carried out in the absence or presence of a solvent and at a temperature of about 20° to 100° for 20 to 120 hours. Organic or inorganic bases such as barium carbonate, triethylamine or ethyl di-i-propylamine can be used as acid scavengers.

The compounds of formula VIIIa wherein q is two or three may also be prepared from compounds of formula VIIIa wherein q is one in accordance with the following flow diagram The compounds of formula Ic, wherein b is zero, m is 1, and $R_1$–$R_5$, $R_8$, $R_{22}$, $NR_{21}$, a, q, and W are as defined above, are advantageously prepared by the route described in the following chart:

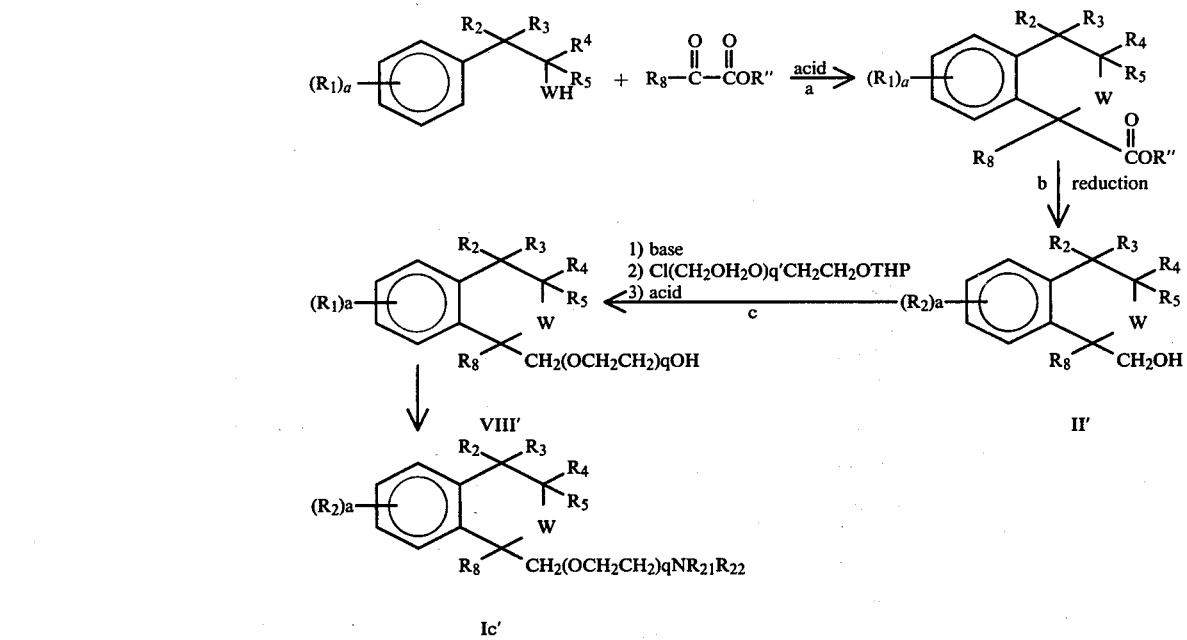

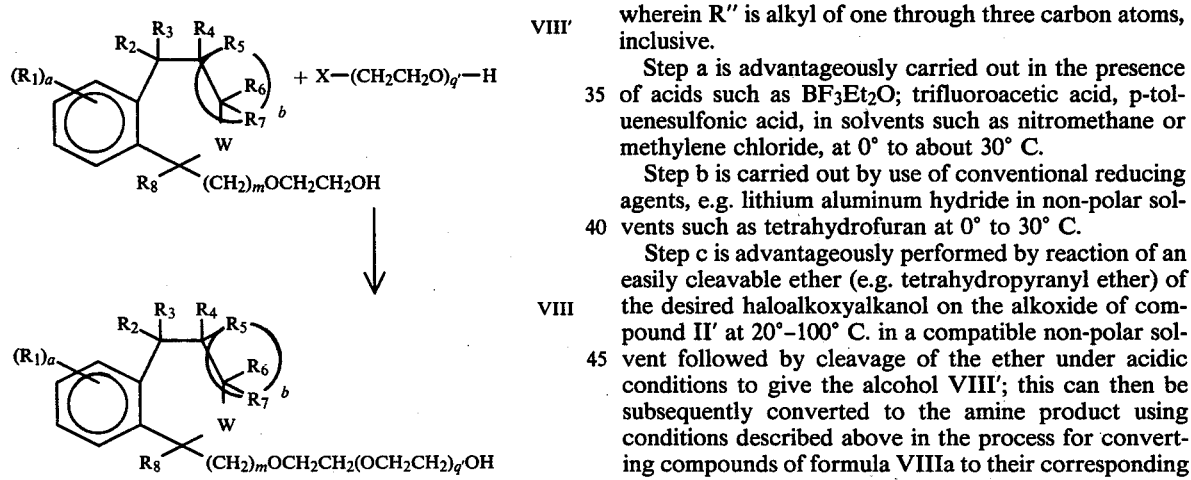

where X is halogen, q' is one or two and a, b, m, W and $R_1$ through $R_8$ are the same as above.

This reaction may be carried out in the absence or presence of a solvent. It is also desirable to use an acid acceptor and to run the reaction for about 20 to 120 hours at a temperature of 20° to 100°. Same acid scavengers as above can be used.

The compounds of formula VII wherein B is hydroxy and q is one are prepared by reacting a compound of formula II' with ethylene glycol. The reaction is conducted in the presence of an acid acceptor such as diisopropylethylamine at a temperature of between 20° and 100° for a period of about 20 to 120 hours.

In all of the procedures described herein, the desired product or intermediates can be obtained from the reaction mixture utilizing standard methods, for example, extraction, chromatography, crystallization and combinations thereof.

wherein R" is alkyl of one through three carbon atoms, inclusive.

Step a is advantageously carried out in the presence of acids such as $BF_3Et_2O$; trifluoroacetic acid, p-toluenesulfonic acid, in solvents such as nitromethane or methylene chloride, at 0° to about 30° C.

Step b is carried out by use of conventional reducing agents, e.g. lithium aluminum hydride in non-polar solvents such as tetrahydrofuran at 0° to 30° C.

Step c is advantageously performed by reaction of an easily cleavable ether (e.g. tetrahydropyranyl ether) of the desired haloalkoxyalkanol on the alkoxide of compound II' at 20°–100° C. in a compatible non-polar solvent followed by cleavage of the ether under acidic conditions to give the alcohol VIII'; this can then be subsequently converted to the amine product using conditions described above in the process for converting compounds of formula VIIIa to their corresponding amines.

Pharmaceutically acceptable acid addition salts of the compounds (I) are prepared by reacting the free base of a compound of formula (I) with a stoichiometric amount of an acid, such as hydrogen chloride, hydrogen bromide, hydrogen iodide, sulfuric acid, phosphoric acid, acetic acid, propionic acid, butyric acid, lactic acid, citric acid, succinic acid, benzoic acid, salicylic acid, pamoic acid, phthalic acid, cyclohexanesulfamic acid, and the like.

This invention relates also to pharmaceutical dosage unit forms for systemic administration (oral and parenteral and rectal administration) for treating hypertensive mammals, including humans. The term "dosage unit form" as used in this specification and in the claims refers to physically discrete units suitable as unitary dosages for mammalian subjects, each unit containing a pre-determined quantity of the essential active ingredient, i.e., a compound (I) or a pharmaceutically acceptable acid addition salt thereof calculated to produce the desired effect, in combination with the required pharmaceutical means which adapt the said ingredient for systemic administration. Examples of dosage unit forms in accordance with this invention are tablets, capsules, orally administered liquid preparations in liquid vehicles, sterile preparations in liquid vehicles for intramuscular and intravenous administration, suppositories, and sterile dry preparations for the extemporaneous preparation of sterile injectable preparations in a liquid vehicle. Solid diluents or carriers for the solid oral pharmaceutical dosage unit forms are selected from the group consisting of lipids, carbohydrates, proteins and mineral solids, for example, starch, sucrose, kaolin, di-calcium phosphate, gelatin, acacia, corn syrup, corn starch, talc and the like. Capsules, both hard and soft, are formulated with conventional diluents and excipients, for example, edible oils, talc, calcium carbonate, calcium stearate and the like. Liquid preparations for oral administration are prepared in water or aqueous vehicles which advantageously contain suspending agents, such as for example, ethanol, sodium carboxymethylcellulose, acacia, polyvinyl pyrrolidone, polyvinyl alcohol and the like. In the instance of injectable forms, they must be sterile and must be fluid to the extent that easy syringeability exists. Such preparations must be stable under the conditions of manufacture and storage, and ordinarily contain in addition to the basic solvent or suspending liquid, preservatives in the nature of bacteristatic and fungicistatis agents, for example, parabens, chlorobutanol, benzyl, alcohol, phenol, thimerosal, and the like. In many cases it is preferable to include isotonic agents, for example sugars or sodium chloride. Carriers and vehicles include vegetable oils, ethanol and polyols, for example, glycerol, propylene glycol, liquid polyethylene glycol, and the like. Any solid preparations for subsequent extemporaneous preparation of sterile injectable preparations are sterilized, preferably by exposure to a sterilizing gas, such as for example ethylene oxide. The aforesaid carriers, vehicles, diluents, excipients, preservatives, isotonic agents and the like constitute the pharmaceutical means which adapt the preparations for systemic administration.

For animals, food premixes with starch, oatmeal, dried fishmeat, fishmeat, fishmeal, flour, and the like can be prepared.

For CNS disease, a daily dose of 5 to 600 mq is indicated, preferentially 10 to 200 mq; in unit of two or three subdivided doses, and the exact amount is adjusted based on the weight, age, and condition of the patient.

The pharmaceutical dosage unit forms are prepared in accordance with the preceding general description to provide from about 0.5 mg to about 100 mg of the essential active ingredient per dosage unit form. The amount of the essential active ingredient provided in the pharmaceutical dosage unit forms is based on the finding that the effective amount of compounds of the invention and acid addition salts thereof, for obtaining a hypotensive effect in mammals is within a range from about 0.1 mg per kg to about 35 mg/kg, preferably 0.3 to 15 mg/kg.

The active ingredients of this invention can also be compounded in combination with other ingredients. The amount of such other active ingredients is to be determined with reference to the usual dosage of each such ingredient. Thus these novel compounds can be combined with other hypotensive agents such as α-methyldopa (100–250 mg); with diuretics such as hydrochlorothiazide (10–50 mg); peripheral vasodilators such as hydralazine (10–100 mg); tranquilizers such as meprobamate (200–400 mg), diazepam (2–10 mg) muscle relaxants, such as carisoprodol (200–400 mg).

The tranquilization activity of the new compounds of formulae I and their pharmacologically acceptable acid addition salts are tested in mice as follows:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, and 5 cm. high), partially embedded in wood shavings, climb out in a very short time, when not treated. Mice remaining in the dish for more than 3 minutes indicates tranquilization. $ED_{50}$ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than one minute.

Nicotine antagonism test: Mice in a group of 6 are injected with the test compound. Thirty minutes later the mice including control (untreated) mice are injected with nicotine salicylate (2 mg./kg.). The control mice show overstimulation, i.e. (1) running convulsions, followed by (2) tonic extensor fits; followed by (3) deaths. Pretreatment with an active sedative or tranquilizing compound protects mice against (2) and (3).

TESTING FOR ANXIETY

Prolongation of Hypoxic survival: Pretreatment of mice exposed to the stress of progressive hypoxia and hyperapnia with anxiolytics results in a prolongation of survival. Male CF-1 derived mice are used in these studies. Thirty minutes after intraperitoneal pretreatment (test agent suspended in 0.25% methylcellulose or vehicle alone, 1 cc/100 gm body weight) the mice are placed singly in 125 ml. Erlenmeyer flasks. The receptacles are tightly stoppered and the survival time (time from stoppering to the last respiratory effort) of each animal noted. Each compound is tested at three or more doses spaced at 0.3 log intervals. Six mice are used per dose with six vehicle injected controls run simultaneously. The mean (15–18 minutes) and standard deviation (1–2 minutes) of the survival time for the vehicle treated mice are used to convert the data to a quantal form in the following manner. All survival times that differed from the mean of the controls by more than 2 standard deviations are scored as a drug effect. $ED_{50}s$ are calculated by the method of Spearman and Karber (Finney, D. J., Statistical Method in Biological Assay, Hafner Publ., Co., N.Y., 1952).

The novel compounds of formula I and pharmacologically acceptable acid addition salts thereof also have antidepressant activity.

The main function of an anti-depressant is to return the depressed individual to normal function. This should be carefully differentiated from psychic stimulants such as the amphetamines which produced overstimulation in the normal individual.

Many different methods have been and are used to evaluate antidepressant activity. In general these methods involve antagonism to a depressant such as reserpine or tetrabenazine or a synergistic increase of the toxicity of certain compounds (i.e., yohimbine or 3,4-dihydroxyphenylalanine) and comparison of the drug action of the new compound with other known antidepressants. No single test alone can determine whether or not a new compound is an antidepressant or not, but the profile evidenced by various tests will establish that antidepressant action is present. A number of such tests are described below.

Hypothermic tests with oxotremorine [1-[4-(pyrrolidinyl)-2-butynyl]-2-pyrrolidinone].

Oxotremorine (as well as apomorphine and tetrabenzine) produces hypothermic responses in mice. This response is blocked by anticholinergics and antidepressants such as atropine and imipramine.

Oxotremorine produced a very pronounced hypothermia which reaches a peak 60 minutes after administration. When administered at 0.6 mg/kg the body temperature of a mouse is decreased about 13° F. (when the mouse is kept at room temperature). This temperature decrease is antagonized by antidepressants, e.g., desipramine, imipramine, and amitriptyline.

The present compounds are tested as follows. Groups of four male mice weighing 18-22 g (Strain CF1, Carworth Farms) are injected intraperitoneally with the test compound prepared in 0.25% methylcellulose and placed in plastic cages. Thirty minutes later 1 mg/kg oxotremorine hydrochloride is injected subcutaneously. The mice are placed in a refrigerator maintained at 19° C. Thirty minutes later the intraperitoneal temperature is measured using a thermistor probe. An increase of 4° F. in the body temperature of the treated mouse (oxotremorine and test compound) over the control mouse (oxotremorine treated only) is indicative of antidepressive activity.

The same compounds were also tested for potentiation of yohimbine aggregation toxicity. The $LD_{50}$ of yohimbine hydrochloride in mice is 45 mg/kg, i.p. Administration of 20 mg/kg. of yohimbine hydrochloride is non-lethal. If an antidepressant is administered prior to the yohimbine hydrochloride (20 mg/kg) the lethality of the yohimbine hydrochloride is increased.

Eight male CF1 mice, 18-22 g, are injected with yohimbine hydrochloride in saline solution. After four hours the $LD_{50}$s are determined. Groups of eight mice are injected with the antidepressant 30 minutes before the administration of yohimbine hydrochloride [YCl] (20 mg/kg). No mice or only one mouse is killed from 20 mg/kg of [YCl]. If [YCl] is administered in the presence of an antidepressant an increase in the toxicity of [YCl] is found. The $ED_{50}$ is the dosage of test compound which causes 50% of the mice to die.

Also the compounds are tested for the potentiation of apomorphine gnawing. A group of 4 mice (male, CF1, 18-22 g) are administered the test compound intraperitoneally 1 hour prior to the subcutaneous injection of apomorphine hydrochloride 10 mg/kg. The mice are then placed in a plastic box (6×11×5 inches) lined at the bottom with a cellophane-backed, absorbent paper. The degree of damage to the paper at the end of 30 minutes is scored from zero to 4. The scores 2 to 4 indicate that the compound is a potentiator of apomorphine in this test.

Results in the above tests show that the compounds of formula I and the pharmacologically acceptable acid addition salts thereof can be used as antidepressants, sedatives, and antianxiety drugs in mammals to achieve normalcy in the depressed or anxious individual.

As antipsychotics-neuroleptics the compounds of formula I and their pharmacologically acceptable acid addition salts can be used in dosages of 1-300 mg/day and preferably 5-250 mg/day in oral or injectable preparations, as described above, to alleviate psychotic states such as schizophrenia, manic depressions, etc. The exact amounts to be given are dependent on the age, weight, and condition of the patient.

The following examples and preparations describe the manner and process of making and using the invention and set forth the best mode contemplated by the inventor of carrying out the invention but are not to be construed as limiting.

All temperatures are in degrees centigrade.

The compounds of this invention show potent hypotensive activity on oral administration to normotensive rats. A 4 mm Hg decrease in Mean Arterial Pressure when measured at 4 hours or 24 hours after administration of 50 mg/kg of drug is considered statistically significant. By far the majority of the compounds of this invention give blood pressure drops of greater than 8 mm Hg, and some of them have the desirable feature of being of longer duration of action (beyond 24 hours).

Also, in the accepted test methodology for neuroleptic (antipsychotic) activity, such as the inhibition of amphetamine aggregation toxicity (Weaver and Kerley, J. Pharm. and Exp. Therap., 135, 240 (1962)) the dose required to inhibit death of 50% of animals previously challenged with amphetamine gives a measure of the activity of the drug; the lower the dose required, the more potent the drug. Mice are injected with the drug subcutaneously. Inhibition at a dose of 25 mg/kg is considered significant. The potent compounds of this invention show a desirable level of death inhibition at a dose of 15 mg/kg or less.

In other accepted tests for antipsychotic activity, as, for example, reversal of hypothermia caused by oxotremorine again the potent compounds of this invention showed reversal at a dose of less than 15 mg/kg; reversal at a dose of 40 mg/kg is considered significant.

HPLC=high performance liquid chromatography.

SSB refers to Skellysolve B ®, an isomeric mixture of hexane.

Preparation 1:
7,8-Dimethoxy-1-bromomethyl-1,3,4,5-tetrahydro-2-benzoxepin

A solution of 5.00 g. of 3-(3,4-dimethoxyphenyl)-1-propanol, 9.76 ml of bromoacetaldehyde diethyl acetal, 2.0 ml of trifluoroacetic acid, and 125 ml of nitromethane is heated at 65° under a nitrogen atmosphere for 2 hours. After cooling, the reaction mixture is extracted with methylene chloride and aqueous sodium bicarbonate. The organic layer is taken to dryness in vacuo and the residue is chromatographed first with 100% $CH_2Cl_2$ and a second time with 10% ethyl acetate: SSB to give 300 g of 7,8-dimethoxy-1-bromomethyl-1,3,4,5-tetrahydro-2-benzoxepin, m.p., 44°-45°.

Following the procedure of Preparation 1, but substituting the appropriate 3-(substituted-phenyl)-1-propanol, for 3-(3,4-dimethoxyphenyl)-1-propanol the 1-bromomethyl-2-benzoxepins of Table 1 can be prepared.

TABLE 1

1. 9-methoxy-8-propyl-1-bromomethyl-1,3,4,5-tetrahydro-2-benzoxepin,
2. 9-methoxy-1-bromomethyl-1,3,4,5-tetrahydro-2-benzoxepin,
3. 6,7-dimethoxy-1-bromomethyl-1,3,4,5-tetrahydro-2-benzoxepin,
4. 7-ethoxy-1-bromomethyl-1,3,4,5-tetrahydro-2-benzoxepin,
5. 7,8,9-trimethoxy-1-bromomethyl-1,3,4,5-tetrahydro-2-benzoxepin,
6. 7-hydroxy-6-methoxy-1-bromomethyl-1,3,4,5-tetrahydro-2-benzoxepin,
7. 8-bromo-7-methoxy-1-bromomethyl-1,3,4,5-tetrahydro-2-benzoxepin,
8. 7-methoxy-8,9-dichloro-1-bromomethyl-1,3,4,5-tetrahydro-2-benzoxepin,
9. 7-methoxy-8-trifluoromethyl-1-bromomethyl-1,3,4,5-tetrahydro-2-benzoxepin,
10. 7,8-methylenedioxy-1-bromomethyl-1,3,4,5-tetrahydro-2-benzoxepin,
11. 7-methoxy-5-methyl-1-bromomethyl-1,3,4,5-tetrahydro-2-benzoxepin,
12. 7,9-dimethoxy-4,5-dimethyl-1-bromomethyl-1,3,4,5-tetrahydro-2-benzoxepin,
13. 7,8,9-trimethoxy-4-methyl-1-bromomethyl-1,3,4,5-tetrahydro-2-benzoxepin,
14. 9-methoxy-4-phenyl-1-bromomethyl-1,3,4,5-tetrahydro-2-benzoxepin,
15. 7-hydroxy-5-bromo-1-bromomethyl-1,3,4,5-tetrahydro-2-benzoxepin,
16. 7,8-dimethoxy-5,5-dimethyl-1-bromomethyl-1,3,4,5-tetrahydro-2-benzoxepin,
17. 7,8-dimethoxy-4,4-dimethyl-1-bromomethyl-1,3,4,5-tetrahydro-2-benzoxepin,
18. -bromomethyl-8,9-dimethoxy-1,3,4,5-tetrahydro-[spiro-4(3H),1'-cyclobutane],
19. 6-bromomethyl-8,9-dipropyloxy-2,3,3a,4,6,10b-hexahydro-1H-benz[c]cyclopent[e]oxepin,
20. 4-cyclopentyl-8,9-dimethoxy-1-bromomethyl-1,3,4,5-tetrahydro-2-benzoxepin,
21. 7,8-dihydroxy-5-propyl-1-bromomethyl-1,3,4,5-tetrahydro-2-benzoxepin,
22. 7,8-dimethoxy-9-trifluoromethyl-1-bromomethyl-1,3,4,5-tetrahydro-2-benzoxepin.

Preparation 1A:
7,8-Dimethoxy-1-chloroethyl-1,3,4,5-tetrahydro-2-benzoxepin To 19.86 g. (0.149 moles) of $AlCl_3$ in 200 ml of $CH_2Cl_2$ was added 14.20 ml (0.149 moles) of 3-chloropropionylchloride. The mixture is stirred for 15 minutes under a $N_2$ atmosphere and then 38.00 g (0.0992 moles) of the 3-chloropropionate of 3-(3,4-dimethoxyphenyl)-propanol in 200 ml of $CH_2Cl_2$ is added over a period of 15 min. from a dropping funnel. After stirring at room temperature for 30 min., the reaction mixture is heated at reflux for an additional 3.6 hours. The reaction mixture is then cooled and aqueous sodium bicarbonate is added until gas evolution ceases. The organic layer is filtered through sodium sulfate and taken to dryness. The residue is chromatographed using 20% EtOAc:-Skellysolve B as eluant.

A tetrahydrofuran solution of 3-chloro-4',5'-dimethoxy-3'-[3-(3-chloropropionoxy)propyl]propiophenone (about 40 g.) is added dropwise to an ice-cooled mixture of 7.3 g. of lithium aluminum hydride in tetrahydrofuran. After stirring for 20 minutes the reaction mixture is treated with 7.3 ml water, 7.3 ml 15% sodium hydroxide, and 21 ml water. The resulting suspension is filtered through Celite and the salts washed with ether. The filtrate is extracted with brine and the organic phase is filtered through sodium sulfate and concentrated.

The crude product is dissolved in 500 ml of methylene chloride and treated with 13 g of p-toluenesulfonic acid monohydrate. After stirring for 10 minutes the blue-green solution is extracted with aqueous sodium bicarbonate and brine. The organic layer is filtered through sodium sulfate and taken to dryness. Chromatography on silica gel with 20% ethyl acetate in Skellysolve B gives 14.7 g of 7,8-dimethoxy-1-chloroethyl-1,3,4,5-tetrahydro-2-benzoxepin.

Following the procedure of preparation 1A, but substituting the appropriate 3-substituted-phenylpropanol for 3-(3,4-dimethoxyphenyl)propanol, the 1-chloroethylbenzoxepins of Table 1A were prepared.

TABLE 1A 1. 9-methoxy-8-propyl-1-chloroethyl-1,3,4,5-tetrahydro-2-benzoxepin,
2. 9-methoxy-1-chloroethyl-1,3,4,5-tetrahydro-2-benzoxepin,
3. 6,7-dimethoxy-1-chloroethyl-1,3,4,5-tetrahydro-2-benzoxepin,
4. 7-ethoxy-1-chloroethyl-1,3,4,5-tetrahydro-2-benzoxepin,
5. 7,8,9-trimethoxy-1-chloroethyl-1,3,4,5-tetrahydro-2-benzoxepin,
6. 7-hydroxy-6-methoxy-1-chloroethyl-1,3,4,5-tetrahydro-2-benzoxepin,
7. 8-bromo-7-methoxy-1-chloroethyl-1,3,4,5-tetrahydro-2-benzoxepin,
8. 7-methoxy-8,9-dichloro-1-chloroethyl-1,3,4,5-tetrahydro-2-benzoxepin,
9. 7-methoxy-8-trifluoromethyl-1-chloroethyl-1,3,4,5-tetrahydro-2-benzoxepin,
10. 7,8-methylenedioxy-1-chloroethyl-1,3,4,5-tetrahydro-2-benzoxepin,
11. 7-methoxy-5-methyl-1-chloroethyl-1,3,4,5-tetrahydro-2-benzoxepin,
12. 7,9-dimethoxy-4,5-dimethyl-1-chloroethyl-1,3,4,5-tetrahydro-2-benzoxepin,
13. 7,8,9-trimethoxy-4-methyl-1-chloroethyl-1,3,4,5-tetrahydro-2-benzoxepin,
14. 9-methoxy-4-phenyl-1-chloroethyl-1,3,4,5-tetrahydro-2-benzoxepin,
15. 7-hydroxy-5-bromo-1-chloroethyl-1,3,4,5-tetrahydro-2-benzoxepin,
16. 7,8-dimethoxy-5,5-dimethyl-1-chloroethyl-1,3,4,5-tetrahydro-2-benzoxepin,
17. 7,8-dimethoxy-4,4-dimethyl-1-chloroethyl-1,3,4,5-tetrahydro-2-benzoxepin,
18. 1-(2-chloroethyl)-1,5-dihydro-7,8-dimethoxyspiro[2-benzoxepin-4(3H),1'-cyclopentane],
19. 6-chloroethyl-8,9-dipropyloxy-2,3,3a,4,6,10b-hexahydro-1H-benzo[c]cyclopent[e]oxepin,
20. 4-cyclopentyl-8,9-dimethoxy-1-chloroethyl-1,3,4,5-tetrahydro-2-benzoxepin,
21. 7,8-dihydroxy-5-propyl-1-chloroethyl-1,3,4,5-tetrahydro-2-benzoxepin,
22. 7,8-methoxy-9-trifluoromethyl-1-chloroethyl-1,3,4,5-tetrahydro-2-benzoxepin.

Preparation 1': Preparation of
3-(3,4-dimethoxyphenyl)-1-propanethiol

A mixture of 5.00 g (25.5 mmoles) of 3-(3,4-dimethoxyphenyl)propanol, 1.94 g (25.5 mmoles) of thiourea, and 8.5 ml of 48% hydrobromic acid is heated on steam bath for 1 hour, allowed to stand overnight at room temperature, and then heated again on a steam bath for 2 hours. After cooling, the reaction mixture is treated with 76.5 ml of 1 M sodium hydroxide and heated on the steam bath for 1½ hours. After cooling, the reaction mixture is made acidic with 1 N hydrochloric acid and extracted with methylene chloride (followed by a brine wash). Silica gel chromatography using 10% ethyl acetate/Skellysolve B as eluent gives 0.67 g of 3-(3,4-dimethoxyphenyl)-1-propanethiol.

Following the procedure of Preparation 1', but substituting the appropriate 3-substituted-phenyl-1-propanol for 3-(3,4-dimethoxyphenyl)-1-propanol, the phenyl-1-propanethiols of Table 1' can be prepared.

TABLE 1'

1. 3-(4,5-methoxypropylphenyl)-1-propanethiol,
2. 3-(5-methoxyphenyl)-1-propanethiol,
3. 3-(2,3-dimethoxyphenyl)-1-propanethiol,
4. 3-(3-ethoxyphenyl)-1-propanethiol,
5. 3-(3,4,5-trimethoxyphenyl)-1-propanethiol,
6. 3-(-3-hydroxy-2-methoxyphenyl)-1-propanethiol,
7. 3-(4-bromo-3-methoxyphenyl)-1-propanethiol,
8. 3-(4,5-dichloro-3-methoxyphenyl)-1-propanethiol,
9. 3-(3-methoxy-4-trifluoromethylphenyl)-1-propanethiol,
10. 3-(3,4-methylenedioxyphenyl)-1-propanethiol,
11. 3-(3-methoxyphenyl)-3-methyl-1-propanethiol,
12. 3-(3,5-dimethoxyphenyl)-2,3-dimethyl-1-propanethiol,
13. 3-(3,4,5-trimethoxyphenyl)-2-methyl-1-propanethiol,
14. 3-(5-methoxyphenyl)-2-phenyl-1-propanethiol,
15. 3-(3-hydroxyphenyl)-3-bromo-1-propanethiol,
16. 3-(3,4-dimethoxyphenyl)-3,3-dimethyl-1-propanethiol,
17. 3-(3,4-dimethoxyphenyl)-2,2-dimethyl-1-propanethiol,
18. 1-[(3,4-dimethoxyphenyl)methyl]cyclopent-1-yl-methanethiol,
19. 2-(3,4-dipropyloxyphenyl)cyclopent-1-yl-methanethiol,
20. 3-[(3,4-dimethoxyphenyl)-2-cyclopentyl)]-1-propanethiol,
21. 3-(3,4-dihydroxyphenyl)-3-n-propyl-1-propanethiol,
22. 3-(3,4-dimethoxy-5-trifluoromethylphenyl)-1-propanethiol.

Preparation 1B:
7,8-Dimethoxy-1-bromomethyl-1,3,4,5-tetrahydro-2-benzothiepin

A mixture of 0.67 g of 3-(3,4-dimethoxyphenyl)-1-propanethiol, 1.0 g of bromoacetaldehyde diethylacetal, 0.16 ml of trifluoroacetic acid, and 25 ml. of nitromethane as solvent is stirred at room temperature for 1 hour, stored overnight in the freezer, and then heated at 70° for 2 hours after an additional 0.05 ml trifluoroacetic acid is added. After cooling, the reaction mixture is extracted with methylene chloride and aqueous sodium bicarbonate. The organic layer is taken to dryness, and the residue is chromatographed one time on silica gel with methylene chloride as eluent and a second time with 10% ethyl acetate/Skellysolve B as eluent to yield 7,8-dimethoxy-1-bromomethyl-1,3,4,5-tetrahydro-2-benzothiepin.

Following the procedure of preparation 1B, but substituting the appropriate 3-phenyl-1-propanethiol from Table 1' for 3-(3,4-dimethoxyphenyl)-1-propanethiol, the 1-bromomethyl-2-benzothiepins of Table 1B can be prepared.

TABLE 1B 1. 7-propyl-9-methoxy-1-bromomethyl-1,3,4,5-tetrahydro-2-benzothiepin,
2. 9-methoxy-1-bromomethyl-1,3,4,5-tetrahydro-2-benzothiepin,
3. 6,7-dimethoxy-1-bromomethyl-1,3,4,5-tetrahydro-2-benzothiepin,
4. 7-ethoxy-1-bromomethyl-1,3,4,5-tetrahydro-2-benzothiepin,
5. 7,8,9-trimethoxy-1-bromomethyl-1,3,4,5-tetrahydro-2-benzothiepin,
6. 7-hydroxy-6-methoxy-1-bromomethyl-1,3,4,5-tetrahydro-2-benzothicpin,
7. 8-bromo-7-methoxy-1-bromomethyl-1,3,4,5-tetrahydro-2-benzothiepin,
8. 8,9-dichloro-7-methoxy-1-bromomethyl-1,3,4,5-tetrahydro-2-benzothiepin,
9. 7-methoxy-8-trifluoromethyl-1-bromomethyl-1,3,4,5-tetrahydro-2-benzothiepin,
10. 7,8-methylenedioxy-1-bromomethyl-1,3,4,5-tetrahydro-2-benzothiepin,
11. 7-methoxy-5-methyl-1-bromomethyl-1,3,4,5-tetrahydro-2-benzothiepin,
12. 7,9-dimethoxy-4,5-dimethyl-1-bromomethyl-1,3,4,5-tetrahydro-2-benzothiepin,
13. 7,8,9-trimethoxy-4-methyl-1-bromomethyl-1,3,4,5-tetrahydro-2-benzothiepin,
14. 9-methoxy-4-phenyl-1-bromomethyl-1,3,4,5-tetrahydro-2-benzothiepin,
15. 7-hydroxy-5-bromo-1-bromomethyl-1,3,4,5-tetrahydro-2-benzothiepin,
16. 7,8-dimethoxy-5,5-dimethyl-1-bromomethyl-1,3,4,5-tetrahydro-2-benzothiepin,
17. 7,8-dimethoxy-4,4-dimethyl-1-bromomethyl-1,3,4,5-tetrahydro-2-benzothiepin,
18. 1-(bromomethyl)-1,5-dihydro-7,8-dimethoxyspiro[2-benzothiepin-4(3H),1'-cyclopentane]
19. 6-bromomethyl-8,9-dipropyloxy-2,3,3a,4,6,10b-hexahydro-1H-benzo[c]cyclopent[e]thiepin,
20. 4-cyclopentyl-8,9-dimethoxy-1-bromomethyl-1,3,4,5-tetrahydro-2-benzothiepin,
21. 7,8-dihydroxy-5-n-propyl-1-bromomethyl-1,3,4,5-tetrahydro-2-benzothiepin,
22. 7,8-dimethoxy-9-trifluoromethyl-1-bromomethyl-1,3,4,5-tetrahydro-2-benzoxepin, Preparation 2:
6,7-Dimethoxy-1-(2-chloroethyl)isochroman To a solution of 3,4-dimethoxyphenethyl alcohol (110 g, 1.233 mole) and chloropropionaldehyde diethyl acetal (40 ml) in 240 ml of nitromethane, 8 ml of $BF_3$ etherate is added. The mixture is stirred for 2 hours at room temperature under $N_2$. This, after work up from water and extracting with methylene chloride gives a yellow oil. This, after column chromatography (silica gel), gives 45 g (oil) of 6,7-dimethoxy-1-(2-chloroethyl)isochroman which is crystallized from ether/pet. ether to give 41 g (70%) of 6,7-dimethoxy-1-(2-chloroethyl)isochroman as a white crystalline material, m.p. 56–57.5°.

Analysis Calcd for: $C_{13}H_{17}ClNO_3$: C, 60.82; H, 6.68; Cl, 13.96. Found: C, 60.81; H, 6.65; Cl, 13.96. Following the procedure of Preparation 2, but substituting the appropriate alcohol for 3,4-dimethoxyphenethyl alcohol, the 1-(2-chloroethyl) isochromans of Table 2 can be prepared.

TABLE 2

1. 8-methoxy-7-propyl-1-(2-chloroethyl)isochroman,
2. 8-methoxy-1-(2-chloroethyl)isochroman,
3. 5,6-dimethoxy-1-(2-chloroethyl)isochroman,
4. 6-ethoxy-1-(2-chloroethyl)isochroman,
5. 6,7,8-trimethoxy-1-(2-chloroethyl)isochroman,
6. 6-hydroxy-1-(2-chloroethyl)isochroman,
7. 6-methoxy-7-bromo-1-(2-chloroethyl)isochroman,
8. 6-methoxy-7,8-dichloro-1-(2-chloroethyl)isochroman,
9. 6-methoxy-7-trifluoromethyl-1-(2-chloroethyl)isochroman,
10. 6,7-methylenedioxy-1-(2-chloroethyl)isochroman,
11. 6-methoxy-4-methyl-1-(2-chloroethyl)isochroman,
12. 6,8-dimethoxy-3,4-dimethyl-1-(2-chloroethyl)-isochroman,
13. 6,7,8-trimethoxy-3-methyl-1-(2-chloroethyl)-isochroman,
14. 8-methoxy-3-phenyl-1-(2-chloroethyl)isochroman,
15. 6-hydroxy-4-bromo-1-(2-chloroethyl)isochroman,
16. 6,7-dimethoxy-4,4-dimethyl-1-(2-chloroethyl)isochroman,
17. 6,7-dimethoxy-3,3-dimethyl-1-(2-chloroethyl)isochroman,
18. 1-(2-chloroethyl)-6,7-dimethoxyspiro[1H-2-benzopyran-4(3H),1'-cyclopentane]
19. 5-(2-chloroethyl)-7,8-dipropyloxy-2,3,3a,5,9b, pentahydro-1H-benzo[c]cyclopent[e]pyran
20. 3-cyclopentyl-7,8-dimethoxy-1-(2-chloroethyl)-isochroman,
21. 6,7-dihydroxy-4-n-propyl-1-(2-chloroethyl)isochroman,
22. 6,7-dimethoxy-8-trifluoromethyl-1-(2-chloroethyl)isochroman.

Preparation 2A:
6,7-Dimethoxy-3,4-dihydro-1-(2-chloroethyl)-1H-2-benzothiopyran To a solution of 3,4-dimethoxy-phenethanethiol and chloropropionaldehyde diethyl acetal in nitromethane, $BF_3$ etherate is added. The mixture is stirred at room temperature under $N_2$. This, after work up from water, extracting with methylene chloride, on chromatography gives 6,7-dimethyl-1-(2-chloroethyl)-1H-2-benzothiopyran.

Following the procedure of Preparation 2A, but substituting the appropriate thiol of Table 2' for 3,4-dimethoxyphenethanethiol, the 1-(2-chloroethyl)-1H-2-benzothiopyrans of Table 2A can be prepared.

TABLE 2'

1. 2-(5-methoxy-4-propylphenyl)-1-ethanethiol,
2. 2-(5-methoxyphenyl)-1-ethanethiol,
3. 2-(2,3-dimethoxyphenyl)-1-ethanethiol,
4. 2-(3-ethoxyphenyl)-1-ethanethiol,
5. 2-(3,4,5-trimethoxyphenyl)-1-ethanethiol,
6. 2-(3-hydroxy-2-methoxyphenyl)-1-ethanethiol,
7. 2-(3-methoxy-4-bromophenyl)-1-ethanethiol,
8. 2-(3-methoxy-4,5-dichlorophenyl)-1-ethanethiol,
9. 2-(3-methoxy-4-trifluoromethylphenyl)-1-ethanethiol,
10. 2-(3,4-methylenedioxyphenyl)-2-ethanethiol,
11. 2-(3-methoxyphenyl)-2-methyl-1-ethanethiol,
12. 2-(3,5-dimethoxyphenyl)-1,2-dimethyl-1-ethanethiol,
13. 2-(3,4,5-trimethoxyphenyl)-2-methyl-1-ethanethiol,
14. 2-(5-methoxyphenyl)-2-phenyl-1-ethanethiol,
15. 2-(3-hydroxyphenyl)-2-bromo-1-ethanethiol,
16. 2-(3,4-dimethoxyhenyl)-2,2-dimethyl-1-ethanethiol,
17. 2-(3,4-dimethoxyphenyl)-1,1-dimethyl-1-ethanethiol,
18. [1-(3,4-dimethoxyphenyl;cyclopent-1-yl]methanethiol,
19. 2-(3,4-dipropyloxyphenyl)cyclopentan-1-thiol,
20. 2-(3,4-dimethoxyphenyl)-2-cyclopentyl-1-ethanethiol,
21. 2-(3,4-dimethoxyphenyl)-2-n-propyl-1-ethanethiol,
22. 2-(3,4-dimethoxy-5-trifluoromethylphenyl)-2-ethanethiol.

TABLE 2A 1. 8-methoxy-7-propyl-1-(2-chloroethyl)-1H-2-benzothiopyran,
2. 8-methoxy-1-(2-chloroethyl)-1H-2-benzothiopyran,
3. 5,6-dimethoxy-1-(2-chloroethyl)-1H-2-benzothiopyran,
4. 6-ethoxy-1-(2-chloroethyl)-1H-2-benzothiopyran,
5. 6,7,8-trimethoxy-1-(2-chloroethyl)-1H-2-benzothiopyran,
6. 6-hydroxy-1-(2-chloroethyl)-1H-2-benzothiopyran,
7. 6-methoxy-7-bromo-1-(2-chloroethyl)-1H-2-benzothiopyran,
8. 6-methoxy-7,8-dichloro-1-(2-chloroethyl)-1H-2-benzothiopyran,
9. 6-methoxy-7-trifluoromethyl-1-(2-chloroethyl)-1H-2-benzothiopyran,
10. 6,7-methylenedioxy-1-(2-chloroethyl)-1H-2-benzothiopyran,
11. 6-methoxy-4-methyl-1-(2-chloroethyl)-1H-2-benzothiopyran,
12. 6,8-dimethoxy-3,4-dimethyl-1-(2-chloroethyl)-1H-2-benzothipyran,
13. 6,7,8-trimethoxy-1-(2-chloroethyl)-1H-2-benzothiopyran,
14. 8-methoxy-3-phenyl-1-(2-chloroethyl)-1H-2-benzothiopyran,
15. 6-hydroxy-4-bromo-1-(2-chloroethyl)-1H-2-benzothiopyran,
16. 6,7-dimethoxy-4,4-dimethyl-1-(2-chloroethyl)-1H-2-benzothiopyran,
17. 6,7-dimethoxy-3,3-dimethyl-1-(2-chloroethyl)-1H-2-benzothiopyran,
18. 1-(2-chloroethyl)-6,7-dimethoxyspiro[1H-2-benzothiopyran-4-(3H),1'-cyclopentane],
19. 5-(2-chloroethyl)-7,8-dipropoxy-2,3,3a,5,9b-pentahydro-1H-benzo[c]cyclopent[e]thiopyran,
20. 3-cyclopentyl-7,8-dimethoxy-1-(2-chloroethyl)-1H-2-benzothiopyran,
21. 6,7-dihydroxy-4-n-propyl-1-(2-chloroethyl)-1H-2-benzothiopyran,
22. 6,7-dimethoxy-8-trifluoromethyl-1-(2-chloroethyl)-1H-2-benzothiopyran.

Preparation 2B:
2,2-Dimethyl-2-(3,4-dimethoxyphenyl)-ethanol

Lithium diisopropylamine (0.0057 m) is generated at −70° from nBuLi and diisopropylamine in THF and is added to a solution of 1.00 g. (0.0048 m) of ethyl 3,4-dimethoxyphenylacetate in 20 ml of dry THF. The reaction is stirred under nitrogen at −70° for 30 min. Methyl iodide (0.67 g, 0.0048 m) is injected. After 1 hour, another 0.0057 moles of lithium diisopropylamine is added, the reaction is stirred for 30 min., and methyliodide (0.67 g, 0.0048 m) is added. The reaction is warmed to room temperature over three hours. The mixture is partitioned between methylene chloride and aqueous sodium bicarbonate. The organic phase is dried ($Na_2SO_4$) and concentrated to yield 1.2 g of tan crystalline ethyl 2,2-dimethyl-(3,4-dimethoxyphenyl)acetate. This material is dissolved in 50 ml of 4:1 ether/THF. Lithium aluminum hydride (0.20 g) is added and the mixture is stirred and refluxed for 1.5 hrs. Water (0.2 ml), 15% aqueous sodium hydroxide (0.2 m), and water (0.6 ml) are sequentially added. The mixture is filtered through sodium sulfate and then partitioned between aqueous sodium carbonate and methylene chloride. The organic phase is dried (sodium sulfate and concentrated to yield 1.01 g of white crystalline 2,2-dimethyl-2-(3,4-dimethoxyphenyl)ethanol.

Preparation 2B':
6,7-Dimethoxy-1-bromomethylisochroman.

A mixture of 29.1 g. of 3,4-dimethoxyphenylethanol, 35 ml of bromoacetaldehyde dimethyl acetal and 5 ml of 48% HBr is stirred at 80° for 1.5 hr. The organic phase is mixed with 200 ml of methylene chloride and washed with water and then with 200 ml of 10% aqueous potassium carbonate. The organics are dried over sodium sulfate and chromatographed over silica gel. The product is crystallized from ether to yield 36.3 g. of the white solid, 70–80°.

Preparation 2B'':
4,4-Dimethyl-6,7-dimethoxy-1-bromomethylisochroman.

A 2,2-Dimethyl-2-(3,4-dimethoxyphenyl)ethanol (0.95 g, 0.0045 m) is stirred with 1.07 g (0.0054 m) of the ethyl acetal of bromoacetaldehyde and 0.19 g (0.0014 m) of $BF_3$.-etherate in 25 ml of nitromethane for 15 hours. The mixture is partitioned between methylene chloride and aqueous sodium carbonate. The organic phase is dried over sodium sulfate and concentrated to yield 1.52 g of 4,4-dimethyl-6,7-dimethoxy-1-bromomethylisochroman. The nmr is consistent with the assigned structure.

Following the procedures of Preparations 2B and 2B', but substituting the appropriate alcohols for 3,4-dimethoxyphenethyl alcohol, the 1-bromomethylisochromans of Table 2B'' can be prepared.

TABLE 2B'

1. 8-methoxy-7-n-propyl-1-bromomethylisochroman,
2. 8-methoxy-1-bromomethylisochroman,
3. 5,6-dimethoxy-1-bromomethylisochroman,
4. 6-ethoxy-1-bromomethylisochroman,
5. 6,7,8-trimethoxy-1-bromomethylisochroman,
6. 6-hydroxy-1-bromomethylisochroman,
7. 6-methoxy-7-bromo-1-bromomethylisochroman,
8. 6-methoxy-7,8-dichloro-1-bromomethylisochroman,
9. 6-methoxy-7-trifluoromethyl-1-bromomethylisochroman,
10. 6,7-methylenedioxy-1-bromomethylisochroman,
11. 6-methoxy-4-methyl-1-bromemethylisochroman,
12. 6,8-dimethoxy-3,4-dimethyl-1-bromomethylisochroman,
13. 6,7,8-trimethoxy-1-bromomethylisochroman,
14. 8-methoxy-3-phenyl-1-bromomethylisochroman,
15. 6-hydroxy-4-bromo-1-bromomethylisochroman,
16. 6,7-dimethoxy-4,4-dimethyl-1-bromomethylisochroman,
17. 6,7-dimethoxy-3,3-dimethyl-1-bromomethylisochroman,
18. 1-bromomethyl-6,7-dimethoxyspiro[1H-2-benzopyran-4(3H),1'-cyclopentane],
19. 5-bromomethyl-7,8-dipropoxy-2,3,3a,5,9b-pentahydro-1H-benzo[c]cyclopent[e]pyran,
20. 3-cyclopentyl-7,8-dimethoxy-1-bromomethylisochroman,
21. 6,7-dihydroxy-4-n-propyl-1-bromomethylisochroman,
22. 6,7-dimethoxy-8-trifluoromethyl-1-bromomethylisochroman.

Preparation 2C:
6,7-Dimethoxy-1-bromomethyl-3,4-dihydro-1H-2-benzothiopyran.

A mixture of 3,4-dimethoxyphenylethane thiol, bromoacetaldehyde dimethylacetal, and $BF_3$.etherate in nitromethane is stirred at 40°. The product is dissolved in methylene chloride and washed with aqueous sodium bicarbonate. Chromatography on silica gel is used to isolate the product.

Following the procedure of Preparation 2C, but substituting the appropriate thiols for 3,4-dimethoxyphenylethane thiol, the 1-bromomethyl-3,4-dihydro-1H-2-benzothiopyrans of Table 2C can be prepared.

TABLE 2C 1. 8-methoxy-7-n-propyl-1-bromomethyl-3,4-dihydro-1H-2-benzothiopyran,
2. 8-methoxy-1-bromomethyl-3,4-dihydro-1H-2-benzothiopyran,
3. 5,6-dimethoxy-1-bromomethyl-3,4-dihydro-1H-2-benzothiopyran,
4. 6-ethoxy-1-bromomethyl-3,4-dihydro-1H-2-benzothiopyran,
5. 6,7,8-trimethoxy-1-bromomethyl-3,4-dihydro-1H-2-benzothiopyran,
6. 6-hydroxy-1-bromomethyl-3,4-dihydro-1H-2-benzothiopyran,
7. 6-methoxy-7-bromo-1-bromomethyl-3,4-dihydro-1H-2-benzothiopyran,
8. 6-methoxy-7,8-dichloro-1-bromomethyl-3,4-dihydro-1H-2-benzothiopyran,
9. 6-methoxy-7-trifluoromethyl-1-bromomethyl-3,4-dihydro-1H-2-benzothiopyran,
10. 6,7-methylenedioxy-1-bromo-3,4-dihydro-1H-2-benzothiopyran,
11. 6-methoxy-4-methyl-1-bromomethyl-3,4-dihydro-1H-2-benzothiopyran,
12. 6,8-dimethoxy-3,4-dimethyl-1-bromomethyl-3,4-dihydro-1H-2-benzothiopyran,
13. 6,7,8-trimethoxy-1-bromomethyl-3,4-dihydro-1H-2-benzothiopyran,
14. 8-methoxy-3-phenyl-1-bromomethyl-3,4-dihydro-1H-2-benzothiopyran,
15. 6-hydroxy-4-bromo-1-bromomethyl-3,4-dihydro-1H-2-benzothiopyran,
16. 6,7-dimethoxy-4,4-dimethyl-1-bromomethyl-3,4-dihydro-1H-2-benzothiopyran,
17. 6,7-dimethoxy-3,3-dimethyl-1-bromomethyl-3,4-dihydro-1H-2-benzothiopyran,
18. 1-(bromomethyl)-6,7-dimethoxyspiro[1H-2-benzothiopyran-4(3H),1'-cyclopentane], 19. 5-bromomethyl-7,8-dipropoxy-2,3,3a,5,9b-pentahydro-1H-benzo[c]cyclopent[e]thiopyran,
20. 3-cyclopentyl-7,8-dimethoxy-1-bromomethyl-3,4-dihydro-1H-2-benzothiopyran,
21. 6,7-dihydroxy-4-n-propyl-1-bromomethyl-3,4-dihydro-1H-2-benzothiopyran,
22. 6,7-dimethoxy-8-trifluoromethyl-1-bromomethyl-3,4-dihydro-1H-2-benzothiopyran, Preparation 3:
1-(3-chloropropyl)-6,7-dimethoxy-1-methyl-isochroman.

A mixture of 3,4-dimethoxyphenylethyl alcohol (1.72 g, 0.01 mole), 5-chloro-2-pentanone ethylene ketal (1.64 g, 0.01 mole) and 0.5 ml of $BF_3$ etherate in 20 ml of nitromethane is stirred at room temperature under $N_2$ for 4 hours. The reaction mixture is then poured into cold water and extracted with $CH_2Cl_2$. The $CH_2Cl_2$ solution is washed with water, dried ($Na_2SO_4$) and concentrated to an oil. The oil is chromatographed on silica gel with 10% ethylacetate/Skellysolve B as eluate to give 40 g (54% yield) of 1-(3-chloropropyl)-6,7-dimethoxy-1-methyl-isochroman as a white crystalline product, m.p. 77°–79° C. The nmr of the product is consistent with the structure.

Following the procedure of Preparation 3, but substituting the appropriate alcohol for 3,4-dimethoxyphenethyl alcohol, the 1-(3-chloropropyl)-1-methylisochromans of Table 3 can be prepared.

TABLE 3

1. 8-methoxy-7-n-propyl-1-methyl-1-(3-chloropropyl)-isochroman,
2. 8-methoxy-1-methyl-1-(3-chloropropyl)isochroman,
3. 5,6-dimethoxy-1-methyl-1-(3-chloropropyl)isochroman,
4. 6-ethoxy-1-methyl-1-(3-chloropropyl)isochroman,
5. 6,7,8-trimethoxy-1-methyl-1-(3-chloropropyl)isochroman,
6. 6-hydroxy-1methyl-1-(3-chloropropyl)isochroman,
7. 6-methoxy-7-bromo-1-methyl-1-(3-chloropropyl)isochroman,
8. 6-methoxy-7,8-dichloro-1-methyl-1-(3-chloropropyl)isochroman,
9. 6-methoxy-7-trifluoromethyl-1-methyl-1-(3-chloropropyl)isochroman,
10. 6,7-methylenedioxy-1-methyl-1-(3-chloropropyl)-isochroman,
11. 6-methoxy-4-methyl-1-methyl-1-(3-chloropropyl)isochroman,
12. 6,8-dimethoxy-3,4-dimethyl-1-methyl-1-(3-chloropropyl)isochroman,
13. 6,7,8-trimethoxy-1-methyl-1-(3-chloropropyl)isochroman,
14. 8-methoxy-3-phenyl-1-methyl-1-(3-chloropropyl)isochroman,
15. 6-hydroxy-4-bromo-1-methyl-1-(3-chloropropyl)isochroman,
16. 6,7-dimethoxy-4,4-dimethyl-1-methyl-1-(3-chloropropyl)isochroman,
17. 6,7-dimethoxy-3,3-dimethyl-1-methyl-1-(3-chloropropyl)isochroman,
18. 1-methyl-1-(3-chloropropyl)-6,7-dimethoxyspiro[1H-2-benzopyran-4(3H),1'-cyclopentane],
19. 5-methyl-5-(3-chloropropyl)-7,8-dipropoxy-2,3,3a,5,9b-pentahydro-1H-benzo[c]cyclopent[e]pyran,
20. 3-cyclopentyl-7,8-dimethoxy-1-methyl-1-(3-chloropropyl)isochroman,
21. 6,7-dihydroxy-4-n-propyl-1-methyl-1-(3-chloropropyl)isochroman,
22. 6,7-dimethoxy-8-trifluoromethyl-1-methyl-1-(3-chloropropyl)isochroman.

Preparation 3A:
1-(3-Chloropropyl)-3,4-dihydro-6,7-dimethoxy-1-methyl-1H-2-benzothiopyran.

A mixture of 3,4-dimethoxyphenylethanethiol, 5-chloro-2-pentanone ethylene ketal and $BF_3$ etherate in nitromethane is stirred under $N_2$. The reaction mixture is then poured into cold water and extracted with $CH_2Cl_2$. The $CH_2Cl_2$ solution is washed with water, dried, ($Na_2SO_4$) and concentrated. Column chromatography of the concentrate gives 1-(3-chloropropyl)-3,4-dihydro-6,7-dimethoxy-1-methyl-1H-2-benzothiopyran.

Following the procedure of Preparation 3A, but substituting the appropriate thiol for 3,4-dimethoxyphenylethanethiol, the 1-(3-chloropropyl)-3,4-dihydro-6,7-dimethoxy-1-methyl-1H-2-benzothiopyrans of Table 3A can be prepared.

TABLE 3A 1. 8-methoxy-7-n-propyl-1-(3-chloropropyl)-1-methyl-3,4-dihydro-1H-2-benzothiopyran,
2. 8-methoxy-1-(3-chloropropyl)-1-methyl-3,4-dihydro-1H-2-benzothiopyran,
3. 5,6-dimethoxy-1-(3-chloropropyl)-1-methyl-3,4-dihydro-1H-2-benzothiopyran,
4. 6-ethoxy-1-(3-chloropropyl)-1-methyl-3,4-dihydro-1H-2-benzothiopyran,
5. 6,7,8-trimethoxy-1-(3-chloropropyl)-1-methyl-3,4-dihydro-1H-2-benzothiopyran,
6. 6-hydroxy-1-(3-chloropropyl)-1-methyl-3,4-dihydro-1H-2-benzothiopyran,
7. 6-methoxy-7-bromo-1-(3-chloropropyl)-1-methyl-3,4-dihydro-1H-2-benzothiopyran,
8. 6-methoxy-7,8-dichloro-1-(3-chloropropyl)-1-methyl-3,4-dihydro-1H-2-benzothiopyran,
9. 6-methoxy-7-trifluoromethyl-1-(3-chloropropyl)-1-methyl-3,4-dihydro-1H-2-benzothiopyran,
10. 6,7-methylenedioxy-1-(3-chloropropyl)-1-methyl-3,4-dihydro-1H-2-benzothiopyran,
11. 6-methoxy-4-methyl-1-(3-chloropropyl)-1-methyl-3,4-dihydro-1H-2-benzothiopyran,
12. 6,8-dimethoxy-3,4-dimethyl-1-(3-chloropropyl)-1-methyl-3,4-dihydro-1H-2-benzothiopyran,
13. 6,7,8-trimethoxy-1-(3-chloropropyl)-1-methyl-3,4-dihydro-1H-2-benzothiopyran,
14. 8-methoxy-3-phenyl-1-(3-chloropropyl)-1-methyl-3,4-dihydro-1H-2-benzothiopyran,
15. 6-hydroxy-4-bromo-1-(3-chloropropyl)-1-methyl-3,4-dihydro-1H-2-benzothiopyran,
16. 6,7-dimethoxy-4,4-dimethyl-1-(3-chloropropyl)-1-methyl-3,4-dihydro-1H-2-benzothiopyran,
17. 6,7-dimethoxy-3,3-dimethyl-1-(3-chloropropyl)-1-methyl-3,4-dihydro-1H-2-benzothiopyran,
18. 1-methyl-1-(3-chloropropyl)-6,7-dimethoxyspiro[1H-2-benzothiopyran-4(3H),1'-cyclopentane]
19. 1-methyl-1-(3-chloropropyl)-7,8-dipropoxy-2,3,3a,5,9b-pentahydro-1H-benzo[c]cyclopent[e]thiopyran,
20. 3-cyclopentyl-7,8-dimethoxy-1-methyl-1-(3-chloropropyl)-3,4-dihydro-1H-2-benzothiopyran,
21. 6,7-dihydroxy-4-n-propyl-1-(3-chloropropyl)-1-methyl-3,4-dihydro-1H-2-benzothiopyran, 22. 6,7-dimethoxy-8-trifluoromethyl-1-(3-chloropropyl)-1-methyl-3,4-dihydro-1H-2-benzothiopyran.

Preparation 4

Following the procedures of Preparations 1–3 but substituting the appropriate halo-substituted ketone or aldehydes from Table 4' the following 1-halo-alkyl benzexepins wherein the alkyl group is a branched chain or $(CH_2)_3$ to 5 can be prepared from 3-(3,4,-dimethoxyphenyl)-propanol.

Table 4

1. 7,8-dimethoxy-1[5-bromopentyl]-1,3,4,5-tetrahydro-2-benzoxepin,
2. 7,8-dimethoxy-1-[4-chlorobutyl]-1,3,4,5-tetrahydro-2-benzoxepin,
3. 7,8-dimethoxy-1-[3-cholorpropyl]-1,3,4,5-tetrahydro-2-benzoxepin,
4. 7,8-dimethoxy-1-[1-methyl-3-chloropropyl]-1,3,4,5-tetrahydro-2-benzoxepin,
5. 7,8-dimethoxy-1-[2,2-dimethyl-3-bromopropyl]-1,3,4,5-tetrahydro-2-benzoxepin,
6. 7,8-dimethoxy-1-[1-ethyl-4-chlorobutyl]-1,3,4,5-tetrahydro-2-benzoxepin,
7. 7,8-dimethoxy-1-[1,4-dimethyl-5-brompentyl]-1,3,4,5-tetrahydro-2-benzoxepin,
8. 7,8-dimethoxy-1-[5-bromopentyl]-1-methyl-1,3,4,5-tetrahydro-2-benzoxepin,
9. 7,8-dimethoxy-1-[4-chlorobutyl]-1-methyl-1,3,4,5-tetrahydro-2-benzoxepin,
10. 7,8-dimethoxy-1-[3-chloropropyl]-1-methyl-1,3,4,5-tetrahydro-2-benzoxepin,
11. 7,8-dimethoxy-1-[methyl-3-chloropropyl]-1-methyl-1,3,4,5-tetrahydro-2-benzoxepin,
12. 7,8-dimethoxy-1-[2,2-dimethyl-3-bromopropyl]-methyl-1,3,4,5-tetrahydro-2-benzoxepin, 13. 7,8-dimethoxy-1-[1-ethyl-4-chlorobutyl]-methyl-1,3,4,5-tetrahydro-2-benzoxepin,
14. 7,8-dimethoxy-1-[1,4-dimethyl-5-bromopenyl)-methyl-1,3,4,5-tetrahydro-2-benzoxepin,
15. 7,8-dimethoxy-1-[5-bromopenyl]-1-(4'-fluorophenyl)-1,3,4,5-tetrahydro-2-benzoxepin,
16. 7,8-dimethoxy-1-[4-chlorobutyl]-1-(4'-fluorophenyl)-1,3,4,5-tetrahydro-2-benzoxepin,
17. 7,8-dimethoxy-1-[3-chloropropyl]-1-(4'-fluorophenyl)-1,3,4,5-tetrahydro-2-benzoxepin,
18. 7,8-dimethoxy-1-[1-methyl-3-chloropropyl]-1-(4'-fluorophenyl)-1,3,4,5-tetrahydro-2-benzoxepin,
19. 7,8-dimethoxy-1-[2,2-dimethyl-3-bromopropyl]-1-(4'-fluorophenyl)-1,3,4,5-tetrahydro-2-benzoxepin,
20. 7,8-dimethoxy-1-[1-ethyl-4-chlorobutyl]-1-(4'-fluorophenyl)-1,3,4,5-tetrahydro-2-benzoxepin,
21. 7,8-dimethoxy-1-[1,4-dimethyl-5-bromopentyl]-1-(4'-fluorophenyl)-1,3,4,5-tetrahydro-2-benzoxepin, The compounds of Table 4 are derived from the aldehyde or ketones of Table 4' and 3-(3,4-dimethoxy phenyl)propanol.

TABLE 4'

1. methyl 5-bromopentyl ketone,
2. methyl 4-chlorobutyl ketone,
3. methyl 3-chloropropyl ketone,
4. 6-bromohexanal,
5. 5-chloropentanal,
6. 4-chlorobutanal,
7. p-fluorophenyl 5-bromopentyl ketone,
8. p-fluorophenyl 4-chlorobutyl ketone,
9. p-fluorophenyl 3-chloropropyl ketone,
10. 2-methyl-4-chlorobutanal,
11. 3,3-dimethyl-4-bromobutanal,
12. 2-ethyl-5-chloropentanal,
13. 2,5-dimethyl-6-bromohexanal,
14. methyl (1-methyl-3-chloropropyl ketone,
15. methyl 2,2-dimethyl-3-bromopropyl ketone,
16. methyl 1-ethyl-4-chlorobutyl ketone,
17. methyl 1,4-dimethyl-5-bromopentyl ketone,
18. p-fluorophenyl 1-methyl-3-chloropropyl ketone,
19. p-fluorophenyl 2,2-dimethyl-3-bromopropyl ketone,
20. p-fluorophenyl 1-ethyl-4-chlorobutyl ketone,
21. p-fluorophenyl 1,4-dimethyl-5-bromopentyl ketone, Similarly, from the alcohols which were used to prepare the benzoxepins of Table 1 and the appropriate halo substituted ketones or aldehydes (Table 4') and following the procedures of Preparation 1–3 the benzoxepins which are analogous to those of Table 4 can be prepared.

Preparation 4a

Following the procedures of Preparations 1a to 3a, and 2c, but substituting the appropriate halo-substituted ketone or aldehyde, the following halo-alkyl benzothiepins, wherein the alkyl group is a branched chain or $(CH_2)_3$ to 5 can be prepared from 3-(3,4-dimethoxyphenyl)-1-propanethiol (Table 4a).

Table 4a 1. 7,8-dimethoxy-1-[5-bromopentyl]-1,3,4,5-tetrahydro-2-benzothiepin,
2. 7,8-dimethoxy-1-[4-chlorobutyl]-1,3,4,5-tetrahydro-2-benzothiepin,
3. 7,8-dimethoxy-1-[3-chloropropyl]-1,3,4,5-tetrahydro-2-benzothiepin,
4. 7,8-dimethoxy-1-[1-methyl-3-chloropropyl]-tetrahydro-2-benzoethiepin,
5. 7,8-dimethoxy-1-[2,2-dimethyl-3-bromopropyl]-1,3,4,5-tetrahydro-2-benzothiepin,
6. 7,8-dimethoxy-1-[1-ethyl-4-chlorobutyl]-1,3,4,5-tetrahydro-2-benzothiepin,
7. 7,8-dimethoxy-1-[1,4-dimethyl-5-bromopentyl]-1,3,4,5-tetrahydro-2-benzothiepin,
8. 7,8-dimethoxy-1-[5-bromopentyl]-1,3,4,5-tetrahydro-2-benzothiepin,
9. 7,8-dimethoxy-1-[4-chlorobutyl]-1-methyl-1,3,4,5-tetrahydro-2-benzothiepin,
10. 7,8-dimethoxy-1-[3-chloropropyl]-1-methyl-1,3,4,5-tetrahydro-2-benzothiepin,
11. 7,8-dimethoxy-1-[1-methyl-3-chloropropyl]-1-methyl-1,3,4,5-tetrahydro-2-benzothiepin,
12. 7,8-dimethoxy-1-[2,2-dimethyl-3-bromopropyl]-1-methyl-1,3,4,5-tetrahydro-2-benzothiepin,
13. 7,8-dimethoxy-1-[1-ethyl-4-chlorobutyl]-1-methyl-1,3,4,5-tetrahydro-2-benzothiepin,
14. 7,8-dimethoxy-1-[1,4-dimethyl-5-bromopentyl]-1-methyl-1,3,4,5-tetrahydro-2-benzothiepin,
15. 7,8-dimethoxy-1-[5-bromopentyl]-1-(4'-fluorophenyl)-1,3,4,5-tetrahydro-2-benzothiepin,
16. 7,8-dimethoxy-1-[4-chlorobutyl]-1-(4'-fluorophenyl)-1,3,4,5-tetrahydro-2-benzothiepin,
17. 7,8-dimethoxy-1-[3-chloropropyl]-1-(4'-fluorophenyl)-1,3,4,5-tetrahydro-2-benzothiepin,
18. 7,8-dimethoxy-1-[1-methyl-3-chloropropyl]-1-(4'-fluorophenyl)-1,3,4,5-tetrahydro-2-benzothiepin,
19. 7,8-dimethoxy-1-[2,2-dimethyl-3-bromopropyl]-1-(4'-fluorophenyl)-1,3,4,5,-tetrahydro-2-benzothiepin,
20. 7,8-dimethoxy-1-[1-ethyl-4-chlorobutyl]-1-(4'-fluorophenyl)-1,3,4,5-tetrahydro-2-benzothiepin, 21. 7,8-dimethoxy-1-[1,4-dimethyl-5-bromopentyl]-1-4'-fluorophenyl)-1,3,4,5-tetrahydro-2-benzothiepin, Similarly, from the thiols from Table 1' and the appropriate substituted ketones or aldehydes of Table 4' and following the procedures of Preparation 1a–3a the benzoethiepins which are analogous to those of Table 4a can be prepared.

Preparation 4b

Following the procedures of Preparations 2, 2b, and 3 but substituting the appropriate halo-substituted ketones or aldehydes from Table 4', the following 1-haloalkyl isochromans wherein the alkyl group is a branched chain or $(CH_2)_3$ to 5 can be prepared from 3-(3,4-dimethoxy phenyl)ethanol (Table 4b).

TABLE 4b 1. 6,7-dimethoxy-1-[5-bromopentyl]isochroman,
2. 6,7-dimethoxy-1-[4-chlorobutyl]isochroman,
3. 6,7-dimethoxy-1-[3-chloropropyl]isochroman,
4. 6,7-dimethoxy-1-[1-methyl-3-chloropropyl]isochroman,
5. 6,7-dimethoxy-1-[2,2-dimethyl-3-bromopropyl]isochroman,
6. 6,7-dimethoxy-1-[1-ethyl-4-chlorobutyl]isochroman,
7. 6,7-dimethoxy-1-[5-bromopentyl]isochroman,
8. 6,7-dimethoxy-1-methyl-1-[5-bromopentyl]isochroman,
9. 6,7-dimethoxy-1-[4-chlorobutyl]-1-methylisochroman,
10. 6,7-dimethoxy-1-[3-chloropropyl]-1-methylisochroman,
11. 6,7-dimethoxy-1-[1-methyl-3-chloropropyl]-1-methylisochroman,
12. 6,7-dimethoxy-1-[2,2-dimethyl-3-bromopropyl]-1-methylisochroman,
13. 6,7-dimethoxy-1-[1-ethyl-4-chlorobutyl]-1-methylisochroman,
14. 6,7-dimethoxy-1-[1,4-dimethyl-5-bromopentyl]-1-methylisochroman,
15. 6,7-dimethoxy-1-[5-bromopentyl]-1-(4'-fluorophenyl)isochroman,
16. 6,7-dimethoxy-1-[4-chlorobutyl]-1-(4'-fluorophenyl)isochroman,
17. 6,7-dimethoxy-1-[3-chloropropyl]-1-(4'-fluorophenyl)isochroman,
18. 6,7-dimethoxy-1-[1-methyl-3-chloropropyl]-1-(4'-fluorophenyl)isochroman,
19. 6,7-dimethyl-[2,2-dimethyl-3-bromopropyl]-1-(4'-fluorophenyl)isochroman,
20. 6,7-dimethoxy-1-[1-ethyl-4-chlorobutyl]-1-(4'-fluorophenyl)isochroman,
21. 6,7-dimethoxy-1-[1,4-dimethyl-5-bromopentyl]-1-(4'-fluorophenyl)isochroman.

Similarly, from the alcohols which were used to prepare the isochromans of Tables 2, 2b, and 3 and the appropriate halo substituted ketones or aldehydes from Table 4', and following the procedures of Preparations 2, 2b, and 3 the isochromans which are analogous to those of Table 4b can be prepared.

Preparation 4c

Following the procedures of preparations 2a, 2c, and 3a but substituting the appropriate halo-substituted ketones or aldehydes from Table 4', the following 1-haloalkyl-3,4-dihydro-1H-2-benzothiopyrans wherein the alkyl group is a branched chain or $(CH_2)_3$ to 5 can be prepared from 2-(3,4-dimethoxyphenyl)ethanethiol (Table 4c).

TABLE 4c 1. 6,7-dimethoxy-1-(5-bromopentyl)-3,4-dihydro-1H-2-benzothiopyran,
2. 6,7-dimethoxy-1-(4-chlorobutyl)-3,4-dihydro-1H-2-benzothiopyran,
3. 6,7-dimethoxy-1-(3-chloropropyl)-3,4-dihydro-1H-2-benzothiopyran,
4. 6,7-dimethoxy-1-(1-methyl-3-chloropropyl)-3,4-dihydro-1H-2-benzothiopyran,
5. 6,7-dimethoxy-1-(2,2-dimethyl-3-bromopropyl)-3,4-dihydro-1H-2-benzothiopyran,
6. 6,7-dimethoxy-1-(1-ethyl-4-chlorobutyl)-3,4-dihydro-1H-2-benzothiopyran,
7. 6,7-dimethoxy-1-(1,4-dimethyl-5-bromopentyl)-3,4-dihydro-1H-2-benzothiopyran,
8. 6,7-dimethoxy-1-(5-bromopentyl)-1-methyl-3,4-dihydro-1H-2-benzothiopyran,
9. 6,7-dimethoxy-1-(4-chlorobutyl)-1-methyl-3,4-dihydro-1H-2-benzothiopyran,
10. 6,7-dimethoxy-1-(3-chloropropyl)-1-methyl-3,4-dihydro-1H-2-benzothiopyran,
11. 6,7-dimethoxy-1-(1-methyl-3-chloropropyl)-1-methyl-3,4-dihydro-1H-2-benozthiopyran,
12. 6,7-dimethoxy-1-(2,2-dimethyl-5-bromopentyl)-1-methyl-3,4-dihydro-1H-2-benzothiopyran,
13. 6,7-dimethoxy-1-(1-ethyl-4-chlorobutyl)-1-methyl-3,4-dihydro-1H-2-benozthiopyran,
14. 6,7-dimethoxy-1-(1,4-dimethyl-5-bromopentyl)-1-methyl-3,4-dihydro-1H-2-benzothiopyran,
15. 6,7-dimethoxy-1-(5-bromopentyl)-1-(4'-fluorophenyl)-1-methyl-3,4-dihydro-1H-2-benzothiopyran,
16. 6,7-dimethoxy-1-(4-chlorobutyl)-1-methyl-3,4-dihydro-1H-2-benzothiopyran,
17. 6,7-dimethoxy-1-(3-chloropropyl)-1-methyl-3,4-dihydro-1H-2-benzothiopyran,
18. 6,7-dimethoxy-1-(1-methyl-3-chloropropyl)-1-methyl-3,4-dihydro-1H-2-benzothiopyran,
19. 6,7-dimethoxy-1-(2,2-dimethyl-3-bromopropyl)-1-methyl-3,4-dihydro-1H-2-benzothiopyran,
20. 6,7-dimethoxy-1-(1-ethyl-4-chlorobutyl)-1-methyl-3,4-dihydro-1H-2-benozthiopyran,
21. 6,7-dimethoxy-1-(1,4-dimethyl-5-bromopentyl)-1-methyl-3,4-dihydro-1H-2-benzothiopyran.

Similarly, from the thiols from Table 2' and the appropriate substituted ketones or aldehydes of Table 4' and following the procedures of Preparation 2a, 2c, and 3a the benzothiopyrans which are analogous to those of Table 4a can be prepared.

Preparation 5:
2-[(1,3,4,5-Tetrahydro-7,8-dimethoxy-2-benzoxepin-1-yl)methoxy]ethyl chloride A mixture of 10.33 g (0.343 moles) of 1-bromomethyl-1,3,4,5-tetrahydro-7,8-dimethoxy-2-benzoxepin, 10 ml of 2-chloroethanol, and 6.77 g of barium carbonate is stirred at 90° for 46 hours. The reaction mixture is then cooled, ethanol is added, and the solids are removed by filtration. The filtrate is taken to dryness in vacuo and the resulting oil is extracted with methylene chloride and aqueous sodium bicarbonate. The organic layer is then taken to dryness and chromatographed on silica gel using 10% ethylacetate:Skellysolve B as eluent to give 4.18 g (41%) of 2-[(1,3,4,5-tetrahydro-7,8-dimethoxy-2-benzoxepin-1-yl)methoxy]ethyl chloride, m.p. 90°–91°.

Analysis Calc'd for: $C_{15}H_{21}ClO_4$: C, 59.89; H, 7.04. Found: C, 60.06; H, 7.57.

Following the procedure of Preparation 5, but substituting the appropriate 1-bromomethyl 2-benzoxepin from Table 1 for 1-bromomethyl-7,8-dimethoxybenzoxepin and chloroethanol the 2-[(1,3,4,5-tetrahydro-2-benzoxepin-1-yl)methoxy]ethyl chlorides of Table 5 can be prepared.

TABLE 5

1. 2-[(9-methoxy-8-propyl-1,3,4,5-tetrahydro-2-benzoxepin-1-yl)methoxy]ethyl chloride,
2. 2-[(2-methoxy-1,3,4,5-tetrahydro-2-benozoxepin-1-yl)methoxy]ethyl chloride,
3. 2-[(6,7-dimethoxy-1,3,4,5-tetrahydro-2-benzoxepin-1-yl)methoxy]ethyl chloride,
4. 2-[(7-ethoxy-1,3,4,5-tetrahydro-2-benozxepin-1-yl)methoxy]ethyl chloride,
5. 2-[(7,8,9-trimethoxy-1,3,4,5-tetrahydro-2-benzoxepin-1-yl)methoxy]ethyl chloride,
6. 2-[(7-hydroxy-6-methoxy-1,3,4,5-tetrahydro-2-benzoxepin-1-yl)methoxy]ethyl chloride,
7. 2-[(8-bromo-7-methoxy-1,3,4,5-tetrahydro-2-benzoxepin-1-yl)methoxy]ethyl chloride,
8. 2-[(7-methoxy-8,9-dichloro-1,3,4,5-tetrahydro-2-benzoxepin-1-yl)methoxy]ethyl chloride,
9. 2-[(7-methoxy-8-trifluoromethyl-1,3,4,5-tetrahydro-2-benzoxepin-1-yl)methoxy]ethyl chloride,
10. 2-[(7,8-methylenedioxy-1,3,4,5-tetrahydro-2-benzoxepin-1-yl)methoxy]ethyl chloride,
11. 2-[(7-methoxy-5-methyl-1,3,4,5-tetrahydro-2-benzoxepin-1-yl)methoxy]ethyl chloride,
12. 2-[(7,9-dimethoxy-4,5-dimethyl-1,3,4,5-tetrahydro-2-benzoxepin-1-yl)methoxy]ethyl chloride,
13. 2-[(7,8,9-trimethoxy-4-methyl-1,3,4,5-tetrahydro-2-benzoxepin-1-yl)methoxy]ethyl chloride,
14. 2-[(9-methoxy-4-phenyl-1,3,4,5-tetrahydro-2-benzoxepin-1-yl)methoxy]ethyl chloride,
15. 2-[(7-hydroxy-5-bromo-1,3,4,5-tetrahydro-2-benzoxepin-1-yl)methoxy]ethyl chloride,
16. 2-[(7,8-dimethoxy-5,5-dimethyl-1,3,4,5-tetrahydro-2-benzoxepin-1-yl)methoxy]ethyl chloride,
17. 2-[(7,8-dimethoxy-4,4-dimethyl-1,3,4,5-tetrahydro-2-benzoxepin-1-yl)methoxy]ethyl chloride,
18. 1-(2-chloroethoxymethyl)-1,5-dihydro-7,8-dimethoxyspiro[2-benzoxepin-4(3H),1'-cyclopentane],
19. 6-(2-chloroethoxymethyl)-8,9-dipropoxy-2,3,3a,4,6,10b-hexahydro-1H-benzo[c]cyclopent[e]oxepin,
20. 2-[(4-chloropentyl-8,9-dimethoxy-1,3,4,5-tetrahydro-2-benzoxepin-1-yl)methoxy]ethyl chloride,
21. 2-[(7,8-dihydroxy-5-propyl-1,3,4,5-tetrahydro-2-benzoxepin-1-yl)methoxy]ethyl chloride,
22. 2-[(7,8-dimethoxy-9-trifluoromethyl-1,3,4,5-tetrahydro-2-benzoxepin-1-yl)methoxy]ethyl chloride.

Similarly from chloroethanol and the appropriate 1-chloroethylbenzoxepins of Table 1b or the 1-chloropropylbenzoxepins of Table 3a, and following the procedures of preparation 5, the analogous 2-[(1,3,4,5-tetrahydro-2-benzoxepin-1-yl)alkoxy]ethyl chlorides can be prepared.

Preparation 5a:
2-[(1,3,4,5-tetrahydro-7,8-dimethoxy-2-benzothiepin-1-yl)methoxy]ethyl chloride A mixture of 1-bromomethyl-7,8-dimethoxybenzothiepin, 2-chloroethanol, and barium carbonate is stirred at 40°-90° for 10-60 hours. The reaction mixture is then cooled, ethanol is added, and the solids are removed by filtration. The filtrate is taken to dryness in vacuo and the resulting oil is extracted with methylene chloride and aqueous sodium bicarbonate. The organic layer is then taken to dryness and chromatographed on silica gel to give 2-[(1,3,4,5-tetrahydro-7,8-dimethoxy-2-benzothiepin-1-yl)methoxy]ethyl chloride.

Following the procedure of Preparation 5a, but substituting the appropriate 1-haloalkyl-benzothiepin for 1-bromomethyl-7,8-dimethoxybenzoxepin the 2-[(1,3,4,5-tetrahydro-2-benzothiepin-1-yl)alkoxy]ethyl halides (in Table 5a) can be prepared.

TABLE 5a 1. 2-[(9-methoxy-8-propyl-1,3,4,5-tetrahydro-2-benzothiepin-1-yl)methoxy]ethyl chloride,
2. 2-[(9-methoxy-1,3,4,5-tetrahydro-2-benzothiepin-1-yl)methoxy]ethyl chloride,
3. 2-[(6,7-dimethoxy-1,3,4,5-tetrahydro-2-benzothiepin-1-yl)methoxy]ethyl chloride,
4. 2-[(7-ethoxy-1,2,4,5-tetrahydro-2-benzothiepin-1-yl)methoxy]ethyl chloride,
5. 2-[(7,8,9-trimethoxy-1,3,4,5-tetrahydro-2-benzothiepin-1-yl)methoxy]ethyl chloride,
6. 2-[(7-hydroxy-6-methoxy-1,3,4,5-tetrahydro-2-benzothiepin-1-yl)methoxy]ethyl chloride,
7. 2-[(8-bromo-7-methoxy-1,3,4,5-tetrahydro-2-benzothiepin-1-yl)methoxy]ethyl chloride,
8. 2-[(7-methoxy-8,9-dichloro-1,3,4,5-tetrahydro-2-benzothiepin-1-yl)methoxy]ethyl chloride,
9. 2-[(7-methoxy-8-trifluoromethyl-1,3,4,5-tetrahydro-2-benzothiepin-1-yl)methoxy]ethyl chloride,
10. 2-[(7,8-methylenedioxy-1,3,4,5-tetrahydro-2-benzothiepin-1-yl)mdthoxy]ethyl chloride,
11. 2-[(7-methoxy-5-methyl-1,3,4,5-tetrahydro-2-benzothiepin-1-yl)methoxy]ethyl chloride,
12. 2-[(7,9-dimethoxy-4,5-dimethyl-1,3,4,5-tetrahydro-2-benzothiepin-1-yl)methoxy]ethyl chloride,
13. 2-[(7,8,9-trimethoxy-4-methyl-1,3,4,5-tetrahydro-2-benzothiepin-1-yl)methoxy]ethyl chloride,
14. 2-[(9-methoxy-4-phenyl-1,3,4,5-tetrahydro-2-benzothiepin-1-yl)methoxy]ethyl chloride,
15. 2-[(7-hydroxy-5-bromo-1,3,4,5-tetrahydro-2-benzothiepin-1-yl)methoxy]ethyl chloride,
16. 2-[(7,8-dimethoxy-5,5-dimethyl-1,3,4,5-tetrahydro-2-benzothiepin-1-yl)methoxy]ethyl chloride,
17. 2-[(7,8-dimethoxy-4,4-dimethyl-1,3,4,5-tetrahydro-2-benzothiepin-1-yl)methoxy]ethyl chloride,
18. 1-(2-chloroethoxymethyl)-1,5-dihydro-7,8-dimethoxyspiro[2-benzothiepin-4(3H),1'-cyclopentane],
19. 6-(2-chloroethoxymethyl)-8,9-dipropoxy-2,3,3a,4,6,10b-hexahydro-1H-benzo[c]cyclopent[e]thiepin,
20. 2-[(4-cyclopentyl-8,9-dimethoxy-1,3,4,5-tetrahydro-2-benzothiepin-1-yl)methoxy]ethyl chloride,
21. 2-[(7,8-dihydroxy-5-propyl-1,3,4,5-tetrahydro-2-benzothiepin-1-yl)methoxy]ethyl chloride,
22. 2-[(7,8-dimethoxy-9-trifluoromethyl-1,3,4,5-tetrahydro-2-benzothiepin-1-yl)methoxy]ethyl chloride.

Similarly, from chloroethanol and the appropriate 1-chloroethylbenzothiepins of Table 1B or the 1-chloropropylbenzothiepins of Table 3, and following the procedure of preparation 5, the corresponding 2-[(1,3,4,5-tetrahydro-2-benzothiepin-1-yl)alkoxy]ethyl chlorides can be prepared.

Preparation 6:
2-[(1,3,4,5-Tetrahydro-7,8-dimethoxy-2-benzoxepin-1-yl)methoxy]ethanol A mixture of 3.67 g (12.2 mmoles) of 1-bromomethyl-7,8-dimethoxy-2-benzoxepin, 2.12 ml (12.2 mmoles) of diisopropylethylamine, and 15 ml of ethylene glycol is heated at 100° for 7 hours. The reaction mixture is then cooled and extracted with methylene chloride, then with water and finally with brine. The organic layer is filtered through $Na_2SO_4$, taken to dryness, and chromatographed on silica gel to give 3.06 g (89%) of 2-[(1,3,4,5-tetrahydro-7,8-dimethoxy-2-benzoxepin-1-yl)methoxy]ethanol: mass spectrum: $M^+$ (m/e=282).

Following the procedure of Preparation 6, but substituting the appropriate 1-halomethyl-2-benzoxepin, the 2-[(1,3,4,5-tetrahydro-2-benzoxepin-1-yl)methoxy]ethanols of Table 6 can be prepared.

TABLE 6

1. 2-[(1,3,4,5-tetrahydro-9-methoxy-8-propyl-2-benzoxepin-1-yl)methoxy]ethanol,
2. 2-[(1,3,4,5-tetrahydro-9-methoxy-2-benzoxepin-1-yl)methoxy]ethanol,
3. 2-[(1,3,4,5-tetrahydro-6,7-dimethoxy-2-benzoxepin-1-yl)methoxy]ethanol,
4. 2-[(1,3,4,5-tetrahydro-7-ethoxy-2-benzoxepin-1-yl)methoxy]ethanol,
5. 2-[(1,3,4,5-tetrahydro-7,8,9-trimethoxy-2-benzoxepin-1-yl)methoxy]ethanol,
6. 2-[(1,3,4,5-tetrahydro-7-hydroxy-6-methoxy-2-benzoxepin-1-yl)methoxy]ethanol,
7. 2-[(1,3,4,5-tetrahydro-8-bromo-7-methoxy-2-benzoxepin-1-yl)methoxy]ethanol,
8. 2-[(1,3,4,5-tetrahydro-7-methoxy-8,9-dichloro-2-benzoxepin-1-yl)methoxy]ethanol,
9. 2-[(1,3,4,5-tetrahydro-7-methoxy-8-trifluoromethyl-2-benzoxepin-1-yl)methoxy]ethanol,
10. 2-[(1,3,4,5-tetrahydro-7,8-methylenedioxy]-2-benzoxepin-1-yl)methoxy]ethanol,
11. 2-[(1,3,4,5-tetrahydro-7-methoxy-5-methyl-2-benzoxepin-1-yl)methoxy]ethanol
12. 2-[(1,3,4,5-tetrahydro-7,9-dimethoxy-4,5-dimethyl-2-benzoxepin-1-yl)methoxy]ethanol
13. 2-[(1,3,4,5-tetrahydro-7,8,9-trimethoxy-4-methyl-2-benzoxepin-1-yl)methoxy]ethanol
14. 2-[(1,3,4,5-tetrahydro-9-methoxy-4-phenyl-2-benzoxepin-1-yl)methoxy]ethanol
15. 2-[(1,3,4,5-tetrahydro-7-hydroxy-5-bromo-2-benzoxepin-1-yl)methoxy]ethanol
16. 2-[(1,3,4,5-tetrahydro-7,8-dimethoxy-5,5-dimethyl-2-benzoxepin-1-yl)methoxy]ethanol
17. 2-[(1,3,4,5-tetrahydro-7,8-dimethoxy-4,4-dimethyl-2-benzoxepin-1-yl)methoxy]ethanol
18. 2-[[1,5-dihydro-7,8-dimethoxyspiro[2-benzoxepin-4(3H)-1'-cyclopentane]-1-yl]methoxy]ethanol
19. 2-[(8,9-dipropoxy-2,3,3a,4,6,10b-hexahydro-1H-benzo[c]cyclpent[e]oxepin-6-yl)methoxy]ethanol
20. 2-[(1,3,4,5-tetrahydro-4-cyclopentyl-8,9-dimethoxy-2-benzoxepin-1-yl)methoxy]ethanol
21. 2-[(1,3,4,5-tetrahydro-7,8-dihydroxy-5-n propyl-2-benzoxepin-1-yl)methoxy]ethanol
22. 2-[(7,8-dimethoxy-9-trifluoromethyl-1,3,4,5-tetrahydro-2-benzoxepin-1-yl)methoxy]ethanol Similarly, from ethylene glycol and the appropriate 1-chloroethyl benzoxepins of Table 1B or the 1-chloropropylbenzoxepins of Table 3a, and following the procedure of preparation 5, the analogous 2-[(1,3,4,5-tetrahydro-2-benzoxepin-1-yl)alkoxy]ethanols can be prepared.

Preparation 6A:
2-[(1,3,4,5-tetrahydro-7,8-dimethoxy-2-benzothiepin-1-yl)methoxy]ethanol A mixture of 1-bromomethyl-7,8-dimethoxy-2-benzothiepin, diisopropylethylamine, and ethylene glycol is heated at 30° to 100° C. for 5-50 hours. The reaction mixture is then cooled, diluted with methylene chloride and extracted with water followed by brine. The organic layer is filtered through $Na_2SO_4$, taken to dryness, and chromatographed on silica gel to give 2-[(1,3,4,5-tetrahydro-7,8-dimethoxy-2-benzothiepin-1-yl)methoxy]ethanol.

Following the procedure of Preparation 6A, but substituting the appropriate 1-halomethyl-2-benzothiepin the 2-[(1,3,4,5-tetrahydro-2-benzothiepin-1-yl)methoxy]ethanols of Table 6A can be prepared.

TABLE 6A 1. 2-[(1,3,4,5-tetrahydro-8-propyl-9-methoxy-2-benzothiepin-1-yl)methoxy]ethanol
2. 2-[(1,3,4,5-tetrahydro-9-methoxy-2-benzothiepin-1-yl)methoxy]ethanol
3. 2-[(1,3,4,5-tetrahydro-6,7-dimethoxy-2-benzothiepin-1-yl)methoxy]ethanol
4. 2-[(1,3,4,5-tetrahydro-7-ethoxy-2-benzothiepin-1-yl)methoxy]ethanol
5. 2-[(1,3,4,5-tetrahydro-7,8,9-trimethoxy-2-benzothiepin-1-yl)methoxy]ethanol
6. 2-[(1,3,4,5-tetrahydro-7-hydroxy-6-methoxy-2-benzothiepin-1-yl)methoxy]ethanol
7. 2-[(1,3,4,5-tetrahydro-8-bromo-7-methoxy-2-benzothiepin-1-yl)methoxy]ethanol
8. 2-[(1,3,4,5-tetrahydro-7-methoxy-8,9-dichloro-2-benzothiepin-1-yl)methoxy]ethanol
9. 2-[(1,3,4,5-tetrahydro-7-methoxy-8-trifluoromethyl)-2-benzothiepin-1-yl)methoxy]ethanol
10. 2-[(1,3,4,5-tetrahydro-7,8-methylenedioxy-2-benzothiepin-1-yl)methoxy]ethanol
11. 1-[(1,3,4,5-tetrahydro-7-methoxy-5-methyl-2-benzothiepin-1-yl)methoxy]ethanol
12. 2-[(1,3,4,5-tetrahydro-7,9-dimethoxy-4,5-dimethyl-2-benzothiepin-1-yl)methoxy]ethanol
13. 2-[(1,3,4,5-tetrahydro-7,8,9-trimethoxy-4-methyl-2-benzothiepin-1-yl)methoxy]ethanol
14. 2-[(1,3,4,5-tetrahydro-9-methoxy-4-phenyl-2-benzothiepin-1-yl)methoxy]ethanol
15. 2-[(1,3,4,5-tetrahydro-7-hydroxy-5-bromo-2-benzothiepin-1-yl)methoxy]ethanol
16. 2-[(1,3,4,5-tetrahydro-7,8-dimethoxy-5,5-dimethyl-2-benzothiepin-1-yl)methoxy]ethanol
17. 2-[(1,3,4,5-tetrahydro-7,8-dimethoxy-4,4-dimethyl-2-benzothiepin-1-yl)methoxy]ethanol
18. 2-[1,5-dihydro-7,8-dimethoxyspiro[2-benzothiepin-4(3H)-1'-cyclopentane]-1-yl]methoxyethanol
19. 2-[(8,9-dipropoxy-2,3,3a,4,6,10b-hexahydro-1H-benzo[c]cyclopent[e]thiepin-6-yl)methoxy]ethanol
20. 2-[(1,3,4,5-tetrahydro-4-cyclopentyl-8,9-dimethoxy-2-benzothiepin-1-yl)methoxy]ethanol
21. 2-[(1,3,4,5-tetrahydro-7,8-dihydroxy-5-propyl-2-benzothiepin-1-yl)methoxy]ethanol
22. 2-[(7,8-dimethoxy-9-trifluoromethyl-1,3,4,5-tetrahydro-2-benzothiepin-1-yl)methoxy]ethanol Similarly, from ethylene glycol and the appropriate 1-chloroethyl-2-benzothiepins or the 1-chloropropyl-2-benzothiepins of Table 4A, the analogous 2-[(1,3,4,5-tetrahydro-2-benzothiepin-1-yl)alkoxy]ethanols can be prepared with the procedure of Preparation 6A.

Preparation 7: 2-[(1,3,4,5-tetrahydro-7,8-dimethoxy-2-benzoxepin-1-yl)methoxy]ethyl 4-nitrobenzene sulfonate To a mixture of 3.00 g (10.6 mmoles) of 2-[(1,3,4,5-tetrahydro-7,8-dimethoxy-2-benzoxepin-1-yl)methoxy]ethanol and 1.63 ml (11.7 mmoles) of triethylamine is added 2.59 g (11.7 mmoles) of p-nitrobenzenesulfonyl chloride. The reaction mixture is stirred at room temperature for 1 hour and then heated at 50° for 30 minutes. To this is added an additional 0.5 g of p-nitrobenzenesulfonyl chloride and 0.5 ml of triethylamine. After stirring at room temperature for 30 minutes, the reaction mixture is extracted with aqueous sodium bicarbonate and brine. The organic layer is filtered through sodium sulfate and taken to dryness. The residue is chromatographed on silica gel using 1% methanol methylene chloride as eluant to give 1.56 g (32%) 2-[(1,3,4,5-tetrahydro-7,8-dimethoxy-2-benzoxepin-1-yl)methoxy]ethyl 4-nitrobenzene sulfonate. The nmr spectrum was consistent with the assigned structure.

Utilizing the procedure of Preparation 7, but substituting the appropriate 2-[(1,3,4,5-tetrahydro-2-benzoxepin-1-yl)methoxy]ethanol, the 2-[(1,3,4,5-tetrahydro-2-benzoxepin-1-yl)methoxy]ethyl benzenesulfonates of Table 7 can be prepared.

TABLE 7

1. 2-[(1,3,4,5-tetrahydro-9-methoxy-8-propyl-2-benzoxepin-1-yl)methoxy]ethyl 4-nitrobenzenesulfonate
2. 2-[(1,3,4,5-tetrahydro-9-methoxy-2-benzoxepin-1-yl)methoxy]ethyl 4-nitrobenzenesulfonate
3. 2-[(1,3,4,5-tetrahydro-6,7-dimethoxy-2-benzoxepin-1-yl)methoxy]ethyl 4-methoxybenzenesulfonate
4. 2-[(1,3,4,5-tetrahydro-7-ethoxy-2-benzoxepin-1-yl)methoxy]ethyl 4-ethylbenzenesulfonate
5. 2-[(1,3,4,5-tetrahydro-7,8,9-trimethoxy-2-benzoxepin-1-yl)methoxy]ethyl 4-nitrobenzene-sulfonate
6. 2-[(1,3,4,5-tetrahydro-7-hydroxy-6-methoxy-2-benzoxepin-1-yl)methoxy]ethyl 4-chlorobenzenesulfonate
7. 2-[(1,3,4,5-tetrahydro-8-bromo-7-methoxy-2-benzoxepin-1-yl)methoxy]ethyl 4-nitrobenzenesulfonate
8. 2-[(1,3,4,5-tetrahydro-7-methoxy-8,9-dichloro-2-benzoxepin-1-yl)methoxy]ethyl 4-nitrobenzenesulfonate
9. 2-[(1,3,4,5-tetrahydro-7-methoxy-8-trifluoromethyl)-2-benzoxepin-1-yl)methoxy]ethyl 4-bromobenzenesulfonate
10. 2-[(1,3,4,5-tetrahydro-7,8-methylenedioxy-2-benzoxepin-1-yl)methoxy]ethyl 4-nitrobenzenesulfonate
11. 2-[(1,3,4,5-tetrahydro-7-methoxy-5-methyl-2-benzoxepin-1-yl)methoxy]ethyl 2-methylbenzenesulfonate
12. 2-[(1,3,4,5-tetrahydro-7,9-dimethoxy-4,5-dimethoxy-2-benzoxepin-1-yl)methoxy]ethyl 4-nitrobenzenesulfonate
13. 2-[(1,3,4,5-tetrahydro-7,8,9-trimethoxy-4-methyl-2-benzoxepin-1-yl)methoxy]ethyl 4-nitrobenzenesulfonate
14. 2-[(1,3,4,5-tetrahydro-9-methoxy-4-phenyl-2-benzoxepin-1-yl)methoxy]ethyl 3-trifluoromethylbenzenesulfonate
15. 2-[(1,3,4,5-tetrahydro-7-hydroxy-5-bromo-2-benzoxepin-1-yl)methoxy]ethyl 4-nitrobenzenesulfonate
16. 2-[(1,3,4,5-tetrahydro-7,8-dimethoxy-5,5-dimethyl-2-benzoxepin-1-yl)methoxy]ethyl 4-nitrobenzenesulfonate
17. 2-[(1,3,4,5-tetrahydro-7,8-dimethoxy-4,4-dimethyl-2-benzoxepin-1-yl)methoxy]ethyl 3-trifluoromethylbenzenesulfonate
18. 2-[[1,5-dihydro-7,8-dimethoxyspiro[2-benzoxepin-4(3H)-1'-cyclopentane]-1-yl]methoxy]ethyl 4-nitrobenzenesulfonate
19. 2-[(8,9-dipropoxy-2,3,3a,4,6,10b-hexahydro-1H-benzo[c]cyclopent[e]oxepin-6-yl)methoxy]ethyl 2-ethylbenzenesulfonate
20. 2-[(1,3,4,5-tetrahydro-4-cyclopentyl-8,9-dimethoxy-2-benzoxepin-1-yl)methoxy]ethyl 4-nitrobenzenesulfonate
21. 2-[(1,3,4,5-tetrahydro-7,8-dihydroxy-5-n-propyl-2-benzoxepin-1-yl)methoxy]ethyl 4-nitrobenzenesulfonate
22. 2-[(1,3,4,5-tetrahydro-7,8-dimethoxy-9-trifluoromethyl-2-benzoxepin-1-yl)methoxy]ethyl 3-nitrobenzenesulfonate Similarly, from the appropriate 2-[(1,3,4,5-tetrahydro-2-benzoxepin-1-yl)ethoxy]ethanol and the appropriately substituted benzenesulfonyl chloride the corresponding 2-[(1,3,4,5-tetrahydro-2-benzoxepin-1-yl)ethoxy]ethyl benzenesulfonates can be prepared using the procedure of Preparation 7.

Preparation 7A:

2-[(1,3,4,5-tetrahydro-7,8-dimethoxy-2-benzothiepin-1-yl)methoxy]ethyl 4-nitrobenzenesulfonate To a mixture of 2-[(1,3,4,5-tetrahydro-7,8-dimethoxy-2-benzothiepin-1-yl)methoxy]ethanol and triethylamine is added p-nitrobenzenesulfonyl chloride. The reaction mixture is stirred at room temperature for 30 minutes. The reaction mixture is then extracted with aqueous sodium bicarbonate and brine. The organic layer is filtered through sodium sulfate and taken to dryness. The residue is chromatographed on silica gel to give 2-[(1,3,4,5-tetrahydro-7,8-dimethoxy-2-benzothiepin-1-yl)methoxy]ethyl 4-nitrobenzenesulfonate.

Utilizing the procedure of Preparation 7A but substituting the appropriate 2-[(1,3,4,5-tetrahydro-2-benzothiepin-1-yl)methoxy]ethanol, the 2-[(1,3,4,5-tetrahydro-2-benzothiepin-1-yl)methoxy]ethyl benzenesulfonates of Table 7A can be prepared.

TABLE 7A 1. 2-[(1,3,4,5-tetrahydro-9-methoxy-7-propyl-2-benzothiepin-1-yl)methoxy]ethyl 4-nitrobenzenesulfonate
2. 2-[(1,3,4,5-tetrahydro-9-methoxy-2-benzothiepin-1-yl)methoxy]ethyl 4-nitrobenzenesulfonate
3. 2-[(1,3,4,5-tetrahydro-6,7-dimethoxy-2-benzothiepin-1-yl)methoxy]ethyl 4-methoxybenzenesulfonate
4. 2-[(1,3,4,5-tetrahydro-7-ethoxy-2-benzothiepin-1-yl)methoxy]ethyl 4-ethylbenzenesulfonate
5. 2-[(1,3,4,5-tetrahydro-7,8,9-trimethoxy-2-benzothiepin-1-yl)methoxy]ethyl 4-nitrobenzenesulfonate
6. 2-[(1,3,4,5-tetrahydro-7-hydroxy-6-methoxy-2-benzothiepin-1-yl)methoxy]ethyl 4-chlorobenzenesulfonate
7. 2-[(1,3,4,5-tetrahydro-8-bromo-7-methoxy-2-benzothiepin-1-yl)methoxy]ethyl 4-nitrobenzenesulfonate
8. 2-[(1,3,4,5-tetrahydro-7-methoxy-8,9-dichloro-2-benzothiepin-1-yl)methoxy]ethyl 4-nitrobenzenesulfonate
9. 2-[(1,3,4,5-tetrahydro-7-methoxy-8-trifluoromethyl)-2-benzothiepin-1-yl)methoxy]ethyl 4-bromobenzenesulfonate
10. 2-[(1,3,4,5-tetrahydro-7,8-methylenedioxy-2-benzothiepin-1-yl)methoxy]ethyl 4-nitrobenzenesulfonate 11. 2-[(1,3,4,5-tetrahydro-7-methoxy-5-methyl-2-benzothiepin-1-yl)methoxy]ethyl 2-methylbenzenesulfonate
12. 2-[(1,3,4,5-tetrahydro-7,9-dimethoxy-4,5-dimethoxy-2-benzothiepin-1-yl)methoxy]ethyl 4-nitrobenzenesulfonate
13. 2-[(1,3,4,5-tetrahydro-7,8,9-trimethoxy-4-methyl-2-benzothiepin-1-yl)methoxy]ethyl 4-nitrobenzenesulfonate
14. 2-[(1,3,4,5-tetrahydro-9-methoxy-4-phenyl-2-benzothiepin-1-yl)methoxy]ethyl 3-trifluoromethylbenzenesulfonate
15. 2-[(1,3,4,5-tetrahydro-7-hydroxy-5-bromo-2-benzothiepin-1-yl)methoxy]ethyl 4-nitrobenzenesulfonate
16. 2-[(1,3,4,5-tetrahydro-7,8-dimethoxy-5,5-dimethyl-2-benzothiepin-1-yl)methoxy]ethyl 4-nitrobenzenesulfonate
17. 2-[(1,3,4,5-tetrahydro-7,8-dimethoxy-4,4-dimethyl-2-benzothiepin-1-yl)methoxy]ethyl 3-trifluoromethylbenzenesulfonate
18. 2-[[1,5-dihydro-7,8-dimethoxyspiro[2-benzothiepin-4(3H)-1'-cyclopentane]-1-yl]methoxy]ethyl 4-nitrobenzenesulfonate
19. 2-[(8,9-dipropoxy-2,3,3a,4,6,10b-hexahydro-1H-benzo[c]cyclopent[e]thiepin-6-yl)methoxy]ethyl 2-ethylbenzenesulfonate
20. 2-[(1,3,4,5-tetrahydro-4-cyclopentyl-8,9-dimethoxy-2-benzothiepin-1-yl)methoxy]ethyl 4-nitrobenzenesulfonate
21. 2-[(1,3,4,5-tetrahydro-7,8-dihydroxy-5-n-propyl-2-benzothiepin-1-yl)methoxy]ethyl 4-nitrobenzenesulfonate
22. 2-[(1,3,4,5-tetrahydro-7,8-dimethoxy-9-trifluoromethyl-2-benzothiepin-1-yl)methoxy]ethyl 3-nitrobenzenesulfonate Similarly, following the procedure of Preparation 7A, from the corresponding 2-[(1,3,4,5-tetrahydro-2-benzothiepin-1-yl)ethoxy] and propoxy]ethanols, the corresponding benzenesulfonates can be prepared.

Preparation 8:
2-[(1-methyl-7,8-dimethoxyisochroman-1-yl)methoxy]ethanol and derivatives.

Ethyl pyruvate (1.00 g, 0.0086 m), 3,4-dimethoxyphenylethanol (1.57 g, 0.0086 m), and, 1 ml of BF3 etherate are stirred at 25° C. in 20 ml of nitromethane for 45 minutes. The mixture is dissolved in methylene chloride and extracted with aqueous sodium bicarbonate. The organic phase is dried (sodium sulfate), concentrated, and chromatographed on silica gel to give 1.4 g of 6,7-dimethoxy-1-methyl-1-carboethoxyisochroman. A 0.5 g sample of this is dissolved in ether and treated with 100 mg of LAH. After 10 minutes, the mixture is quenched with ethyl acetate and partitioned between 1 N aqueous sodium hydroxide and CH2Cl2. The organic phase yields 0.34 g of 6,7-dimethoxy-1-methyl-1-hydroxymethylisochroman. This is dissolved in THF and treated sequentially with sodium hydride and then o-tetrahydropyranyl chloroethanol. The adduct, upon treatment with acid and water, yields 2-[(7,8-dimethoxy-1-methyl-isochroman-1-yl)methoxy]ethanol. In the manner of Preparation 7, this can be converted to its benzenesulfonates

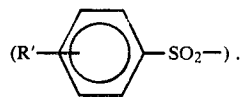

Furthermore, 2-[(1-methylisochroman-1-yl)methoxy]ethanols, with various substituents on the isochroman ring, can be prepared by using the appropriate phenyl ethanols whose substituents, $R_1$-$R_5$ (vide supra), are analogous to those substituents of the isochromans of Table 3.

From these compounds, the corresponding substituted benzenesulfonates can be prepared.

Furthermore, by reacting appropriate phenyl ethanols with various substituted 2-keto esters, the $R_8$ substituents of the isochroman ring (vide supra) can be varied and the disclosed $R_8$ substituents can thus be incorporated in the ring system.

Furthermore, various 1-hydroxymethylisochromans can be first treated with tetrahydropyranyl chloroethoxyethanol and then with acid and water to yield the corresponding 2-[2-((isochroman-1-yl)methoxy)ethoxy]ethanol.

Preparation 8A:
2-[(7,8-dimethyl-3,4-dyhydro-1H-2-benzothiopyran-1-yl)methoxy]ethanol Ethyl pyruvate, 3,4-dimethoxyphenyl ethanethiol, and BF3 etherate are stirred in nitromethane. The mixture is partitioned with methylene chloride and aqueous sodium bicarbonate. The organic phase is dried over sodium sulfate, concentrated, and chromatographed. The resultant benzothiopyran is dissolved in ether and treated with lithium aluminum hydride. The mixture is partitioned between aqueous sodium hydroxide and methylene chloride. The organic phase yields the corresponding alcohol. This can be dissolved in THF and treated sequentially with sodium hydroxide and then O-tetrahydropyranyl ether of chloroethanol. The adduct upon treatment with acid and water, yields 2-[(7,8-dimethoxy-3,4-dihydro-1H-2-benzothiopyran-1-yl)methoxy]ethanol. In the manner of example 7A, this can be converted to its p-nitrobenzenesulfonate.

Furthermore, 2-[(3,4-dihydro-1H-2-benzothiopyran-1-yl)methoxy]ethanols with various substituents on the thiopyran ring can be prepared by using the appropriate phenyl ethanols whose substituents, $R_1$-$R_5$ (vide supra), are analogous to those substituents of the thiopyrans of Table 2A. These alcohols can then be converted to their corresponding benzenesulfonates following the procedure of Preparation 7A and the benzenesulfonyl chlorides used to prepare compounds of Table 7A.

Examples 1 through 19: Benzoxepins and benzothiepins

A 1-bromoethylbenzoxepin prepared as in Preparation 1 is stirred in ethylene glycol with 1.0 to 2.0 equivalents of $HNR_9R_{10}$. An excess of triethylamine is added. After the reaction is complete, the mixture is partitioned between aqueous $K_2CO_3$ or $Na_2CO_3$ and $CH_2Cl_2$. The organic phase is dried over $Na_2SO_4$ and concentrated. The residue is chromatographed on silica gel. The product is either crystallized or converted to its salt. The salt is formed by treating a solution of the compound with an appropriate acid in a suitable solvent.

1-(4-fluorophenyl)-4-[(1,3,4,5-tetrahydro-7,8-dimethoxy-2-benzoxepin-1-yl)methyl]-piperazine A mixture of 3.50 g (0.0116 moles) of 1-bromomethyl-7,8-dimethoxy-2-benzoxepin, 2.51 g (0.0139 moles) of p-fluorophenyl piperazine, 1.94 ml (0.0139 moles) of triethyl amine, and 125 ml of ethylene glycol is heated under $N_2$ at 100° for 8 hours. After cooling, the reaction mixture is extracted with $CH_2Cl_2$, aq. $NaHCO_3$, and $H_2O$. The organic layer is filtered through $Na_2SO_4$ and taken to dryness. The crude reaction mixture is then chromatographed on silica gel using 50% Skellysol-ve ® B as eluant to give 0.60 g (13%) of product which is then crystallized from methylenechloride/Skellysol-ve ® B to yield 1-(4-fluorophenyl)-4-[(1,3,4,5-tetrahydro-7,8-dimethoxy-2-benzoxepin-1-yl)methyl]-piperazine, m.p. 135°–136° C.

Analysis Calcd. for: $C_{23}H_{29}FN_2O_3$: C, 68.97; H, 7.30; N, 7.00. Found: C, 68.68; H, 7.12; N, 6.82.

The following 1-methyl substituted-1,3,4,5-tetrahydro-2-benzoxepines are prepared according to the procedure of Example 1, in some cases with minor variations therefrom. The nmr spectra are consistent with the assigned structures.

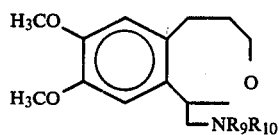

| Ex. | HNR9R10 | (C.°/Hrs) | Miscellaneous | M.P. | Anal. (found) | Name |
|---|---|---|---|---|---|---|
| 1. | HN(piperazine)N-phenyl-F | 100/6 | | 135–136 | C=68.68; H=7.12; N=6.82 | 1-(4-fluorophenyl)-4-[1,3,4,5-tetrahydro-7,8-dimethoxy-2-benzoxepin-1-yl)methyl]-piperazine |
| 2. | HN(piperazine)N-phenyl-OCH3 (ortho) | 90/1.5 | | 162–166[b] | N=6.05; C=62.86; H=7.30 | 1-(2-methoxyphenyl)-4-[(1,3,4,5-tetrahydro-7,8-dimethoxy-2-benzoepin-1-yl)methyl]-monohydrochloride hemihydrate |
| 3. | H2NCH2CH2-phenyl-OCH3, OCH3 | 85/1.5; and 20/18 | 1. No solvent used. 2. Excess HNR9R10 used as base. | 75–85[c] | C=60.73; H=7.17; N=3.66 | N-[2-(3,4-dimethoxyphenyl)ethyl]-1,3,4,5-tetrahydro-7,8-dimethoxy-2-benzoxepin-1-yl-methanamine monohydrochloride monohydrate |
| 4. | HN(piperazine)N-pyridinyl | 100/7.75 | 1. DMF used as solvent. 2. Diisopropyl-ethyl-amine used as base. | 196–199[b] | C=61.42; H=7.01; N=9.69 | 1-(2-pyridinyl)-4-[(1,3,4,5-tetrahydro-7,8-dimethoxy-2-benzoxepin-1-yl)methyl]-piperazine monochloride hemihydrate |
| 5. | HN(piperazine)N-phenyl-OCH3 | 105/2; | 1. Ethylene glycol monoethylether | | C=61.85; H=7.32; 5.98 HN | 1-(4-methoxyphenyl)-4-[(1,3,4,5-tetrahydro-7,8-dimethoxy-2-benzoxepin-1-yl)methyl]-piperazine monohydrochloride monohydrochloride monohydrate |
| 6. | HN-piperidine-OH, -phenyl-CF3 | 1. Reflux 20 2. 100/4; 20/16 | 1. THF used as solvent for first 20 hrs.; then replaced with ethylene glycol | 172–173[d] | C=55.61; H=5.60; n=2.47 | 1-[(1,3,4,5-tetrahydro-7,8-dimethoxy-2-benzoxepin-1-yl)methyl]-4-[3-(trifluoromethyl)phenyl]-4-piperidinol monohydrobromide |
| 7. | HN(piperazine)N-phenyl | 95/5.5 | 1. DMF used as solvent. 2.Diisopropylethyl-amine used as base. | 106–108 | C=71.81; H=8.17; N=7.19 | 1-phenyl-4-[(1,3,4,5-tetrahydro-7,8-dimethoxy-2-benzoxepin-1-yl)-methyl]-piperazine |
| 8. | HN N | | 1. Toluene used as solvent 2. Excess amine used as base. | 139–142[a] | | 1-(2-methylphenyl)-4-[(1,3,4,5-tetrahydro-7,8-dimethoxy-2-benzoxepin-1-yl)methyl]piperazine |
| 9. | H—N | | | | C=62.68; H=7.25; N=3.00 | 1,2,3,4-tetrahydro-6,7-dimethoxy-2-[(1,3,4,5-tetrahydro-7,8-dimethoxy-2-benzoxepin-1-yl)methyl]-isoquinoline, monohydrochloride hemihydrate |

Example 10A:

1-[2-[(1,3,4,5-tetrahydro-7,8-dimethoxy-2-benzoxepin-1-yl)]ethyl]-4-(3-chlorophenyl)piperazine A mixture of 2.00 g (7.39 mmol) of 2-[(1,3,4,5-tetrahydro-7,8-dimethoxy-2-benzoxepin-1-yl)]ethyl chloride and 2.8 g (14.5 mmol) of 1-(3-chlorophenyl)piperazine is stirred at 85° for 36 hours in 1 ml of ethylene glycol and 10 ml of toluene. Excess toluene is added and the solids are removed by filtration from the warm solution. The organic phase is concentrated. The product was recrystallized from $CH_2Cl_2$ and toluene to give 1.09 g of product, m.p. 125°–126°.

Analysis Calcd. for: $C_{24}H_{31}ClN_2O_3$: C, 66.88; H, 7.25; N, 6.50 Found: C, 66.68; H, 7.49; N, 6.31

The following 1-ethyl substituted -1,3,4,5-tetrahydro-2-benzoxepins are prepared according to the procedure of Example 10a, in some cases with minor variations therefrom. The nmr spectra are consistent with the assigned structures.

Core structure: 7,8-dimethoxy-1,3,4,5-tetrahydro-2-benzoxepin with –(CH$_2$)$_2$–NR$_9$R$_{10}$ substituent at position 1.

| Ex. | HNR$_9$R$_{10}$ | C.°/Hrs. | M.P.(°C.) | Anal. (found) | Name |
|---|---|---|---|---|---|
| 10b | 1-(2-methoxyphenyl)piperazine | 80/22 | 146°–149° | C, 63.79; H, 7.73; N, 5.90 | 1-[2-[(1,3,4,5-tetrahydro-7,8-dimethoxy-2-benzoxepin-1-yl)]ethyl]-4-(2-methoxyphenyl)-piperazine, monohydrochloride hemihydrate |
| 10c | 1-(4-fluorophenyl)piperazine | 88/90 | 115.0 | C, 69.42; H, 7.79; N, 6.70 | 1-[2-[1,3,4,5-tetrahydro-7,8-dimethoxy-2-benzoxepin-1-yl) ethyl]-4-(4-fluorophenyl)piperazine |
| 10d | 3,4-dimethoxyphenethylamine | 85/27 | 60°–70° | C, 61.50; H, 7.60; N, 3.06; Cl, 7.40 | N-[2- (1,3,4,5-tetrahydro-7,8-dimethoxy-2-benzoxepin-1-yl)ethyl]-N-[2-(3,4-dimethoxyphenyl)ethyl]amine, monohydrochloride monohydrate |
| 10e | 1-(4-chlorophenyl)piperazine | 90/26 | 154.5°–155° | C, 66.77; H, 7.23; N, 6.24 | 1-[2- (1,3,4,5-tetrahydro-7,8-dimethoxy-2-benzoxepin-1-yl) ethyl]-4-(4-chlorophenyl)piperazine |
| 10f | 1,2,3,6-tetrahydro-4-(4-chlorophenyl)pyridine | 90/48 | 121.0°–122° | C, 69.92; H, 6.96; N, 3.08 | 1-[2- (1,3,4,5-tetrahydro-7,8-dimethoxy-2-benzoxepin-1-yl)ethyl]-1,2,3,6-tetrahydro-4-(4-chlorophenyl)-pyridine |
| 10g | 1-(2-methylphenyl)piperazine | 90/48 | 86.5°–87.0° | C, 72.76; H, 8.31; N, 6.76 | 1-[2-[(1,3,4,5-tetrahydro-7,8-dimethoxy-2-benzoxepin-1-yl)]ethyl]-4-(2-methylphenyl)piperazine |
| 10h | 4-(2,3-dihydro-2-oxo-1H-benzimidazol-1-yl)piperidine | 90/30 | 109°–112° |  | 1-[2-[(1,3,4,5- tetrahydro-7,8-dimethoxy-2-benzoxepin-1-yl)ethyl]-4-(2,3-dihydro-2-oxo-1H-benzimidazol-1-yl)-piperidine |
| 10i | 1-(2-pyridyl)piperazine | 95/27 | 136.5°–137.5° | C, 69.03; H, 7.61; N, 10.56 | 1-[2-[(1,3,4,5-tetrahydro-7,8-dimethoxy-2-benzoxepin-1-yl)]ethyl]-4-(2-pyridyl)-piperazine | a - monohydrochloride hemihydrate
b - monohydrochloride monohydrate

Example 11

Following the procedure used in Examples 1 through 10, but substituting the appropriate 1 haloalkylbenzoxepin, the following compounds of formula 1 can be made (Table 8).

TABLE 8

Structure: substituted benzene with R₁', R₁'', R₁''', R₁'''', R₁''''' substituents and a side chain —C(R₂)(R₃)—C(R₄)(R₅)—O—C(R₆)(R₇)(R₈)—(CH₂)ₙNR₉R₁₀

| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | H | propyl | —OCH₃ | H | H | H | H | H | H | H | 1 | NH(CH₂)₂—(2,4-dichlorophenyl) |
| H | H | H | —OCH₃ | H | H | H | H | H | H | H | 1 | N-piperazinyl-(4-chlorophenyl) |
| OCH₃ | —OCH₃ | H | H | H | H | H | H | H | H | H | 1 | N(CH₂)(CH₂)-(3,4-dimethylphenyl) ring |
| H | OH | H | H | H | Br | H | H | H | H | H | 4 | N(CH₂)(CH₂)-(3,4-dimethoxyphenyl) ring |
| H | OCH₃ | OCH₃ | H | CH₃ | CH₃ | H | H | H | H | H | 5 | NH(CH₂)₂—(2,4-dichlorophenyl) |
| H | OCH₃ | OCH₃ | H | H | H | CH₃ | CH₃ | H | H | H | 5 | N-piperazinyl-(3-bromophenyl) |

TABLE 8-continued
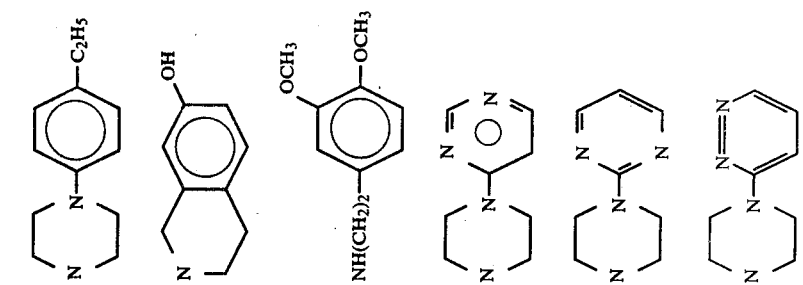
| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | $OCH_3$ | $OCH_3$ | H | H | H | * | | H | H | H | 5 | |
| H | $OC_3H_7$ | $OC_3H_7$ | H | * | H | | | H | H | H | 5 | |
| H | H | $OCH_3$ | $OCH_3$ | H | H | H | H | H | H | H | 2 | |
| H | OH | OH | H | $C_3H_7$ | H | H | H | H | H | H | 2 | |
| H | $OCH_3$ | $OCH_3$ | $CF_3$ | H | H | H | H | H | H | H | 1 | |
| H | —$OCH_3$ | —$OCH_3$ | H | H | H | H | H | H | H | H | 2 | |
| H | —$OCH_3$ | —$OCH_3$ | H | H | H | H | H | H | H | H | 2 | |
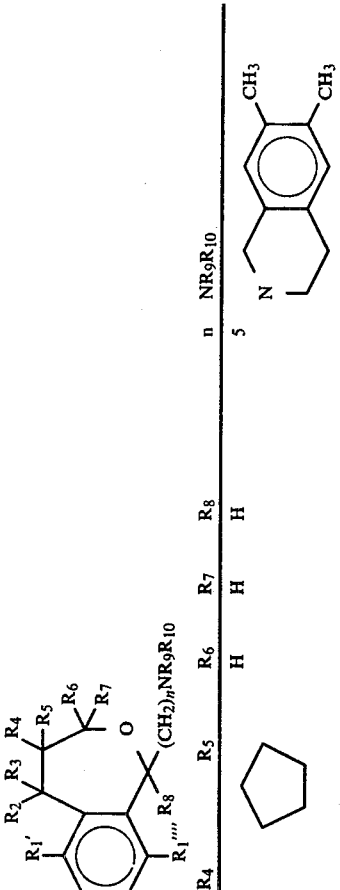

TABLE 8-continued
| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | —OCH$_3$ | —OCH$_3$ | H | CH$_3$ | —CH$_3$ | H | H | H | H | H | 2 | 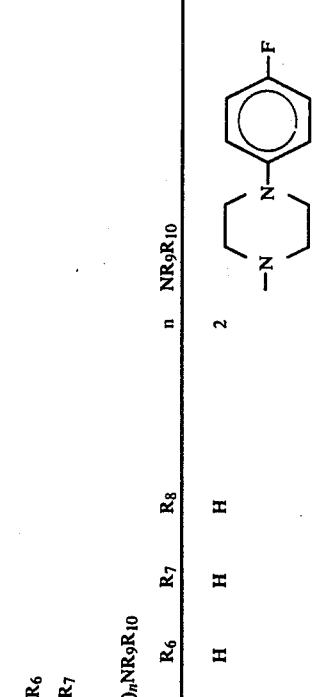 |
| H | OC$_2$H$_5$ | H | H | H | H | H | H | H | H | H | 1 | 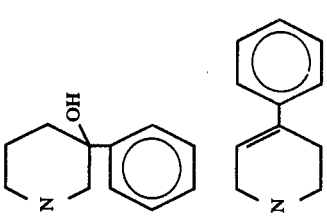 |
| H | OCH$_3$ | OCH$_3$ | OCH$_3$ | H | H | H | H | H | H | H | 1 | 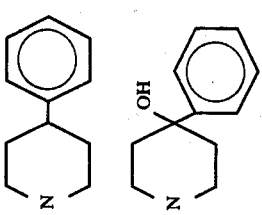 |
| —OCH$_3$ | —OH | H | H | H | H | H | H | H | H | H | 1 | 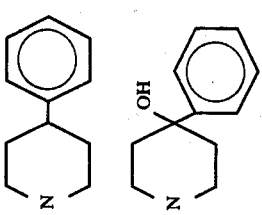 |
| H | —OCH$_3$ | Br | H | H | H | H | H | H | H | H | 1 | 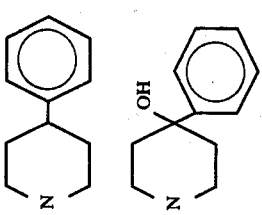 |
| H | —OCH$_3$ | Cl | Cl | H | H | H | H | H | H | H | 1 | 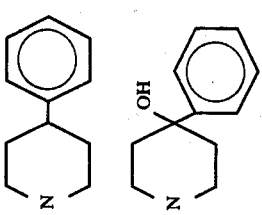 |

TABLE 8-continued
| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | —OCH$_3$ | —CF$_3$ | H | H | H | H | H | H | H | H | 2 | 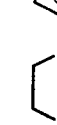 |
| H | H | —O—CH$_2$—O— | H | H | H | H | H | H | H | H | 3 | 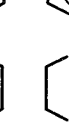 |
| H | OCH$_3$ | H | H | CH$_3$ | H | H | H | H | H | H | 3 | 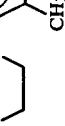 |
| H | OCH$_3$ | OCH$_3$ | OCH$_3$ | CH$_3$ | H | CH$_3$ | H | H | H | H | 3 | |
| H | OCH$_3$ | OCH$_3$ | OCH$_3$ | H | H | H | CH$_3$ | H | H | H | 3 |  |
| H | OCH$_3$ | H | OCH$_3$ | H | H | H | H | H | H | H | 4 |  |
| H | H | H | OCH$_3$ | H | H | H | C$_6$H$_5$ | H | H | H | 4 | |

TABLE 8-continued

Structure: benzene ring with substituents R1', R1'', R1''', R1'''', and side chain -C(R2)(R3)-C(R4)(R5)-C(R6)(R7)(R8)-O-(CH2)n-NR9R10

| R1' | R1'' | R1''' | R1'''' | R2 | R3 | R4 | R5 | R6 | R7 | R8 | n | NR9R10 |
|---|---|---|---|---|---|---|---|---|---|---|---|---|
| H | OCH3 | OCH3 | H | H | H | —CH3 | —CH3 | H | H | H | 2 | 4-fluorophenyl-piperazinyl |
| H | OCH3 | OCH3 | H | H | H | H | H | CH3 | CH3 | H | 2 | 4-fluorophenyl-piperazinyl |
| H | OCH3 | OCH3 | H | CH3 | CH3 | H | H | H | H | H | 2 | 2-methoxyphenyl-piperazinyl |
| H | OCH3 | OCH3 | H | H | H | H | CH3 | H | H | H | 2 | 2-methoxyphenyl-piperazinyl |
| H | —O—CH2—O— | | H | H | H | CH3 | H | H | H | H | 2 | 2-methoxyphenyl-piperazinyl |
| H | —OCH3 | —OCH3 | H | CH3 | CH3 | H | H | H | CH3 | H | 2 | 2-methoxyphenyl-piperazinyl |
| H | | | H | | | H | H | H | H | H | 2 | 2-methylphenyl-piperazinyl |

TABLE 8-continued
| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | OCH₃ | OCH₃ | H | H | H | CH₃ | CH₃ | H | H | H | 2 | 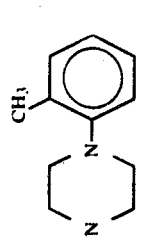 |
| H | OCH₃ | OCH₃ | H | H | H | H | H | CH₃ | CH₃ | H | 2 | 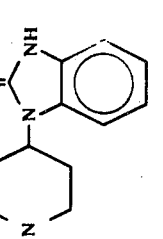 |
| H | OCH₃ | OCH₃ | H | CH₃ | CH₃ | H | H | H | H | H | 2 | 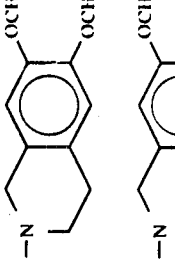 |
| H | OCH₃ | OCH₃ | H | CH₃ | CH₃ | H | H | H | H | H | 2 | 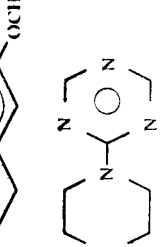 |
| H | OCH₃ | OCH₃ | H | H | H | H | H | H | H | H | 2 |  |
| H | OCH₃ | OCH₃ | H | CH₃ | CH₃ | H | H | H | H | H | 2 |  |

TABLE 8-continued

| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | OCH₃ | OCH₃ | H | H | H | CH₃ | CH₃ | H | H | CH₃ | 2 | piperazinyl-pyrimidin-4-ol |
| H | —OCH₃ | OCH₃ | H | H | H | H | H | H | H | CH₃ | 2 | piperazinyl-(hydroxy)pyrimidine |
| H | —OCH₃ | —OCH₃ | H | H | H | H | H | H | H | CH₃ | 2 | piperazinyl-pyridazin-3-ol |
| H | —OCH₃ | —OCH₃ | H | H | CH₃ | H | H | H | H | CH₃ | 2 | piperazinyl-(4-fluorophenyl) |
| H | —OCH₃ | —OCH₃ | H | CH₃ | H | CH₃ | H | H | H | CH₃ | 2 | piperazinyl-(4-fluorophenyl) |
| H | OCH₃ | OCH₃ | H | H | H | H | H | CH₃ | CH₃ | CH₃ | 2 | 4-(4-fluorophenyl)piperazinyl |

TABLE 8-continued
| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | OCH$_3$ | OCH$_3$ | H | CH$_3$ | CH$_3$ | H | H | H | H | CH$_3$ | 2 | 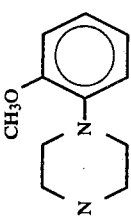 |
| H | OCH$_3$ | OCH$_3$ | H | H | H | CH$_3$ | CH$_3$ | H | H | CH$_3$ | 2 | 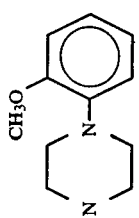 |
| H | OCH$_3$ | OCH$_3$ | H | H | H | H | H | CH$_3$ | CH$_3$ | CH$_3$ | 2 | 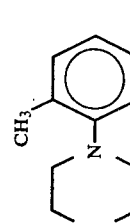 |
| H | OCH$_3$ | OCH$_3$ | H | H | H | CH$_3$ | CH$_3$ | H | H | CH$_3$ | 3 | 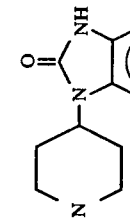 |
| H | OCH$_3$ | OCH$_3$ | H | H | H | H | H | H | H | CH$_3$ | 4 |  |

TABLE 8-continued $$\text{structure with } R_1', R_1'', R_1''', R_1'''', R_1''''', R_2, R_3, R_4, R_5, R_6, R_7, R_8, \text{O—(CH}_2)_n\text{NR}_9\text{R}_{10}$$

| $R_1'$ | $R_1''$ | $R_1'''$ | $R_1''''$ | $R_2$ | $R_3$ | $R_4$ | $R_5$ | $R_6$ | $R_7$ | $R_8$ | | n | $NR_9R_{10}$ |
|---|---|---|---|---|---|---|---|---|---|---|---|---|---|
| H | OCH$_3$ | OCH$_3$ | H | CH$_3$ | CH$_3$ | H | H | H | H | CH$_3$ | | 2 | —N(CH$_2$CH$_2$-3,4-(OCH$_3$)$_2$-C$_6$H$_3$) tetrahydroisoquinoline |
| H | OCH$_3$ | OCH$_3$ | H | H | H | CH$_3$ | CH$_3$ | H | H | CH$_3$ | | 2 | tetrahydroisoquinoline (3,4-diOCH$_3$) |
| H | OCH$_3$ | OCH$_3$ | H | H | H | H | H | CH$_3$ | CH$_3$ | CH$_3$ | | 2 | tetrahydroisoquinoline (3,4-diOCH$_3$) |
| H | OCH$_2$O | | H | CH$_3$ | CH$_3$ | H | H | H | H | | 4-F-C$_6$H$_4$ | 2 | 4-F-piperazinyl |
| H | OCH$_3$ | OCH$_3$ | H | H | H | H | CH$_3$ | CH$_3$ | H | | 4-F-C$_6$H$_4$ | 2 | 4-F-piperazinyl |
| H | OCH$_3$ | OCH$_3$ | H | H | H | H | H | H | H | | 4-F-C$_6$H$_4$ | 2 | 4-F-piperazinyl |
| H | OCH$_3$ | OCH$_3$ | H | CH$_3$ | CH$_3$ | H | H | CH$_3$ | CH$_3$ | | 4-F-C$_6$H$_4$ | 2 | 2-OCH$_3$-phenyl-piperazinyl |

TABLE 8-continued
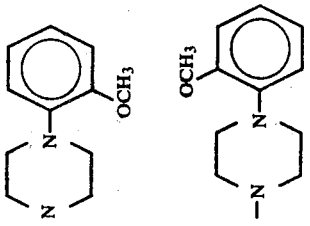
| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | $OCH_3$ | $OCH_3$ | H | H | H | $CH_3$ | $CH_3$ | H | H | 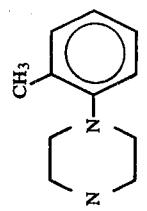 | 2 | 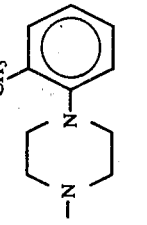 |
| H | $OCH_3$ | $OCH_3$ | H | H | H | Cl | H | $CH_3$ | $CH_3$ | 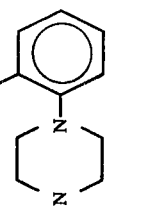 | 2 | 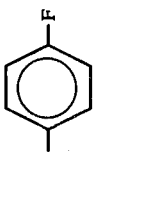 |
| H | $OCH_3$ | $OCH_3$ | H | $CH_3$ | $CH_3$ | H | H | H | H | 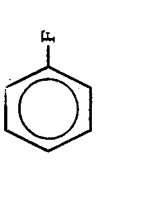 | 2 | 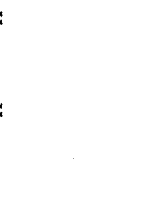 |
| H | $OCH_3$ | $OCH_3$ | H | H | H | $CH_3$ | $CH_3$ | H | H |  | 2 |  |
| H | $OCH_3$ | $OCH_3$ | H | H | H | H | H | $CH_3$ | $CH_3$ |  | 2 |  |

TABLE 8-continued
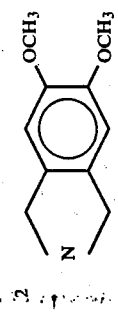
| $R_1'$ | $R_1''$ | $R_1'''$ | $R_1''''$ | $R_2$ | $R_3$ | $R_4$ | $R_5$ | $R_6$ | $R_7$ | $R_8$ | | n | $NR_9R_{10}$ |
|---|---|---|---|---|---|---|---|---|---|---|---|---|---|
| H | $OCH_3$ | $OCH_3$ | H | $CH_3$ | $CH_3$ | H | H | H | H | 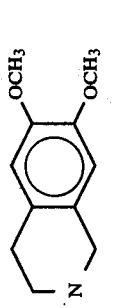 | | 2 | 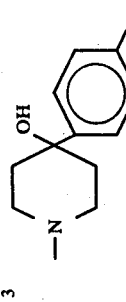 |
| H | $OCH_3$ | $OCH_3$ | H | $CH_3$ | $CH_3$ | H | H | H | H | 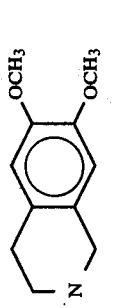 | | 2 | 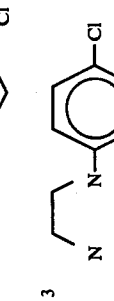 |
| H | $OCH_3$ | $OCH_3$ | H | H | H | $C_3H_7$ | H | $CH_3$ | $CH_3$ | 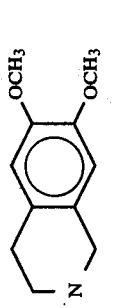 | | 2 | 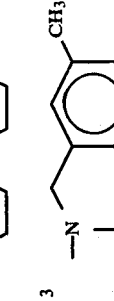 |
| H | $OCH_3$ | $OCH_3$ | H | $CH_3$ | $CH_3$ | H | H | H | H | $CH_3$ | | 3 | 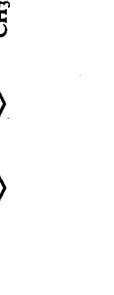 |
| H | H | H | $-OCH_3$ | $C_2H_5$ | $C_2H_5$ | H | H | H | H | H | | 3 |  |
| H | $OCH_3$ | $OCH_3$ | H | $C_3H_7$ | $C_3H_7$ | H | H | H | H | H | | 3 |  |

TABLE 8-continued

Structure: substituted benzene ring with $R_1'$, $R_1''$, $R_1'''$, $R_1''''$, $R_1'''''$ on ring and side chain $-C(R_2)(R_3)-C(R_4)(R_5)-C(R_6)(R_7)-O-C(R_8)(R_1''''')-(CH_2)_n NR_9 R_{10}$

| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | $OC_2H_5$ | H | H | $CH_3$ | $CH_3$ | H | H | H | H | $CH_3$ | 3 | piperazinyl-pyrimidine |
| H | $OCH_3$ | $OCH_3$ | H | $nC_4H_9$ | $nC_4H_9$ | H | H | H | H | H | 2 | 4-phenylpiperidine |
| OH | H | H | H | $C_2H_5$ | $C_3H_7$ | H | H | H | H | H | 3 | 4-hydroxy-4-phenylpiperidine |
| H | $OCH_3$ | $OCH_3$ | H | H | H | H | H | H | H | H | 2 | 3-hydroxy-3-phenylpiperidine |
| H | $OCH_3$ | $OCH_3$ | H | Cl | H | H | H | H | H | H | 1 | 4-(2-methylphenyl)piperidine |
| H | $OCH_3$ | $CF_3$ | H | H | H | H | H | H | H | $CH_3$ | 3 | 6,7-dimethoxy-tetrahydroisoquinoline |

TABLE 8-continued
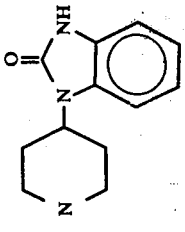
| R₁' | R₁'' | R₁''' | R₁'''' | R₂ | R₃ | R₄ | R₅ | R₆ | R₇ | R₈ | n | NR₉R₁₀ |
|---|---|---|---|---|---|---|---|---|---|---|---|---|
| H | –CH₂–O–O– | OCH₃ | H | cyclohexyl | H | H | H | H | H | H | 1 |  |
| H | OCH₃ | OCH₃ | H | CH₃ | H | H | H | H | H | H | 1 |  |
| H | OCH₃ | H | H | cyclohexyl | H | H | H | H | H | CH₃ | 2 |  |
| H | –OCH₃ | H | H | –OCH₃ | H | H | H | H | H | H | 2 | 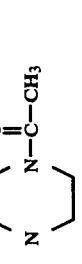 |
| H | –OCH₃ | OCH₃ | H | –Br | H | H | CH₃ | CH₃ | H | H | 2 |  |
| H | OC₂H₅ | H | H | –Cl | H | CH₃ | H | H | H | H | 2 | N–C(=O)–CH₃ piperazine |

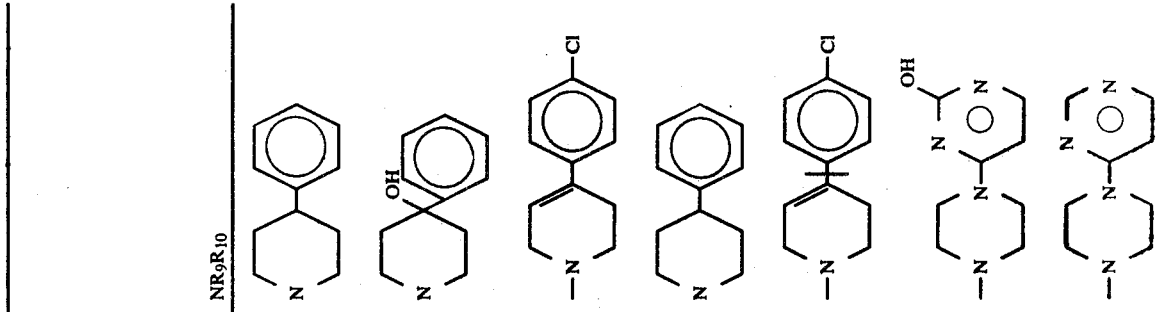

TABLE 8-continued

Structure: benzene ring with R₁', R₁'', R₁''', R₁'''', R₁''''' substituents and a side chain C(R₂)(R₃)-C(R₄)(R₅)-C(R₆)(R₇)(R₈) with -O-(CH₂)ₙ-NR₉R₁₀

| $R_1'$ | $R_1''$ | $R_1'''$ | $R_1''''$ | $R_2$ | $R_3$ | $R_4$ | $R_5$ | $R_6$ | $R_7$ | $R_8$ | $n$ | $NR_9R_{10}$ |
|---|---|---|---|---|---|---|---|---|---|---|---|---|
| H | H | H | OCH₃ | H | H | H | (phenyl) | H | H | CH₃ | 3 | 4-(furan-2-ylcarbonyl)piperazin-1-yl |
| H | —OCH₃ | H | H | H | H | H | H | H | H | H | 3 | 4-(1H-pyrrol-2-yl)piperazin-1-yl |
| H | OCH₃ | OCH₃ | H | CH₃ | CH₃ | H | H | H | H | H | 4 | 4-(1,2,4-triazol-3-yl)piperazin-1-yl |

Example 12

Following the procedure used in Examples 1 through 11, but substituting halo branched chain benzoxepins for the corresponding 1-haloalkylbenzoxepins the following compounds can be made.

TABLE 9

Structure: phenyl ring bearing substituents $R_1'$, $R_1''$, $R_1'''$, $R_1''''$ and a branch chain $-C(R_2)(R_3)(R_4)-C(R_5)(-CR_6R_7-)(-O-CR_8-\text{Branch Chain}-NR_9R_{10})$

| $R_1'$ | $R_1''$ | $R_1'''$ | $R_1''''$ | $R_2$ | $R_3$ | $R_4$ | $R_5$ | $R_6$ | $R_7$ | $R_8$ | Branch Chain | $NR_9R_{10}$ |
|---|---|---|---|---|---|---|---|---|---|---|---|---|
| H | H | $C_3H_7$ | $OCH_3$ | H | H | H | H | H | H | H | $-C(CH_3)_2-CH_2-$ | piperazinyl–pyrimidinyl |
| H | H | H | $OCH_3$ | H | H | H | H | H | H | H | $-C(CH_3)_2-C(CH_3)_2-CH_2-$ | piperazinyl–pyridyl |
| $OCH_3$ | $OCH_3$ | H | H | H | H | H | H | H | H | H | $-C(CH_3)(C_2H_5)-CH_2-CH_2-CH_2-$ | piperazinyl–pyrazolyl (NH) |
| H | $OC_2H_5$ | H | H | H | H | H | H | H | H | H | $-C(CH_3)(C_2H_5)-CH_2-$ | piperazinyl–(4-fluorophenyl) |
| H | $OCH_3$ | $OCH_3$ | $OCH_3$ | H | H | H | H | H | H | H | $-C(C_2H_5)_2-CH_2-CH_2-$ | piperazinyl–N=CH–phenyl |
| H | OH | $OCH_3$ | H | H | H | H | H | H | H | H | $-CH_2-C(C_2H_5)_2-CH_2-$ | piperazinyl–N=CH–phenyl |
| H | $OCH_3$ | H | H | H | H | H | H | H | H | H | $-CH_2-C(CH_3)(C_2H_5)-CH_2-$ | piperazinyl–(2-methylphenyl) |
| H | $OCH_3$ | Br | H | H | $CH_3$ | H | H | H | H | H | $-C(CH_3)_2-CH_2-CH_2-$ | |

TABLE 9-continued structure: phenyl ring with substituents R1', R1'', R1''', R1'''', R1''''', R8, and branch chain-NR9R10 with R2, R3, R4, R5, R6, R7 and O

| R1' | R1'' | R1''' | R1'''' | R2 | R3 | R4 | R5 | R6 | R7 | R8 | Branch Chain | NR9R10 |
|---|---|---|---|---|---|---|---|---|---|---|---|---|
| H | OCH$_3$ | Cl | Cl | H | H | H | H | H | H | H | CH$_3$—C—CH$_2$—CH$_2$—C—CH$_3$ with CH$_3$ groups | piperidine-N-(2-methylphenyl) |
| H | OCH$_3$ | CF$_3$ | H | H | H | H | H | H | H | H | C$_2$H$_5$ CH$_3$ C—C H H | NH(CH$_2$)$_2$-(3,4-dichlorophenyl) |
| H | —OCH$_2$O— | H | H | H | H | H | H | H | H | H | C$_2$H$_5$ C$_2$H$_5$ C—CH$_2$—CH—CH$_2$ C$_2$H$_5$ | tetrahydroisoquinoline (2,3-dimethyl) |
| H | OCH$_3$ | H | H | CH$_3$ | H | H | H | H | H | H | CH$_3$ C$_2$H$_5$ C—CH$_2$—CH—CH$_2$ CH$_3$ | tetrahydroisoquinoline (OH) |
| H | OCH$_3$ | H | OCH$_3$ | CH$_3$ | H | CH$_3$ | CH$_3$ | H | H | H | —CH$_3$ C—CH$_2$CH$_2$CH$_2$CH$_2$ CH$_3$ | piperazine-N-(4-fluorophenyl) |
| H | OCH$_3$ | OCH$_3$ | OCH$_3$ | H | H | H | CH$_3$ | H | H | H | CH$_3$ CH—CH$_2$C—CH$_2$—CH$_2$ CH$_3$ CH$_3$ | piperazine-N-(2-methoxyphenyl) |
| H | H | H | OCH$_3$ | H | H | H | phenyl | H | H | H | CH$_3$ —CH$_2$—C—CH$_2$CH$_2$ CH$_3$ CH$_3$ | piperazine-N-(5-chloropyridin-2-yl) |

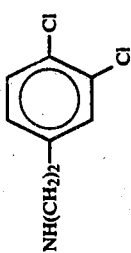
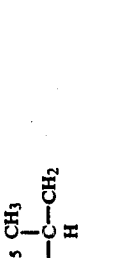
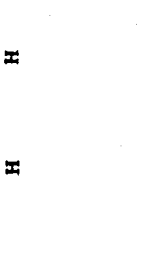
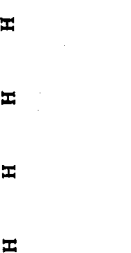
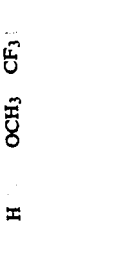

TABLE 9-continued

| $R_1'$ | $R_1''$ | $R_1'''$ | $R_1''''$ | $R_2$ | $R_3$ | $R_4$ | $R_5$ | $R_6$ | $R_7$ | $R_8$ | Branch Chain | $NR_9R_{10}$ |
|---|---|---|---|---|---|---|---|---|---|---|---|---|
| H | OH | H | H | H | Br | H | H | H | H | H | —CH—CH—CH$_2$CH$_3$ with CH$_3$ and C$_2$H$_5$ branches | 1-(benzimidazol-2(3H)-on-1-yl)piperidin-4-yl |
| H | OCH$_3$ | OCH$_3$ | H | CH$_3$ | CH$_3$ | H | H | H | H | CH$_3$ | —CH—CH$_2$—CH—CH$_2$— with CH$_3$ and CH$_3$ branches | 4-(4-fluorophenyl)piperidin-1-yl |
| H | OCH$_3$ | OCH$_3$ | H | H | H | CH$_3$ | CH$_3$ | H | H | CH$_3$ | —CH$_2$CH—CHCH$_2$— with CH$_3$ and CH$_3$ branches | 4-(4-chlorophenyl)-4-hydroxypiperidin-1-yl |
| H | OCH$_3$ | OCH$_3$ | H | H | H | (cyclopentyl) | | H | H | CH$_3$ | —CH$_2$—CH—CH$_2$ with C$_2$H$_5$ and C$_2$H$_5$ branches | 4-(4-bromophenyl)piperidin-1-yl |
| H | OC$_3$H$_7$ | OC$_3$H$_7$ | H | H | H | H | H | H | H | H | —CH$_2$—C(CH$_3$)(C$_2$H$_5$)—CH$_2$—CH$_2$— with 4-fluorophenyl branch | 4-(3-chlorophenyl)-4-hydroxypiperidin-1-yl |

Example 13

1-[2-[(1,3,4,5-tetrahydro-7,8-dimethoxy-2benzoxepin-1-yl)methoxy]ethyl]-4-(2-methoxyphenyl)piperazine A mixture of 0.50 g (1.07 mmoles) of 2-[(1,3,4,5-tetrahydro-7,8-dimethoxy-2-benzoxepin-1-yl)methoxy]ethyl]-4-nitrobenzenesulfonate, 0.22 g (1.07 mmoles) of o-methoxyphenylpiperazine, 0.15 ml (1.07 mmoles) of triethylamine, and 20 ml of tetrahydrofuran is stirred at room temperature for 24 hours. After removing the tetrahydrofuran in vacuo, the reaction mixture is extracted with methylene chloride and aqueous sodium bicarbonate. The organic layer is filtered through sodium sulfate, taken to dryness, and chromatographed on silica gel using 3% methanol:methylene chloride eluent to give 0.40 g (82%) of 1-[2-[(1,3,4,5-tetrahydro-7,8-dimethoxy-2-benzoxepin-1-yl)methoxy]ethyl]-4-(2-methoxyphenyl)piperazine. The dihydrochloride salt was prepared with hydrochloric acid in ethyl ether, m.p. 172°–175°.

Analysis: Calc'd. for $C_{26}H_{36}N_2O_5 \cdot 2HCl \cdot H_2O$: C, 57.03; H, 7.36; N, 5.12; Cl, 12.95. Found: C, 56.94; H, 7.29; N, 5.48; Cl, 12.98.

Example 14:

1-[2-[(1,3,4,5-tetrahydro-7,8-dimethoxy-2-benzoxepin-1-yl)methoxy]ethyl]-4-hydroxy-4-(3-trifluoromethylphenyl)piperidine A mixture of 0.10 g (1.50 mmoles) of 2-[(1,3,4,5-tetrahydro-7,8-dimethoxy-2-benzoxepine-1-yl)methoxy]ethyl 4-nitrobenzenesulfonate, 0.37 g (1.50 mmoles) of 4-hydroxy-4-(3-trifluoromethylphenyl)piperidine, 0.21 ml (1.50 mmoles) of triethylamine and 30 ml of tetrahydrofuran is stirred at room temperature for 3 days, at 50° for 1 day, and again at room temperature for 2 days, after which the tetrahydrofuran is removed in vacuo.

The reaction mixture is extracted with methylene chloride and aqueous sodium bicarbonate. The organic layer is filtered through sodium sulfate and taken to dryness and chromatographed on silica gel with 2% methanol:0.5% ammonium hydroxide-methylene chloride as eluent to give 0.46 g (60%) of the titled product. The hydrochloride salt is prepared with hydrochloric acid/ethyl ether, m.p. 156°–159°.

Analysis: Calc'd. for $C_{27}H_{34}F_3NO_5 \cdot HCl \cdot \frac{1}{2}H_2O$: C, 58.43; H, 6.54; N, 2.52; Cl, 6.34. Found: C, 58.60; H, 6.49; N, 2.85; Cl, 7.08.

Example 15:

1-[2-[(1,3,4,5-tetrahydro-7,8-dimethoxy-2-benzoxepin-1-yl)methoxy]ethyl]-4-(4-fluorophenyl)-piperazine A mixture of 400 mg of 2-[(1,3,4,5-tetrahydro-7,8-dimethoxy-2-benzoxepin-1-yl)methoxy]ethyl-4-nitrobenzenesulfonate, 150 mg of 4-fluorophenylpiperazine, 0.12 ml of triethylamine and tetrahydrofuran as solvent is stirred at room temperature for 18 hours after which the tetrahydrofuran is removed in vacuo. The reaction mixture is extracted with methylene chloride and aqueous sodium bicarbonate. The organic layer is filtered through sodium sulfate and taken to dryness. The residue is purified by chromatography. The product is crystallized from methylene chloride and Skelly B, and ether, m.p. 114°–114.5°.

Example 16:

1-[2-[(1,3,4,5-tetrahydro-7,8-dimethoxy-2-benzoxepin-1-yl)methoxy]ethyl]-4-(4-fluorophenyl)piperazine A mixture of 1.27 g (4.42 mmoles) of 2-[(1,3,4,5-tetrahydro-7,8-dimethoxy-2-benzoxepin-1-yl)methoxy]ethyl chloride, and 1.52 g (8.44 mmoles) of 1-fluorophenyl piperazine is stirred for 60 hours at 90°, neat. The product is isolated and crystallized as in Example 15.

Example 17:

1-[2-[(1,3,4,5-tetrahydro-7,8-dimethoxy-2-benzoxepin-1-yl)methoxy]ethyl]-4-(2-pyridyl)-piperazine A mixture of 1.00 g (3.32 mmoles) of 2-[(1,3,4,5-tetrahydro-7,8-dimethoxy-2-benzoxepin-1-yl)methoxy]ethyl chloride and 1.14 g (6.65 mmoles) of 95% 2-pyridylpiperazine is stirred at 90° for 20 hours. Approximately 3 ml of toluene is then added and the reaction mixture is heated for an additional 28 hours. After cooling, the reaction mixture is filtered, washing with toluene, and the filtrate is extracted with (1) aqueous sodium bicarbonate and (2) brine. The organic layer is taken to dryness and the residue is chromatographed on silica gel using 3% methanol:0.5% ammonium hydroxide in methylene chloride as eluent to give 1.30 g (92%) of the stated product. The hydrochloric acid salt (dihydrate) was prepared from hydrogen chloride in ethanol.

Analysis: Calc'd. for $C_{24}H_{33}N_3O_4 \cdot HCl \cdot 2H_2O$ C, 57.64; H, 7.46; N, 8.40. Found: C, 57.31; H, 7.69; N, 8.23.

Example 18

Following the procedure used in Example 12 through 17 but substituting the appropriate 1-[2-[(1,3,4,5-tetrahydro-2-benzoxepin-1-yl)alkoxy]alkyl chlorides or benzene sulfonates and the appropriate amines, the following compounds can be made.

TABLE 10
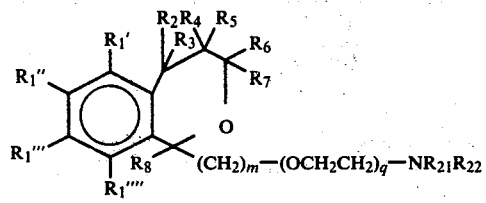
| R₁' | R₁'' | R''' | R₁'''' | R₂ | R₃ | R₄ | R₅ | R₆ | R₇ | R₈ | m | q | NR₂₁R₂₂ |
|---|---|---|---|---|---|---|---|---|---|---|---|---|---|
| H | H | propyl | —OCH₃ | H | H | H | H | H | H | H | 1 | 1 | 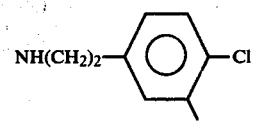 |
| H | H | H | —OCH₃ | H | H | H | H | H | H | H | 1 | 2 | 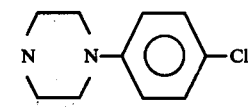 |
| OCH₃ | OCH₃ | H | H | H | H | H | H | H | H | H | 1 | 3 | 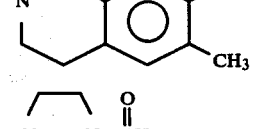 |
| H | OC₂H₅ | H | H | H | H | H | H | H | H | H | 2 | 1 | 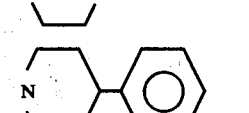 |
| H | OCH₃ | OCH₃ | OCH₃ | H | H | H | H | H | H | H | 2 | 2 | 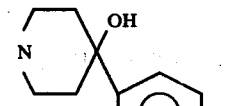 |
| —OCH₃ | —OH | H | H | H | H | H | H | H | H | H | 2 | 3 | 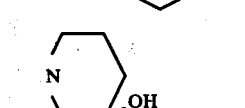 |
| H | —OCH₃ | Br | H | H | H | H | H | H | H | H | 3 | 1 | 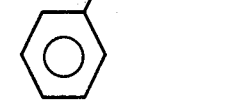 |
| H | —OCH₃ | Cl | Cl | H | H | H | H | H | H | H | 3 | 2 | 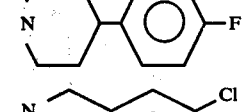 |
| H | —OCH₃ | —CF₃ | H | H | H | H | H | H | H | H | 3 | 3 | 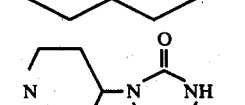 |
| H | 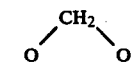 | | H | H | H | H | H | H | H | H | 1 | 1 | 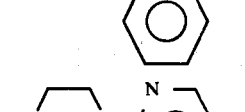 |
| H | —OCH₃ | H | H | CH₃ | H | H | H | H | H | H | 2 | 1 | 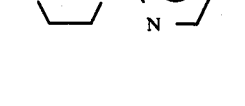 |

TABLE 10-continued

Structure: Phenyl ring with substituents R₁', R₁'', R₁''', R₁'''', R₁''''', R₈, and side chain —C(R₂)(R₃)—C(R₄)(R₅)—C(R₆)(R₇)(O(CH₂)$_m$—(OCH₂CH₂)$_q$—NR₂₁R₂₂)

| R₁' | R₁'' | R₁''' | R₁'''' | R₂ | R₃ | R₄ | R₅ | R₆ | R₇ | R₈ | m | q | NR₂₁R₂₂ |
|---|---|---|---|---|---|---|---|---|---|---|---|---|---|
| H | OCH₃ | H | OCH₃ | CH₃ | H | CH₃ | H | H | H | H | 3 | 2 | piperazinyl-(2-CH₃-phenyl) |
| H | OCH₃ | OCH₃ | OCH₃ | H | H | OCH₃ | CH₃ | H | H | H | 2 | 3 | piperazinyl-(4-F-phenyl) |
| H | H | H | OCH₃ | H | H | H | C₆H₅ | H | H | H | 1 | 3 | piperazinyl-(2-OCH₃-phenyl) |
| H | OH | H | H | H | Br | H | H | H | H | H | 1 | 1 | 6,7-dimethoxy-tetrahydroisoquinolinyl |
| H | OCH₃ | OCH₃ | H | CH₃ | CH₃ | H | H | H | H | H | 2 | 2 | NH(CH₃)₂-(3-Cl-phenyl) |
| H | OCH₃ | OCH₃ | H | H | H | CH₃ | CH₃ | H | H | H | 3 | 3 | piperazinyl-(3-Br-phenyl) |
| H | OCH₃ | OCH₃ | H | C₅H₉ | H | H | H | H | H | H | 3 | 1 | 6,7-dimethyl-tetrahydroisoquinolinyl |
| H | OC₃H₇ | OC₃H₇ | H | H* | H | * | H | H | H | H | 1 | 1 | piperazinyl-(4-C₂H₃-phenyl) |
| H | H | OCH₃ | OCH₃ | H | H | C₅H₉ | H | H | H | H | 1 | 1 | 7-OH-tetrahydroisoquinolinyl |
| H | OH | OH | H | C₃H₇ | H | H | H | H | H | H | 1 | 1 | NH(CH₂)₂-(3,4-dimethoxyphenyl) |
| H | —OCH₃ | —OCH₃ | H | H | H | H | H | H | H | CH₃ | 1 | 3 | —N(CH₃)₂ |
| H | —OCH₃ | —OCH₃ | H | H | H | H | H | H | H | CH₃ | 1 | 4 | morpholinyl |
| H | —OCH₃ | —OCH₃ | H | CH₃ | CH₃ | H | H | H | H | CH₃ | 1 | 4 | —N—H-butyl |
| H | OCH₃ | —OCH₃ | H | H | H | CH₃ | CH₃ | H | H | CH₃ | 2 | 3 | piperazinyl-(4-F-phenyl) |
| H | OCH₃ | OCH₃ | H | CH₃ | CH₃ | H | H | H | H | C₆H₅ | 1 | 3 | —NH-t-butyl |

TABLE 10-continued
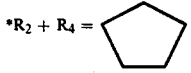
| $R_1'$ | $R_1''$ | $R'''$ | $R_1''''$ | $R_2$ | $R_3$ | $R_4$ | $R_5$ | $R_6$ | $R_7$ | $R_8$ | m | q | $NR_{21}R_{22}$ |
|---|---|---|---|---|---|---|---|---|---|---|---|---|---|
| H | $OCH_3$ | $OCH_3$ | H | H | H | H | H | H | H | $C_6H_5$ | 1 | 3 | $-NH_2$ |
*$R_2 + R_4 =$ ⬠
Example 18A
Following procedures similar to those of Examples 1 to 11, but substituting the appropriate 1-haloalkyl-2-benzothiepin for 1-haloalkyl-2-benzoxepin, benzothiepins of Table 11 can be prepared.

TABLE 11

| R1' | R1'' | R1''' | R1'''' | R2 | R3 | R4 | R5 | R6 | R7 | R8 | n | NR9R10 |
|---|---|---|---|---|---|---|---|---|---|---|---|---|
| H | H | propyl | —OCH$_3$ | H | H | H | H | H | H | H | 1 | 3,4-dichlorophenyl-NH(CH$_2$)$_2$ |
| H | H | H | —OCH$_3$ | H | H | H | H | H | H | H | 1 | 4-chlorophenyl-piperazinyl |
| OCH$_3$ | —OCH$_3$ | H | H | H | H | H | H | H | H | H | 1 | 3,4-dimethylphenyl-CH$_2$-N< |
| H | H | H | H | H | Br | H | H | H | H | H | 4 | 3,4-dimethoxyphenyl-CH$_2$CH$_2$-N< |
| H | OH | H | H | H | CH$_3$ | H | H | H | H | H | 5 | 3,4-dichlorophenyl-NH(CH$_2$)$_2$ |
| H | OCH$_3$ | OCH$_3$ | H | CH$_3$ | H | CH$_3$ | CH$_3$ | H | H | H | 5 | 3-bromophenyl-piperazinyl |
| H | OCH$_3$ | OCH$_3$ | H | H | H | CH$_3$ | CH$_3$ | H | H | H | 5 | 3-bromophenyl-piperazinyl |

TABLE 11-continued
| R$_1'$ | R$_1''$ | R$_1'''$ | R$_1''''$ | R$_2$ | R$_3$ | R$_4$ | R$_5$ | R$_6$ | R$_7$ | R$_8$ | n | NR$_9$R$_{10}$ |
|---|---|---|---|---|---|---|---|---|---|---|---|---|
| H | OCH$_3$ | OCH$_3$ | H | H | H | H | cyclopentyl | H | H | H | 5 | 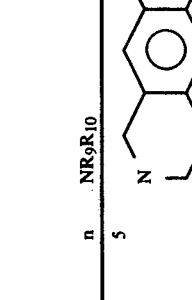 |
| H | OC$_3$H$_7$ | OC$_3$H$_7$ | H | * | H | * | H | H | H | H | 5 | 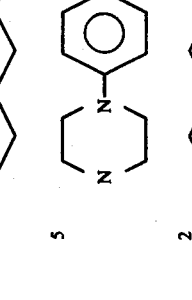 |
| H | H | OCH$_3$ | OCH$_3$ | H | H | cyclopentyl | H | H | H | H | 2 | 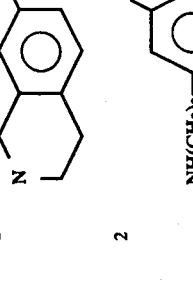 |
| H | OH | OH | H | C$_3$H$_7$ | H | H | H | H | H | H | 2 | 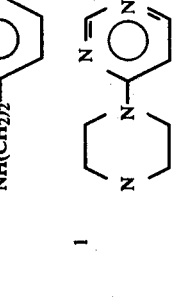 |
| H | OCH$_3$ | OCH$_3$ | CF$_3$ | H | H | H | H | H | H | H | 1 | 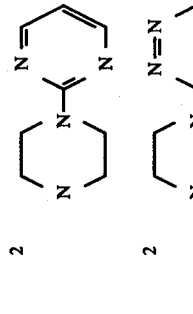 |
| H | —OCH$_3$ | —OCH$_3$ | H | H | H | H | H | H | H | H | 2 | 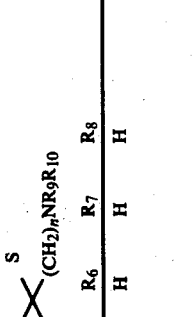 |
| H | —OCH$_3$ | —OCH$_3$ | H | H | H | H | H | H | H | H | 2 | 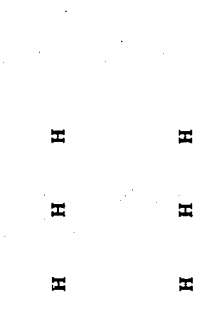 |

TABLE 11-continued

| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | —OCH₃ | —OCH₃ | H | CH₃ | —CH₃ | H | H | H | H | H | 2 | N-piperazinyl-(4-fluorophenyl) |
| H | OC₂H₅ | H | H | H | H | H | H | H | H | H | 1 | N-acetylpiperazinyl |
| H | OCH₃ | OCH₃ | H | H | H | H | H | H | H | H | 1 | 4-phenylpiperidinyl |
| —OCH₃ | —OH | H | H | H | H | H | H | H | H | H | 1 | 4-hydroxy-4-phenylpiperidinyl |
| H | —OCH₃ | Br | H | H | H | H | H | H | H | H | 1 | 2-phenylpiperidinyl (OH) |
| H | —OCH₃ | Cl | Cl | H | H | H | H | H | H | H | 1 | 4-phenylpiperidinyl |

TABLE 11-continued
| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | —OCH$_3$ | —CF$_3$ | H | H | H | H | H | H | H | H | 2 | 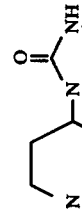 |
| H | CH$_2$–O–O | | H | H | H | H | H | H | H | H | 3 | 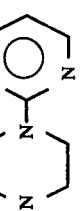 |
| H | H | H | H | H | H | H | H | H | H | H | 3 |  |
| H | OCH$_3$ | H | H | CH$_3$ | H | H | H | H | H | H | 3 | 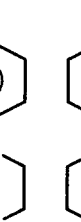 |
| H | OCH$_3$ | H | OCH$_3$ | CH$_3$ | H | CH$_3$ | CH$_3$ | H | H | H | 3 | 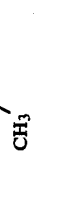 |
| H | OCH$_3$ | OCH$_3$ | OCH$_3$ | H | H | H | H | H | H | H | 4 |  |
| H | H | H | OCH$_3$ | H | H | H | ⬡ | H | H | H | 4 |  |

TABLE 11-continued
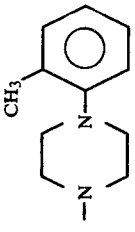
| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | OCH$_3$ | OCH$_3$ | H | H | H | —CH$_3$ | —CH$_3$ | H | H | H | 2 |  |
| H | OCH$_3$ | OCH$_3$ | H | H | H | H | H | CH$_3$ | CH$_3$ | H | 2 | 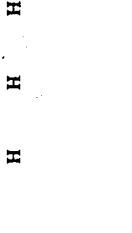 |
| H | OCH$_3$ | OCH$_3$ | H | CH$_3$ | CH$_3$ | H | H | H | H | H | 2 | 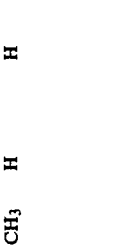 |
| H | OCH$_3$ | OCH$_3$ | H | H | H | CH$_3$ | CH$_3$ | H | H | H | 2 |  |
| H | —O—CH$_2$—O— | | H | H | H | H | H | CH$_3$ | CH$_3$ | H | 2 |  |
| H | —OCH$_3$ | —OCH$_3$ | H | CH$_3$ | CH$_3$ | H | H | H | H | H | 2 | |

TABLE 11-continued

| R₁' | R₁'' | R₁''' | R₁'''' | R₂ | R₃ | R₄ | R₅ | R₆ | R₇ | R₈ | n | NR₉R₁₀ |
|---|---|---|---|---|---|---|---|---|---|---|---|---|
| H | OCH₃ | OCH₃ | H | H | H | CH₃ | CH₃ | H | H | H | 2 | ![2-methylphenyl-piperazinyl] |
| H | OCH₃ | OCH₃ | H | H | H | H | H | CH₃ | CH₃ | H | 2 | ![2-methylphenyl-piperazinyl] |
| H | OCH₃ | OCH₃ | H | CH₃ | CH₃ | H | H | H | H | H | 2 | ![benzimidazolinone-piperidinyl] |
| H | OCH₃ | OCH₃ | H | CH₃ | CH₃ | H | H | H | H | H | 2 | ![3,4-dimethoxybenzyl-N] |
| H | OCH₃ | OCH₃ | H | H | H | H | H | CH₃ | CH₃ | H | 2 | ![3,4-dimethoxyphenethyl-N] |
| H | OCH₃ | OCH₃ | H | CH₃ | CH₃ | H | H | H | H | H | 2 | ![piperazinyl-pyrimidinyl] |

TABLE 11-continued structure: benzene ring with R1', R1'', R1''', R1'''' substituents and a side chain containing R2, R3, R4, R5, R6, R7, and S-C(R8)(R1'''')-(CH2)n-NR9R10

| R1' | R1'' | R1''' | R2 | R3 | R4 | R5 | R6 | R7 | R8 | n | NR9R10 |
|---|---|---|---|---|---|---|---|---|---|---|---|
| H | OCH3 | OCH3 | H | H | CH3 | CH3 | H | H | CH3 | 2 | piperazinyl-pyrimidin-4-ol |
| H | —OCH3 | OCH3 | H | H | H | H | H | H | CH3 | 2 | piperazinyl-pyrimidin-6-ol |
| H | —OCH3 | OCH3 | H | H | H | H | H | H | CH3 | 2 | piperazinyl-pyridazin-6-ol |
| H | —OCH3 | OCH3 | H | CH3 | H | H | H | H | CH3 | 2 | 4-(4-fluorophenyl)piperazinyl |
| H | —OCH3 | OCH3 | CH3 | H | CH3 | CH3 | H | H | CH3 | 2 | 4-(4-fluorophenyl)piperazinyl |
| H | OCH3 | OCH3 | H | H | H | H | CH3 | CH3 | CH3 | 2 | 4-(4-fluorophenyl)-N-methylpiperazinyl |

TABLE 11-continued

| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | OCH$_3$ | OCH$_3$ | H | CH$_3$ | CH$_3$ | H | H | H | H | CH$_3$ | 2 | 2-methoxyphenyl-piperazinyl |
| H | OCH$_3$ | OCH$_3$ | H | H | H | CH$_3$ | CH$_3$ | H | H | H | 2 | 2-methoxyphenyl-N-methylpiperazinyl |
| H | OCH$_3$ | OCH$_3$ | H | H | H | H | H | H | CH$_3$ | CH$_3$ | 2 | 2-methoxyphenyl-N-methylpiperazinyl |
| H | OCH$_3$ | OCH$_3$ | H | H | H | CH$_3$ | CH$_3$ | CH$_3$ | CH$_3$ | CH$_3$ | 3 | 2-methylphenyl-piperazinyl |
| H | OCH$_3$ | OCH$_3$ | H | H | H | H | H | H | H | CH$_3$ | 4 | 1-methylpiperidin-4-yl-benzimidazolone |

TABLE 11-continued
| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | OCH$_3$ | OCH$_3$ | H | CH$_3$ | CH$_3$ | H | H | H | H | CH$_3$ | 2 | 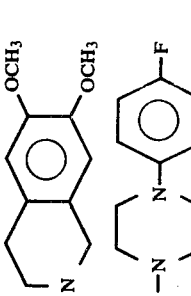 |
| H | OCH$_3$ | OCH$_3$ | H | H | H | CH$_3$ | CH$_3$ | H | H | CH$_3$ | 2 | 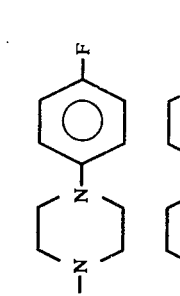 |
| H | OCH$_3$ | OCH$_3$ | H | H | H | H | H | H | CH$_3$ | CH$_3$ | 2 | 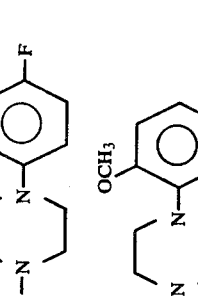 |
| H |  | H | H | CH$_3$ | CH$_3$ | H | H | CH$_3$ | CH$_3$ | H | 2 | 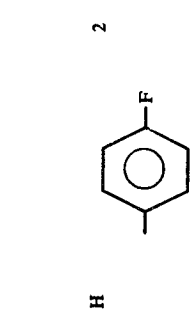 |
| H | OCH$_3$ | OCH$_3$ | H | H | H | CH$_3$ | CH$_3$ | H | H | H | 2 | 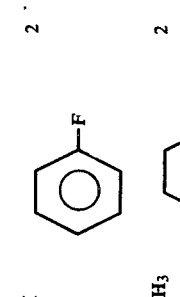 |
| H | OCH$_3$ | OCH$_3$ | H | H | H | H | H | H | H | H | 2 | 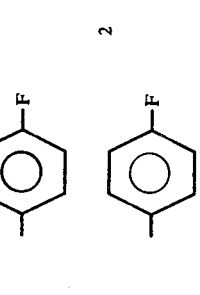 |
| H | OCH$_3$ | OCH$_3$ | H | CH$_3$ | CH$_3$ | H | H | CH$_3$ | CH$_3$ | H | 2 |  |

TABLE 11-continued
| R1' | R1'' | R1''' | R2 | R3 | R4 | R5 | R6 | R7 | R8 | n | NR9R10 |
|---|---|---|---|---|---|---|---|---|---|---|---|
| H | OCH3 | H | H | H | CH3 | CH3 | H | H |  | 2 |  |
| H | OCH3 | H | H | H | Cl | H | CH3 | CH3 |  | 2 |  |
| H | OCH3 | H | CH3 | CH3 | H | H | H | H |  | 2 |  |
| H | OCH3 | H | H | H | CH3 | CH3 | H | H |  | 2 |  |
| H | OCH3 | H | H | H | H | H | CH3 | CH3 |  | 2 |  |

TABLE 11-continued

| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | OCH₃ | OCH₃ | H | CH₃ | CH₃ | H | H | H | H | ![4-F-phenyl] | 2 | ![N-methylpiperazinyl-benzimidazolone] |
| H | OCH₃ | OCH₃ | H | CH₃ | CH₃ | H | H | H | H | ![4-F-phenyl] | 2 | ![3,4-dimethoxy-N-methyltetrahydroisoquinolinyl] |
| H | OCH₃ | OCH₃ | H | H | H | C₃H₇ | H | CH₃ | CH₃ | ![4-F-phenyl] | 2 | ![3,4-dimethoxytetrahydroisoquinolinyl] |
| H | OCH₃ | OCH₃ | H | CH₃ | CH₃ | H | H | CH₃ | H | CH₃ | 3 | ![4-(4-chlorophenyl)-4-hydroxy-N-methylpiperidinyl] |
| H | H | H | —OCH₃ | C₂H₅ | C₂H₅ | H | H | H | H | H | 3 | ![4-(4-chlorophenyl)piperazinyl] |
| H | OCH₃ | OCH₃ | H | C₃H₇ | C₃H₇ | H | H | H | H | H | 3 | ![3,4-dimethyl-N-methyltetrahydroisoquinolinyl] |

TABLE 11-continued
| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | $OC_2H_5$ | H | H | $CH_3$ | $CH_3$ | H | H | H | H | $CH_3$ | 3 | 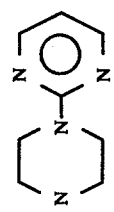 |
| H | $OCH_3$ | $OCH_3$ | H | $nC_4H_9$ | $nC_4H_9$ | H | H | H | H | H | 2 | 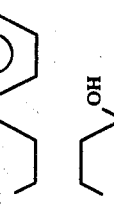 |
| OH | H | H | H | $C_2H_5$ | $C_3H_7$ | H | H | H | H | H | 3 | 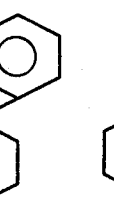 |
| H | $OCH_3$ | $OCH_3$ | H | H | H | H | H | H | H | H | 2 | 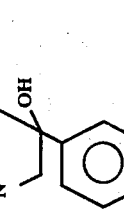 |
| H | $OCH_3$ | $OCH_3$ | H | Cl | H | H | H | H | H | H | 1 | 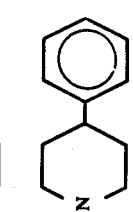 |
| H | $OCH_3$ | $CF_3$ | H | H | H | H | H | H | H | $CH_3$ | 3 | 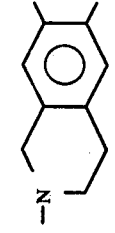 |

TABLE 11-continued

| $R_1'$ | $R_1''$ | $R_1'''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|
| H | —O-CH$_3$-O— | H | | H | H | H | H | H | H | 1 | 1-(benzimidazolin-2-one-yl)piperidin-4-yl |
| H | OCH$_3$ | OCH$_3$ | CH$_3$ | H | H | H | H | H | H | 1 | piperidin-4-yl (pyridine-type) |
| H | OCH$_3$ | H | cyclohexyl | H | H | H | H | H | H | 1 | NH(CH$_2$)$_2$-(3,4-dichlorophenyl) |
| H | —OCH$_3$ | H | —OCH$_3$ | H | H | H | H | H | CH$_3$ | 2 | 4-(4-chlorophenyl)piperazin-1-yl |
| H | —OCH$_3$ | OCH$_3$ | —Br | H | H | CH$_3$ | CH$_3$ | H | H | 2 | 6,7-dimethyl-1,2,3,4-tetrahydroisoquinolin-2-yl |
| H | OC$_2$H$_5$ | H | —Cl | H | CH$_3$ | H | H | H | H | 2 | 4-acetylpiperazin-1-yl |

TABLE 11-continued

| $R_1'$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|
| H | —OCH$_3$ | OCH$_3$ | H | CH$_3$ | H | cyclopentyl | H | H | H | 2 | 4-phenylpiperidin-1-yl |
| H | —OCH$_3$ | H | CH$_3$ | Cl | H | H | H | H | H | 3 | 4-hydroxy-4-phenylpiperidin-1-yl |
| H | OCH$_3$ | H | Cl | H | H | H | H | H | H | 3 | 4-(4-chlorophenyl)piperidin-1-yl |
| H | OCH$_3$ | Cl | H | H | H | H | H | H | H | 2 | 4-phenyl-1,2,3,6-tetrahydropyridin-1-yl |
| H | OCH$_3$ | H | CH$_3$ | CH$_3$ | H | H | H | H | CH$_3$ | 2 | 4-(4-chlorophenyl)-1,2,3,6-tetrahydropyridin-1-yl |
| H | H | H | CH$_3$ | H | CH$_3$ | H | H | H | CH$_3$ | 5 | 4-(2-hydroxypyrimidin-4-yl)piperazin-1-yl |
| H | OCH$_3$ | H | CH$_3$ | H | H | H | H | H | | | |

TABLE 11-continued

| $R_1'$ | $R_1''$ | $R_1'''$ | $R_1''''$ | $R_2$ | $R_3$ | $R_4$ | $R_5$ | $R_6$ | $R_7$ | $R_8$ | n | $NR_9R_{10}$ |
|---|---|---|---|---|---|---|---|---|---|---|---|---|
| H | —CH₃ | H | H | OCH₃ | H | H | H | H | H | CH₃ | 5 | [pyridyl-piperazine] |
| H | H | H | OCH₃ | H | H | H | phenyl | H | H | H | 3 | [furoyl-piperazine] |
| H | —OCH₃ | H | H | H | H | H | H | H | H | CH₃ | 3 | [pyrrolyl-piperazine] |
| H | OCH₃ | OCH₃ | H | CH₃ | CH₃ | H | H | H | H | H | 4 | [triazolyl-piperazine] |

*$R_2+R_4=$ cyclopentyl

Example 18B

Following procedures similar to those Examples 1–10 and 12 and substituting the appropriate 1-haloalkyl-2-benzothiepin for 1-haloalkyl-2-benzoxepin, 2-benzothiepins with branched-chain amines (Table 12) can be prepared.

TABLE 12
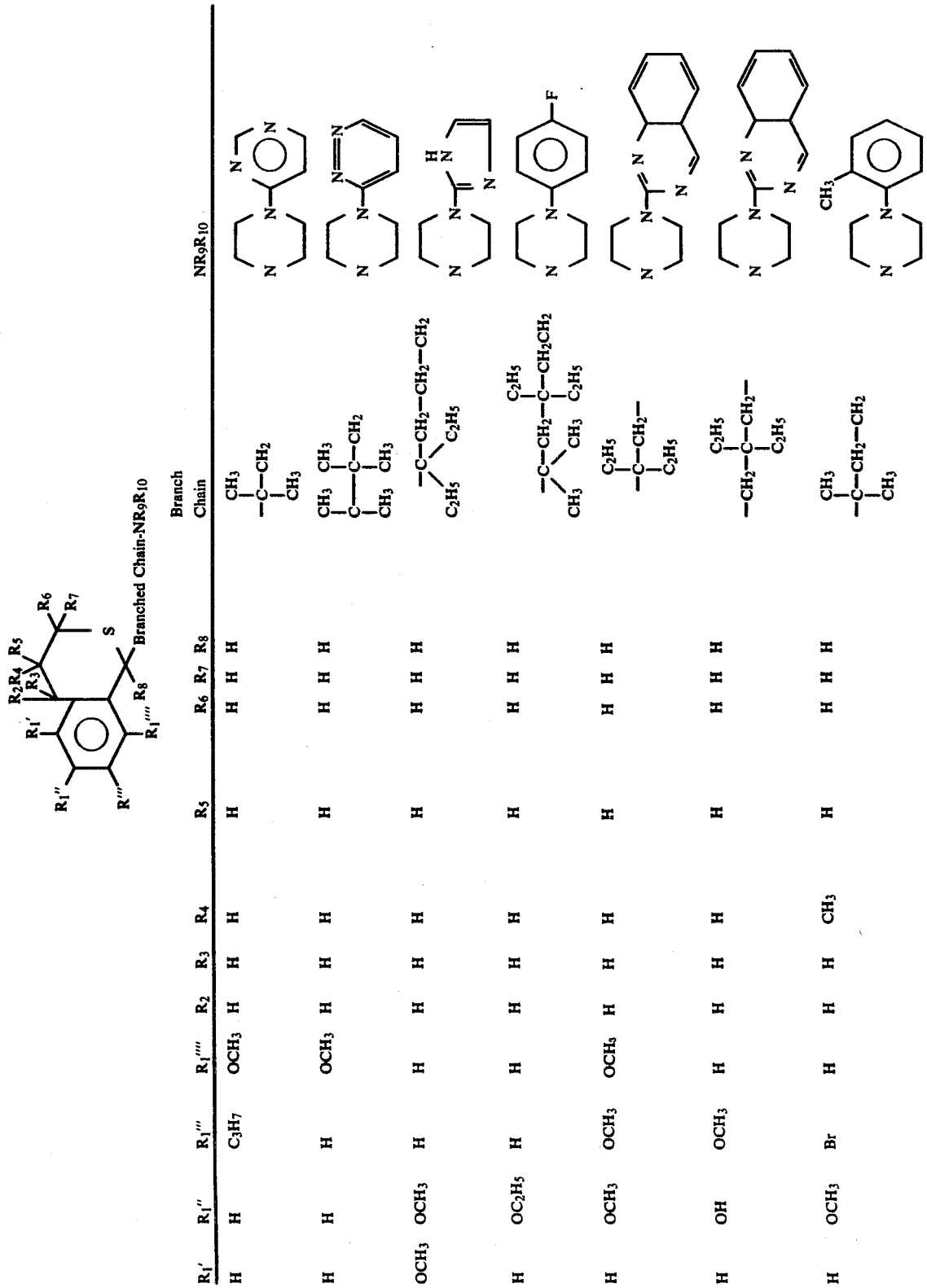

TABLE 12-continued

| $R_1'$ | $R_1''$ | $R_1'''$ | $R_1''''$ | $R_2$ | $R_3$ | $R_4$ | $R_5$ | $R_6$ $R_7$ $R_8$ | Branch Chain | $NR_9R_{10}$ |
|---|---|---|---|---|---|---|---|---|---|---|
| H | OCH$_3$ | Cl | Cl | H | H | H | H | H H H | CH$_3$–C(CH$_3$)(CH$_3$)–CH$_2$–C(CH$_3$)(CH$_3$)–CH$_3$ | 2-CH$_3$-phenyl-piperidine |
| H | OCH$_3$ | CF$_3$ | H | H | H | H | H | H H H | C$_2$H$_5$–C(CH$_3$)(H)–CH$_2$ | 2,4-Cl$_2$-phenyl-NH(CH$_2$)$_2$ |
| H | –OCH$_2$O– | | H | H | H | H | H | H H H | C$_2$H$_5$–C(C$_2$H$_5$)(CH$_3$)–CH$_2$–CH(CH$_3$)–CH$_2$ | 3,4-di-CH$_3$-tetrahydroisoquinoline |
| H | OCH$_3$ | H | H | H | H | H | H | H H H | C$_2$H$_5$–C(C$_2$H$_5$)(CH$_3$)–CH$_2$–CH(CH$_3$)–CH$_2$ | 6-OH-tetrahydroisoquinoline |
| H | OCH$_3$ | H | OCH$_3$ | CH$_3$ | H | CH$_3$ | H | H H H | –CH$_3$ –C(CH$_3$)(CH$_3$)–CH$_2$CH$_2$CH$_2$CH$_2$– | 4-F-phenyl-piperazine |
| H | OCH$_3$ | OCH$_3$ | OCH$_3$ | CH$_3$ | H | H | CH$_3$ | H H H | CH(CH$_3$)–CH$_2$C(CH$_3$)(CH$_3$)–CH$_2$–CH(CH$_3$)–CH$_3$ | 2-OCH$_3$-phenyl-piperazine |
| H | H | H | OCH$_3$ | H | H | H | phenyl | H H H | –CH$_2$–C(CH$_3$)(CH$_3$)–CH$_2$CH$_3$ | 5-Cl-pyridyl-piperazine |

TABLE 12-continued

| R$_1'$ | R$_1''$ | R$_1'''$ | R$_1''''$ | R$_2$ | R$_3$ | R$_4$ | R$_5$ | R$_6$ | R$_7$ | R$_8$ | Branch Chain | NR$_9$R$_{10}$ |
|---|---|---|---|---|---|---|---|---|---|---|---|---|
| H | OH | H | H | H | Br | H | H | H | H | H | —CH—CH—CH$_2$CH<br>CH$_3$<br>C$_2$H$_5$ | benzimidazolone-piperidine |
| H | OCH$_3$ | OCH$_3$ | H | CH$_3$ | CH$_3$ | H | H | H | H | CH$_3$ | —CH—CH$_2$—CH—CH$_2$—<br>CH$_3$ CH$_3$ | 4-fluorophenyl-piperazine |
| H | OCH$_3$ | OCH$_3$ | H | H | H | (cyclopentyl) | CH$_3$ | H | H | CH$_3$ | —CH$_2$CH CHCH$_2$—<br>CH$_3$ CH$_3$ | 4-chlorophenyl-4-hydroxy-piperidine |
| H | OCH$_3$ | OCH$_3$ | H | H | H | H | CH$_3$ | H | H | CH$_3$ | CH$_2$—CH—CH$_2$<br>C$_2$H$_5$ | 4-bromophenyl-piperazine |
| H | OC$_3$H$_7$ | OC$_3$H$_7$ | H | H | H | H | H | H | H | (4-fluorophenyl) | —CH$_2$—C—CH$_2$—<br>CH$_3$<br>C$_2$H$_5$ | 3-chlorophenyl-4-hydroxy-piperidine |

Example 19

Following procedures similar to those of Examples 13 through 18, but substituting the appropriate (1,3,4,5-tetrahydro-2-benzothiepin-1-yl)alkoxy alkyl halides or benzenesulfonates for the corresponding benzoxepins, the benzothiepins of Table 13 can be prepared.

TABLE 13

General structure: benzothiepin with substituents $R_1'$, $R_1''$, $R_1'''$, $R_1''''$ on the benzene ring; $R_2$, $R_3$, $R_4$, $R_5$, $R_6$, $R_7$, $R_8$ on the aliphatic positions; side chain $-(CH_2)_m-(OCH_2CH_2)_q-NR_{21}R_{22}$ attached via S-containing ring.

| $R_1'$ | $R_1''$ | $R_1'''$ | $R_1''''$ | $R_2$ | $R_3$ | $R_4$ | $R_5$ | $R_6$ | $R_7$ | $R_8$ | m | q | $NR_{21}R_{22}$ |
|---|---|---|---|---|---|---|---|---|---|---|---|---|---|
| H | H | propyl | —OCH₃ | H | H | H | H | H | H | H | 1 | 1 | —NH(CH₂)₂—(3,4-dichlorophenyl) |
| H | H | H | —OCH₃ | H | H | H | H | H | H | H | 1 | 2 | 4-(4-chlorophenyl)piperazin-1-yl |
| OCH₃ | OCH₃ | H | H | H | H | H | H | H | H | H | 1 | 3 | 6,7-dimethyl-1,2,3,4-tetrahydroisoquinolin-2-yl |
| H | OCH₂H₅ | H | H | H | H | H | H | H | H | H | 2 | 1 | 4-acetylpiperazin-1-yl |
| H | OCH₃ | OCH₃ | OCH₃ | H | H | H | H | H | H | H | 2 | 2 | 4-phenylpiperidin-1-yl |
| —OCH₃ | —OH | H | H | H | H | H | H | H | H | H | 2 | 3 | 4-hydroxy-4-phenylpiperidin-1-yl |
| H | —OCH₃ | Br | H | H | H | H | H | H | H | H | 3 | 1 | 2-hydroxy-2-phenylpiperidin-1-yl |
| H | —OCH₃ | Cl | Cl | H | H | H | H | H | H | H | 3 | 2 | 4-(4-fluorophenyl)piperidin-1-yl |
| H | —OCH₃ | —CF₃ | H | H | H | H | H | H | H | H | 3 | 3 | 7-chloro-1,2,3,4-tetrahydroisoquinolin-2-yl |
| H | —OCH₂O— (methylenedioxy spanning $R_1''$/$R_1'''$) | | H | H | H | H | H | H | H | H | 1 | 1 | 4-(2-oxo-2,3-dihydro-1H-benzimidazol-1-yl)piperidin-1-yl |
| H | —OCH₃ | H | H | CH₃ | H | H | H | H | H | H | 2 | 1 | 4-(pyrimidin-2-yl)piperazin-1-yl |

TABLE 13-continued

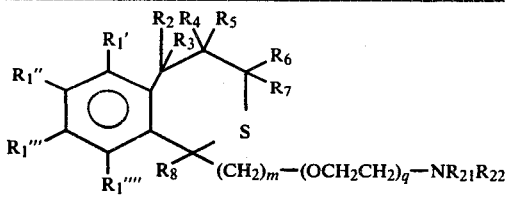

| R1' | R1'' | R1''' | R1'''' | R2 | R3 | R4 | R5 | R6 | R7 | R8 | m | q | NR21R22 |
|---|---|---|---|---|---|---|---|---|---|---|---|---|---|
| H | OCH3 | H | OCH3 | CH3 | H | CH3 | H | H | H | H | 3 | 2 | piperazinyl-(2-CH3-phenyl) |
| H | OCH3 | OCH3 | OCH3 | H | H | OCH3 | CH3 | H | H | H | 2 | 3 | piperazinyl-(4-F-phenyl) |
| H | H | H | OCH3 | H | H | H | phenyl | H | H | H | 1 | 3 | piperazinyl-(2-OCH3-phenyl) |
| H | OH | H | H | H | Br | H | H | H | H | H | 1 | 1 | 6,7-dimethoxy-tetrahydroisoquinolinyl |
| H | OCH3 | OCH3 | H | CH3 | CH3 | H | H | H | H | H | 2 | 2 | NH(CH2)2-(3,4-diCl-phenyl) |
| H | OCH3 | OCH3 | H | H | H | CH3 | CH3 | H | H | H | 3 | 3 | piperazinyl-(3-Br-phenyl) |
| H | OCH3 | OCH3 | H | cyclopentyl | | H | H | H | H | H | 3 | 1 | 6,7-dimethyl-tetrahydroisoquinolinyl |
| H | OC3H7 | OC3H7 | H | * | H | * | H | H | H | H | 1 | 1 | piperazinyl-(4-C2H5-phenyl) |
| H | H | OCH3 | OCH3 | H | H | cyclopentyl | | H | H | H | 1 | 1 | 7-OH-tetrahydroisoquinolinyl |
| H | OH | OH | H | C3H7 | H | H | H | H | H | H | 1 | 1 | NH(CH2(2-(3,4-diOCH3-phenyl) |
| H | —OCH3 | —OCH3 | H | H | H | H | H | H | H | CH3 | 1 | 3 | —N(CH3)2 |
| H | —OCH3 | —OCH3 | H | H | H | H | H | H | H | CH3 | 1 | 3 | morpholino |
| H | —OCH3 | —OCH3 | H | CH3 | CH3 | H | H | H | H | CH3 | 1 | 4 | —N—H butyl |
| H | OCH3 | —OCH3 | H | H | H | CH3 | CH3 | H | H | CH3 | 2 | 3 | piperazinyl-(4-F-phenyl) |
| H | OCH3 | OCH3 | H | CH3 | CH3 | H | H | H | H | C6H5 | 1 | 3 | —NH-t-butyl |

TABLE 13-continued

| $R_1'$ | $R_1''$ | $R_1'''$ | $R_1''''$ | $R_2$ | $R_3$ | $R_4$ | $R_5$ | $R_6$ | $R_7$ | $R_8$ | m | q | $NR_{21}R_{22}$ |
|---|---|---|---|---|---|---|---|---|---|---|---|---|---|
| H | $OCH_3$ | $OCH_3$ | H | H | H | H | H | H | H | $C_6H_5$ | 1 | 3 | $-NH_2$ |

*$R_2 + R_4 =$ ⬠

20

Examples 20 through 26: Isochromans and isothiochromans

Example 20:
4-(4-chlorophenyl)-1-[(3,4-dihydro-6,7-dimethoxy-4,4-dimethyl-1H-2-benzopyran-1-yl)methyl]-1,2,3,6-tetrahydropyridine, monohydrochloride.

A mixture of 1.52 g of 6,7-dimethoxy-4,4-dimethyl-1-bromomethylisochroman, 1.35 g of 4-(4-chlorophenyl)-1,2,3,6-tetrahydropyridine, and 2 ml. of triethylamine in 5 ml of DMF are heated at 50° C. for 23 hr. The mixture is partitioned between methylene chloride and aqueous potassium carbonate. The organic phase is dried over sodium sulfate and concentrated. The residue is chromatographed over silica gel utilizing 5% methanol/½% ammonium hydroxide/methylene chloride to give a 21% yield 4-(4-chloro phenyl)-1-[(3,4-dihydro-4,4-dimethyl-6,7-dimethoxy-1H-2-benzopyran-1-yl)methyl]-1,2,3,6-tetrahydropyridine.

The salt is prepared from hydrogen chloride in ether and recrystallized from ethanol/ethyl acetate, mp 250°–252°.

Anal. Calcd for $C_{25}H_{30}NO_3Cl.HCl$: Calcd: C, 64.65; H, 6.73; N, 3.01; Cl, 15.27 Found: C, 63.16; H, 6.78; N, 2.98; Cl, 14.87.

Example 21a:
1-Methyl-1-[3-(3,4-dihydro-6,7-dimethoxy-1H-2-benzopyran-1-yl)propyl]-4-(4-fluorophenyl)-piperazine, dihydrochloride.

A solution of 1-methyl-1-(3-chloropropyl)-3,4-dihydro-6,7-dimethoxy-1H-2-benzopyran (0.6 g., 0.002 mole), p-fluoropiperazine (0.4 g., 0.002 mole) and 0.5 g. of triethylamine in 10 ml. of ethylene glycol is heated to 80° C. under nitrogen for twenty hours. The reaction mixture is poured into water and extracted with methylene chloride. The methylene chloride solution is washed with water, a saturated solution of sodium chloride, dried over sodium sulfate and concentrated to an oil. The oil is chromatographed on a silica gel column using 5% methanol/methyl chloride as eluent to yield 500 mg. of 1-methyl-1-[3-(3,4-dihydro-6,7-dimethoxy-1H-2-benzopyran-1-yl)propyl]-4-(4-fluorophenyl)piperazine as a white oil. This is reacted with ethereal HCl and the product recrystallized from methanol/ether to yield 300 mg. of 1-methyl-1-[3-(3,4-dihydro-6,7-dimethoxy-1H-2-benzopuran-1-yl)propyl]-4-(4-fluorophenyl)piperazine, dihydrochloride, m.p. 240°–242° C.

Example 21b:
1-[2-(6,7-dimethoxy-4,4-dimethylisochroman-1-yl)ethyl]-4-(3-trifluoromethylphenyl)piperazine, dihydrochloride.

A mixture of 1.50 g. (0.0053 m) of 2-(6,7-dimethoxy-4,4-dimethyisochroman-1-yl)ethyl chloride, 2.48 g. (0.011 m) of 3-trifluoromethylphenylpiperazine and 30 ml of ethylene glycol is stirred at 55° for 24 hr. The mixture is partitioned between methylene chloride and sodium bicarbonate. The organic phase is concentrated and chromatographed. The salt of the title compound is prepared from ethereal hydrogen chloride. The yield is 0.83 g., mp 162°–163.5° C.

Anal. Calcd. for $C_{26}H_{23}N_2F_3O_3.2HCl$: Calcd: C, 56.62; H, 6.39; N, 5.08; Cl, 12.86; Found: C, 56.52; H, 6.52; N, 5.02; Cl, 11.25.

Example 21c:
2-[2-[(6,7-dimethoxy-4,4-dimethylisochroman-1-yl)ethyl]]6,7-dimethoxy-1,2,3,4-tetrahydroisoquinoline A mixture of 2.0 g of [2-(6,7-dimethoxy-4,4-dimethylisochroman-1-yl)ethyl]-[2-(3,4-dimethoxyphenyl)ethyl]amine, 500 mg of paraformaldehyde, 25 ml of toluene, and 10 ml of nitrobenzene is heated at 100° for 4 hours. The mixture is partitioned between methylene chloride and water. The organic phase is concentrated and chromatographed to yield the title compound which is converted to its hydrogen chloride salt and crystallized from ethyl acetate to give 800 mg of the title compound as its salt, mp 100°–105°.

Anal. Calcd. for $C_{26}H_{35}NO_5.HCl.1\frac{1}{2}H_2O$: Calcd: C, 61.82; H, 7.38; N, 2.77; Cl, 7.03; Found: C, 61.26; H, 7.30; N, 2.90; Cl, 7.03

In the manner of examples 20, 21a, and 21b, the following isochromans are prepared from the appropriate (6,7-dimethoxyisochroman-1-yl)alkyl halides and the appropriate amines. (Table 14).

TABLE 14

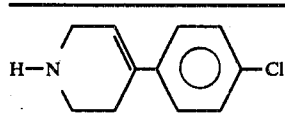

| HNR₉R₁₀ | n | R₂ | R₃ | R₈ | °C./Hrs | Misc. | M.P.(°C.) | Anal. (Found) | Name |
|---|---|---|---|---|---|---|---|---|---|
| 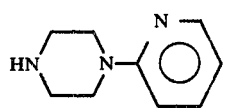 | 1 | CH₃ | CH₃ | H | 50°/23 | DMF Solvent | 250–252[a] | C, 63.16; H, 6.78; N, 2.98; Cl, 14.87 | 4-(4-chlorophenyl)-1-[(3,4-dihydro-4,4-dimethyl-6,7-dimethoxy-1H-2-benzopyran-1-yl)-methyl]-1,2,3,6-tetra-hydropyridine, monohydrochloride |
| 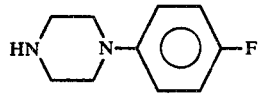 | 2 | CH₃ | CH₃ | H | 55°/24 | | 223° (decomp)[d] | C, 60.76; H, 7.77; N, 9.51; Cl, 14.37 | 1[2-(3,4-dihydro-4,4-dimethyl-6,7-dimethoxy-1H-2-benzopyran-1-yl)-ethyl]-4-(2-pyridyl)-piperazine, dihydrochloride |
| 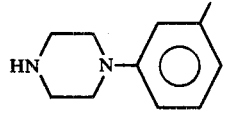 | 2 | CH₃ | CH₃ | H | 50°/15 | | 181–5° (dec)[a] | C, 61.37; H, 7.02; N, 5.93 | 1-[2-(3,4-dihydro-6,7-dimethoxy-1H-2-benzopyran-1-yl)ethyl]-4-(4-fluorophenyl)-piperazine, hydrochloride |
| 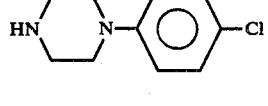 | 2 | CH₃ | CH₃ | H | 55°/18 | | 162–163.5[d] | C, 56.52; H, 6.52; N, 5.02 | 1-[2-(3,4-dihydro-6,7-dimethoxy-1H-2-benzopyran-1-yl)ethyl]-4-(3-trifluromethyl phenyl)-piperazine, dihydrochloride |
| 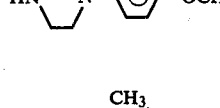 | 2 | CH₃ | CH₃ | H | 80°/20 | | 198–200 (dec)[b] | C, 61.22; H, 6.93; N, 5.75; Cl 15.24 | 4-(p-chlorophenyl)-1-[2-(4,4-dimethyl)-6,7-dimethoxy-1H-2-benzopyran-1-yl)ethyl]piperazine, monohydrochloride |
| 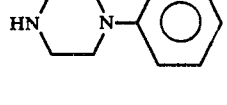 | 2 | CH₃ | CH₃ | H | 80°/20 | | 233–235 (dec)[d] | N, 62.28; H, 7.61; N, 5.48; Cl, 12.15 | 4-(p-methoxyphenyl)-1-[2-(4,4-dimethyl)-6,7-dimethoxy-1H-2-benzopyran-1-yl)ethyl]-piperazine, dihydrochloride |
| 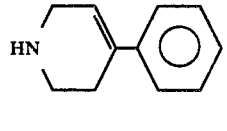 | 2 | CH₃ | CH₃ | H | 80°/20 | | 243–5 (dec)[a] | C, 67.29; H, 7.73; N, 6.10; Cl, 7.88 | 4-(o-tolyl)-1-[2(4,4-dimethyl)-6,7-dimethoxy-1H-2-benzopyran-1-yl)-ethyl]piperazine, monohydrochloride |
| 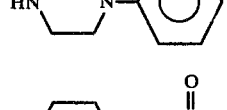 | 2 | CH₃ | CH₃ | H | 80°/20 | | 167–170[b] | C, 68.72; H, 7.50; N, 3.77; Cl, 8.44 | 4-phenyl-1-[2-(3,4-dihydro-4,4-dimethyl)-6,7-dimethoxy 1H-2-benzopyran-1-yl)ethyl 1,2,3,6-tetrahydropyridine monohydrochloride |
| 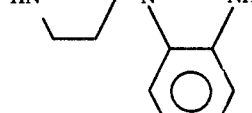 | 2 | CH₃ | CH₃ | H | 80°/20 | | 188–190[e] | C, 66.8; H, 8.26; N, 6.10 | 4-phenyl-1-[2-(3,4-dihydro-4,4-dimethyl-6,7-dimethoxy-1H-2-benzopyran-1-yl)-ethyl]piperazine |
| 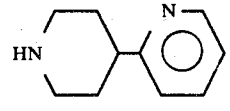 | 3 | H | H | CH₃ | 80°/20 | | | C, 69.63; H, 7.59; N, 8.81 | 1-[1-[3-(3,4-dihydro-6,7-dimethoxy-1-methyl-1H-2-benzopyran-1-yl)-propyl]-4-piperdinyl]-1,3-dihydro-2H-benzimidazol-2-one |
|  | 3 | H | H | CH₃ | 80°/20 | | 197–199 | as mono MeOH . 2HCl C, 58.31; H, 7.10; N, 8.14; Cl, 13.75; | 4-(2-pyridyl)-1-[3-(3,4-dihydro-1-methyl-6,7-dimethoxy-1H-2-benzopyran-1-yl)propyl]-piperidine |

TABLE 14-continued

Structure:
H3CO- and H3CO- substituted benzene ring fused with pyran, R2, R3, H, H, O, R8, (CH2)nNR9R10

| HNR9R10 | n | R2 | R3 | R8 | °C./Hrs | Misc. | M.P.(°C.) | Anal. (Found) | Name |
|---|---|---|---|---|---|---|---|---|---|
| HN-piperazine-N-(4-fluorophenyl) | 3 | H | H | 4-F-phenyl | 80°/20 | | 140–142[f] | C, 60.27; H, 5.92; H, 4.84; Cl, 6.15 | 4-(4-fluorophenyl)-1-[3-(3,4-dihydro-1-(4-fluorophenyl)-6,7-dimethoxy-1H-2-benzopyran-1-yl)-propyl]-piperazine |
| HN-piperazine-N-(2-methylphenyl) | 3 | H | H | 4-F-phenyl | 80°/20 | | 236–238[c] | C, 66.35; H, 7.34; N, 5.97; F, 3.33 | 4-(2-methylphenyl)-1-[3-(3,4-dihydro-1-(4-fluorophenyl)-6,7-dimethoxy-1H-2-benzopyran-1-yl)propyl]-piperazin |
| HN-tetrahydropyridine-phenyl | 3 | H | H | 4-F-phenyl | 80°/20 | nmr spectrum is consistent with assigned structure. | | | 4-(phenyl)-1-[3-(3,4-dihydro-1-(4-fluorophenyl)-6,7-dimethoxy-1H-2-benzopyran-1-yl)-propyl]-1,2,3,6-tetrahydropyridine |
| HN-piperazine-phenyl | 3 | H | H | 4-F-phenyl | 80°/20 | | 153–155[c] | C, 66.04; H, 6.49; H, 5.25; Cl, 6.67 | 1-[3-(3,4-dihydro-1-(4-fluorophenyl)-6,7-dimethoxy 1H-2-benzopyran-1-yl)propyl 4-phenylpiperazine |
| HN-piperidinyl-benzimidazol-2-one | 3 | H | H | 4-F-phenyl | 80°/20 | | 218–220° | C, 69.53; H, 6.31; N, 7.45; F, 3.29 | 1-[1-(3-(3,4-dihydro-6,7-dimethoxy-1-(4-fluorophenyl 1H-2-benzopyran-1-yl)propyl 4-piperidinyl]-1,3-dihydro-2H-benzimidazol-2-one |

[a] HCl salt.
[b] HCl salt hemihydrate
[c] HCl salt hydrate
[d] dihydrochloride salt
[e] dihydrate
[f] trihydrate hydrochloride

Example 22

Following procedures similar to those of Examples 20–21C, but substituting the appropriate (isochroman-1-yl)alkyl halides and the appropriate amines, the following compounds can be made.

TABLE 15

Structure with $R_1'$, $R_1''$, $R_1'''$, $R_1''''$, $R_2$, $R_3$, $R_4$, $R_5$, O, $R_8$, $(CH_2)_n NR_9R_{10}$

| $R_1'$ | $R_1''$ | $R_1'''$ | $R_1''''$ | $R_2$ | $R_3$ | $R_4$ | $R_5$ | $R_8$ | n | $NR_9R_{10}$ |
|---|---|---|---|---|---|---|---|---|---|---|
| H | H | propyl | —OCH3 | CH3 | H | H | H | H | 1 | NH(CH2)2-(3,4-dichlorophenyl) |

TABLE 15-continued
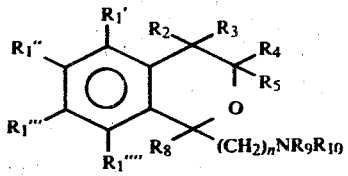
| R₁' | R₁'' | R₁''' | R₁'''' | R₂ | R₃ | R₄ | R₅ | R₈ | n | NR₉R₁₀ |
|---|---|---|---|---|---|---|---|---|---|---|
| H | H | H | —OCH₃ | CH₃ | H | H | H | H | 1 | 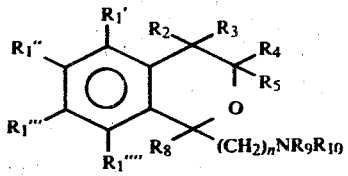 |
| OCH₃ | —OCH₃ | H | H | CH₃ | H | H | H | H | 1 | 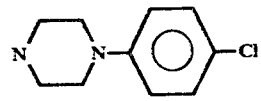 |
| H | OH | H | H | H | H | F | H | H | 4 | 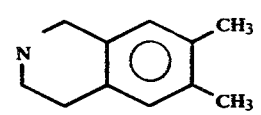 |
| H | OCH₃ | OCH₃ | H | CH₃ | CH₃ | H | H | H | 5 | 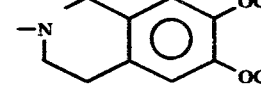 |
| H | OCH₃ | OCH₃ | H | H | H | CH₃ | CH₃ | H | 5 | 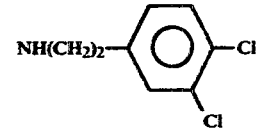 |
| H | OCH₃ | OCH₃ | H | 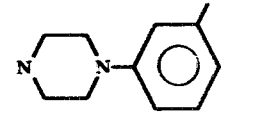 | | H | H | H | 5 |  |
| H | OC₃H₇ | OC₃H₇ | H | C₂H₅ | H | H | 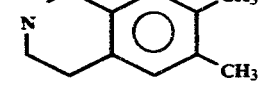 | H | 5 |  |
| H | H | OCH₃ | OCH₃ | C₃H₇ | H | | H | H | 2 | 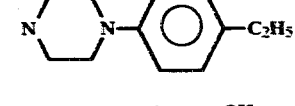 |
| H | OH | OH | H | C₃H₇ | H | C₃H₇ | H | H | 2 | 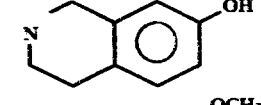 |
| H | OCH₃ | OCH₃ | CF₃ | C₃H₇ | H | H | H | H | 1 | 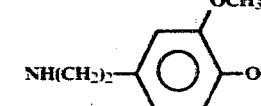 |
| H | —OCH₃ | —OCH₃ | H | C₃H₇ | H | H | H | H | 2 | 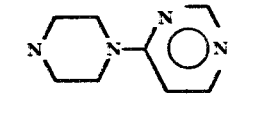 |
| H | —OCH₃ | OCH₃ | H | C₃H₇ | H | H | H | H | 2 | 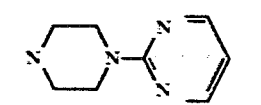 |

TABLE 15-continued
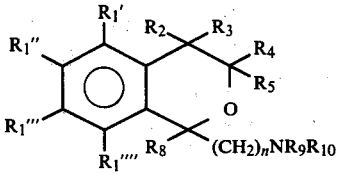
| R₁' | R₁'' | R₁''' | R₁'''' | R₂ | R₃ | R₄ | R₅ | R₈ | n | NR₉R₁₀ |
|---|---|---|---|---|---|---|---|---|---|---|
| H | —OCH₃ | —OCH₃ | H | CH₃ | H | H | H | H | 2 | 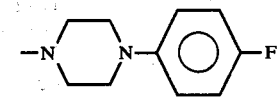 |
| H | OC₂H₅ | H | H | C₂H₅ | H | H | H | H | 1 | 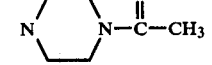 |
| H | OCH₃ | OCH₃ | OCH₃ | C₂H₅ | H | H | H | H | 1 | 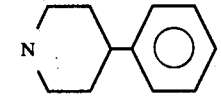 |
| —OCH₃ | —OH | H | H | C₂H₅ | H | H | H | H | 1 | 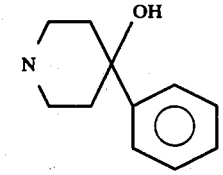 |
| H | —OCH₃ | Br | H | C₂H₅ | H | H | H | H | 1 | 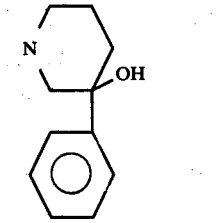 |
| H | —OCH₃ | Cl | Cl | C₂H₅ | H | H | H | H | 1 | 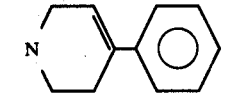 |
| H | —OCH₃ | —CF₃ | H | CH₃ | H | H | H | H | 2 | 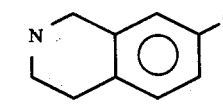 |
| H | O—CH₂—O | | H | H | H | H | H | H | 3 | 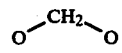 |
| H | OCH₃ | H | H | CH₃ | H | H | H | H | 3 | 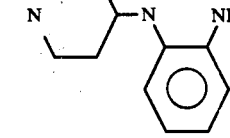 |
| H | OCH₃ | H | OCH₃ | CH₃ | H | CH₃ | H | H | 3 | 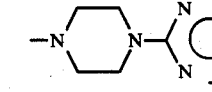 |
| H | OCH₃ | OCH₃ | OCH₃ | OCH₃ | H | OCH₃ | H | H | 4 | 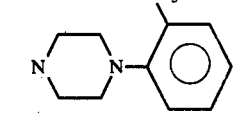 |

TABLE 15-continued

| R₁' | R₁'' | R₁''' | R₁'''' | R₂ | R₃ | R₄ | R₅ | R₈ | n | NR₉R₁₀ |
|---|---|---|---|---|---|---|---|---|---|---|
| H | H | H | OCH₃ | H | H | H | phenyl | H | 4 | 1-(2-methylphenyl)piperazine |
| H | OCH₃ | OCH₃ | H | CH₃ | H | H | H | H | 2 | 1-(3-fluorophenyl)piperazine |
| H | OCH₃ | OCH₃ | H | CH₃ | H | H | H | H | 2 | 1-(4-fluorophenyl)piperazine |
| H | OCH₃ | OCH₃ | H | CH₃ | H | H | H | H | 2 | 1-(2-methoxyphenyl)piperazine |
| H | OCH₃ | OCH₃ | H | C₂H₅ | H | H | H | H | 2 | 1-(2-methoxyphenyl)piperazine |
| H | —OCH₂O— | | H | C₂H₅ | H | H | H | H | 2 | 1-(2-methoxyphenyl)piperazine |
| H | —OCH₃ | —OCH₃ | H | C₃H₇ | H | H | H | H | 2 | 1-(2-methylphenyl)piperazine |
| H | OCH₃ | OCH₃ | H | CH₃ | H | H | H | H | 2 | 1-(2-methylphenyl)piperazine |
| H | OCH₃ | OCH₃ | H | CH₃ | H | CH₃ | H | H | 2 | 1-(2-methylphenyl)piperazine |
| H | OCH₃ | OCH₃ | H | OCH₃ | H | OCH₃ | H | H | 2 | 1-(2-(2-oxo-2,3-dihydro-1H-benzimidazol-1-yl))piperidine |
| H | OCH₃ | OCH₃ | H | H | H | H | phenyl | H | 2 | 6,7-dimethoxy-1,2,3,4-tetrahydroisoquinoline |

TABLE 15-continued

[Structure: cyclohexane ring with substituents $R_1'$, $R_1''$, $R_1'''$, $R_1''''$, $R_2$, $R_3$, $R_4$, $R_5$, $R_8$, and $-O-C(CH_2)_nNR_9R_{10}$ group]

| $R_1'$ | $R_1''$ | $R_1'''$ | $R_1''''$ | $R_2$ | $R_3$ | $R_4$ | $R_5$ | $R_8$ | n | $NR_9R_{10}$ |
|---|---|---|---|---|---|---|---|---|---|---|
| H | OCH₃ | OCH₃ | H | phenyl | H | F | H | H | 2 | 6,7-dimethoxy-1,2,3,4-tetrahydroisoquinolin-2-yl |
| H | OCH₃ | OCH₃ | H | CH₃ | CH₃ | H | H | H | 2 | 4-(pyrimidin-2-yl)piperazin-1-yl |
| H | OCH₃ | OCH₃ | H | phenyl | H | CH₃ | CH₃ | CH₃ | 2 | 4-(4-hydroxypyrimidin-2-yl)piperazin-1-yl |
| H | —OCH₃ | OCH₃ | H | cyclopentyl | | H | H | CH₃ | 2 | 4-(4-hydroxypyrimidin-2-yl)piperazin-1-yl |
| H | —OCH₃ | —OCH₃ | H | CH₃ | H | cyclopropyl | H | CH₃ | 2 | 4-(6-hydroxypyridazin-3-yl)piperazin-1-yl |
| H | —OCH₃ | —OCH₃ | H | H | H | cyclopentyl | H | CH₃ | 3 | 4-(4-fluorophenyl)piperazin-1-yl |
| H | —OCH₃ | —OCH₃ | H | C₂H₅ | H | C₃H₇ | H | CH₃ | 2 | 4-(4-fluorophenyl)piperazin-1-yl |
| H | OCH₃ | OCH₃ | H | H | H | H | H | CH₃ | 2 | 4-methyl-4'-(4-fluorophenyl)piperazin-1-yl |
| H | OCH₃ | OCH₃ | H | H | H | H | H | CH₃ | 2 | 4-(2-methoxyphenyl)piperazin-1-yl |
| H | OCH₃ | OCH₃ | H | H | H | H | H | CH₃ | 2 | 4-methyl-4'-(2-methoxyphenyl)piperazin-1-yl |
| H | OCH₃ | OCH₃ | H | H | H | H | H | CH₃ | 2 | 4-methyl-4'-(2-methoxyphenyl)piperazin-1-yl |
| H | OCH₃ | OCH₃ | H | H | H | H | H | CH₃ | 3 | 4-(2-methylphenyl)piperazin-1-yl |

TABLE 15-continued

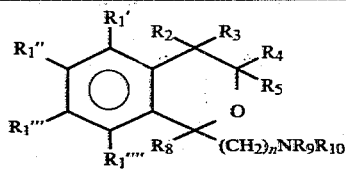

| R₁' | R₁" | R₁'" | R₁"" | R₂ | R₃ | R₄ | R₅ | R₈ | n | NR₉R₁₀ |
|---|---|---|---|---|---|---|---|---|---|---|
| H | OCH₃ | OCH₃ | H | H | H | H | H | CH₃ | 4 | 4-(2-oxo-benzimidazol-1-yl)piperidin-1-yl |
| H | OCH₃ | OCH₃ | H | H | H | H | H | CH₃ | 2 | 6,7-dimethoxy-1,2,3,4-tetrahydroisoquinolin-2-yl |
| H | OCH₃ | OCH₃ | H | H | H | H | H | CH₃ | 2 | 6,7-dimethoxy-1,2,3,4-tetrahydroisoquinolin-2-yl |
| H | OCH₃ | OCH₃ | H | H | H | H | H | CH₃ | 2 | 6,7-dimethoxy-1,2,3,4-tetrahydroisoquinolin-2-yl |
| H | —O—CH₂—O— | | H | H | H | H | H | 4-F-C₆H₄ | 2 | 4-(4-fluorophenyl)piperazin-1-yl |
| H | OCH₃ | OCH₃ | H | CH₃ | H | H | H | 4-F-C₆H₄ | 2 | 4-(4-fluorophenyl)piperazin-1-yl |
| H | OCH₃ | OCH₃ | H | CH₃ | H | CH₃ | H | 4-F-C₆H₄ | 2 | 4-(4-fluorophenyl)piperazin-1-yl |
| H | OCH₃ | OCH₃ | H | OCH₃ | H | OCH₃ | H | 4-F-C₆H₄ | 2 | 4-(2-methoxyphenyl)piperazin-1-yl |
| H | OCH₃ | OCH₃ | H | H | H | H | C₆H₅ | 4-F-C₆H₄ | 2 | 4-(2-methoxyphenyl)piperazin-1-yl |
| H | OCH₃ | OCH₃ | H | H | H | Cl | H | 4-F-C₆H₄ | 2 | 4-(2-methoxyphenyl)piperazin-1-yl |
| H | OCH₃ | OCH₃ | H | CH₃ | CH₃ | H | H | 4-F-C₆H₄ | 2 | 4-(2-methylphenyl)piperazin-1-yl |
| H | OCH₃ | OCH₃ | H | H | H | CH₃ | CH₃ | C₆H₅ | 2 | 4-(2-methylphenyl)piperazin-1-yl |

TABLE 15-continued
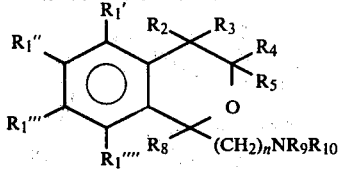
| $R_1'$ | $R_1''$ | $R_1'''$ | $R_1''''$ | $R_2$ | $R_3$ | $R_4$ | $R_5$ | $R_8$ | n | $NR_9R_{10}$ |
|---|---|---|---|---|---|---|---|---|---|---|
| H | $OCH_3$ | $OCH_3$ | H | $CH_3$ | H | H | H |  | 2 |  |
| H | $OCH_3$ | $OCH_3$ | H | $C_2H_5$ | $C_2H_5$ | H | H |  | 2 |  |
| H | $OCH_3$ | $OCH_3$ | H | H | H |  | H |  | 2 |  |
| H | $OCH_3$ | $OCH_3$ | H | H | H | $C_3H_7$ | H |  | 2 |  |
| H | $OCH_3$ | $OCH_3$ | H | $CH_3$ | $CH_3$ | H | H | $CH_3$ | 3 |  |
| H | H | H | $-OCH_3$ | $C_2H_5$ | $C_2H_5$ | H | H | H | 3 |  |
| H | $OCH_3$ | $OCH_3$ | H | $C_3H_7$ | $C_3H_7$ | H | H | H | 3 | |
| H | $OC_2H_5$ | H | H | $CH_3$ | $C_2H_5$ | H | H | $CH_3$ | 2 | |
| OH | H | H | H | $C_2H_5$ | $C_3H_7$ | H | H | H | 3 | |
| H | $OCH_3$ | $OCH_3$ | H | $OCH_3$ | H | H | H | H | 2 | |
| H | $OCH_3$ | $OCH_3$ | H | Cl | H | H | H | H | 1 | |

TABLE 15-continued

| $R_1'$ | $R_1''$ | $R_1'''$ | $R_1''''$ | $R_2$ | $R_3$ | $R_4$ | $R_5$ | $R_8$ | n | $NR_9R_{10}$ |
|---|---|---|---|---|---|---|---|---|---|---|
| H | $OCH_3$ | $CF_3$ | H | H | H | H | H | $CH_3$ | 3 | 6,7-dimethoxy-1,2,3,4-tetrahydroisoquinolin-2-yl |
| H | —O—CH$_2$—O— (on $R_1''$, $R_1'''$) | | H | cyclohexyl | H | H | H | H | 1 | 1-(2-oxo-2,3-dihydro-1H-benzimidazol-1-yl)piperidin-4-yl (acetyl) |
| H | $OCH_3$ | $OCH_3$ | H | $CH_3$ | H | H | H | H | 1 | 4-(pyridin-4-yl)piperazin-1-yl |
| H | $OCH_3$ | H | H | H | H | H | H | $CH_3$ | 2 | $NH(CH_2)_2$-(3,4-dichlorophenyl) |
| H | —$OCH_3$ | H | H | H | H | H | $OCH_3$ | H | 2 | 4-(4-chlorophenyl)piperazin-1-yl |
| H | —$OCH_3$ | $OCH_3$ | H | H | H | $OCH_3$ | $CH_3$ | H | 2 | 6,7-dimethyl-1,2,3,4-tetrahydroisoquinolin-2-yl |
| H | $OC_2H_5$ | H | H | H | $OCH_3$ | $CH_3$ | Cl | H | 2 | 4-acetylpiperazin-1-yl |
| H | —$OCH_3$ | $OCH_3$ | $OCH_3$ | H | $CH_3$ | Cl | H | H | 2 | 4-phenylpiperidin-1-yl |
| H | —$OCH_3$ | H | H | $CH_3$ | Cl | H | H | H | 3 | 4-hydroxy-4-phenylpiperidin-1-yl |
| H | $OCH_3$ | H | H | Cl | H | H | H | H | 3 | 4-(4-chlorophenyl)piperidin-1-yl |
| H | $OCH_3$ | Cl | H | $CH_3$ | $CF_3$ | H | H | $CH_3$ | 2 | 4-phenylpiperidin-1-yl |
| H | $OCH_3$ | $OCH_3$ | H | $CH_3$ | H | H | H | H | 2 | 4-(4-chlorophenyl)piperazin-1-yl |

TABLE 15-continued

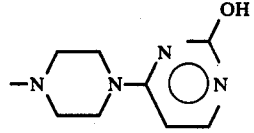

| R₁' | R₁'' | R₁''' | R₁'''' | R₂ | R₃ | R₄ | R₅ | R₈ | n | NR₉R₁₀ |
|---|---|---|---|---|---|---|---|---|---|---|
| H | H | OCH₃ | H | CH₃ | H | CH₃ | H | CH₃ | 5 | 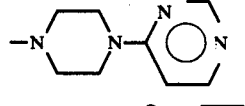 |
| H | —CH₃ | H | H | OCH₃ | H | OCH₃ | H | CH₃ | 5 |  |
| H | H | H | OCH₃ | H | H | H | ⌬ | CH₃ | 3 | 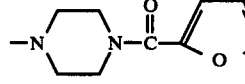 |
| H | —OCH₃ | H | H | H | H | Br | H | H | 3 | 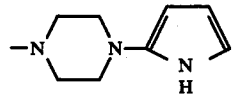 |
| H | OCH₃ | OCH₃ | H | CH₃ | CH₃ | H | H | H | 4 | 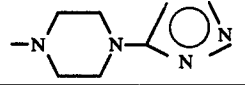 |

Example 23

Following procedures similar to those in Examples 20–22, but substituting the appropriate [isochroman-1-yl]alkyl halides and the appropriate amines, the following compounds are made.

TABLE 16

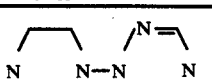

| R₁' | R₁'' | R₁''' | R₁'''' | R₂ | R₃ | R₄ | R₅ | R₈ | Branch Chain | NR₉R₁₀ |
|---|---|---|---|---|---|---|---|---|---|---|
| H | C₃H₇ | C₃H₇ | OCH₃ | CH₃ | H | H | H | H | $\begin{array}{c}CH_3\\|\\ -C-CH_2\\|\\ CH_3\end{array}$ | 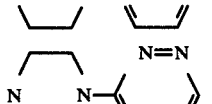 |
| H | H | H | OCH₃ | CH₃ | CH₃ | H | H | H | $\begin{array}{c}CH_3\ \ CH_3\\|\ \ \ \ \ |\\ -C-\!-\!C-CH_2\\|\ \ \ \ \ |\\ CH_3\ \ CH_3\end{array}$ | 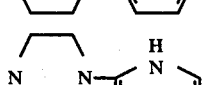 |
| OCH₃ | OCH₃ | H | H | H | H | CH₃ | CH₃ | H | $\begin{array}{c}-C-CH_2-CH_2-CH_2\\|\\ C_2H_5\ \ \ \ \ \ \ C_2H_5\end{array}$ | 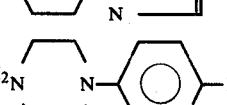 |
| H | OC₂H₅ | H | H | CH₃ | H | H | H | H | $\begin{array}{c}\ \ \ \ \ \ \ \ \ \ \ C_2H_5\\ -C-CH_2-C-CH_2CH_2\!-\\|\ \ \ \ \ \ \ \ \ \ \ |\\ CH_3\ \ \ \ \ CH_3\ \ C_2H_5\end{array}$ | 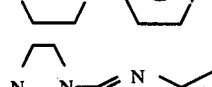 |
| H | OCH₃ | OCH₃ | OCH₃ | CH₃ | CH₃ | H | H | H | $\begin{array}{c}C_2H_5\\|\\ -C-CH_2\\|\\ C_2H_5\end{array}$ | (structure) |

TABLE 16-continued

| R₁' | R₁'' | R₁''' | R₁'''' | R₂ | R₃ | R₄ | R₅ | R₈ | Branch Chain | NR₉R₁₀ |
|---|---|---|---|---|---|---|---|---|---|---|
| H | OH | OCH₃ | H | CH₃ | H | H | H | H | —CH₂—C(C₂H₅)(C₂H₅)—CH₂— | 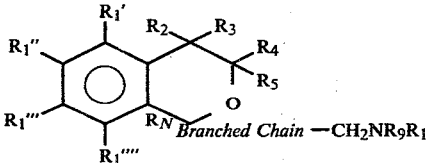 |
| H | OCH₃ | Br | H | CH₃ | H | CH₃ | H | H | —C(CH₃)(CH₃)—CH₂—CH₂ | 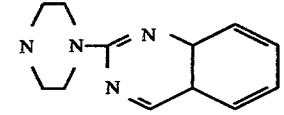 |
| H | OCH₃ | Cl | Cl | C₂H₅ | C₂H₅ | H | H | H | CH₃—C(CH₃)—CH₂—C(CH₃)—CH₂ | 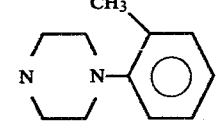 |
| H | OCH₃ | CF₃ | H | CH₃ | CH₃ | H | H | H | C(C₂H₅)(H)—C(CH₃)(H)—CH₂ | NH(CH₂)₂—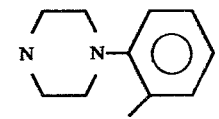 |
| H | H—CH₂—O | H | H | cyclopentyl | H | H | H | H | C(C₂H₅)(C₂H₅)—CH₂—CH(C₂H₅)—CH₂ | 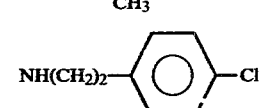 |
| H | OCH₃ | H | H | H | cyclopentyl | H | H | H | C(CH₃)(CH₃)—CH₂—C(C₂H₅)(H)—CH₂ | 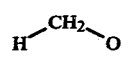 |
| H | OCH₃ | H | OCH₃ | CH₃ | CH₃ | H | H | H | —C(CH₃)(CH₃)—CH₂CH₂CH₂ |  |
| H | OCH₃ | OCH₃ | OCH₃ | H | H | CH₃ | CH₃ | H | CH(CH₃)—CH₂C(CH₃)—CH₂—CH₂ | 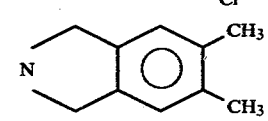 |
| H | H | H | OCH₃ | H | H | CH₃ | H | H | —CH₂—C(CH₃)(CH₃)—CH₂CH₂ |  |
| H | OC₃H₇ | OC₃H₇ | H | H | H | CH₃ | H | F-phenyl | —CH₂—CH₂—C(CH₃)(C₂H₅)—CH₂— | 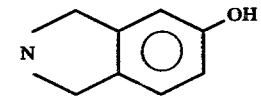 |
| H | OH | H | H | C₂H₅ | H | H | H | H | —CH₂—CH(CH₃)(C₂H₅)—CH₂CH | 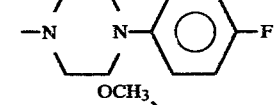 |

TABLE 16-continued

Structure:
Benzene ring with substituents $R_1'$, $R_1''$, $R_1'''$, $R_1''''$, $R_2$, $R_3$, $R_4$, $R_5$, $R_8$, with branched chain —$CH_2NR_9R_{10}$ and O linkage.

| $R_1'$ | $R_1''$ | $R_1'''$ | $R_1''''$ | $R_2$ | $R_3$ | $R_4$ | $R_5$ | $R_8$ | Branch Chain | $NR_9R_{10}$ |
|---|---|---|---|---|---|---|---|---|---|---|
| H | OCH₃ | OCH₃ | H | cyclopentyl | H | H | H | CH₃ | —CH(CH₃)—CH₂—CH(CH₃)—CH₂— | —N(piperazine)—N—C₆H₄—F |
| H | OCH₃ | OCH₃ | H | cyclohexyl | H | H | H | CH₃ | —CH₂CH(CH₃) CH(CH₃)CH₂— | —N—piperidine—C₆H₄—Cl with OH |
| H | OCH₃ | OCH₃ | H | CH₃ | H | H | H | CH₃ | CH₂—CH(C₂H₅)—CH₂ | —N(piperazine)—N—C₆H₄—Br |

Example 24

Following the procedures described in Preparation 8, and in Examples 13 through 18, but substituting either the appropriate isochroman-1-yl alcohols or [isochroman-1-yl]alkoxyalkyl chlorides, or [isochroman-1-yl]alkoxyalkyl benzenesulfonates, the following compounds are made (Table 17).

TABLE 17

Structure: Benzene ring with substituents $R_1'$, $R_1''$, $R_1'''$, $R_1''''$, $R_2$, $R_3$, $R_4$, $R_5$, $R_8$, and side chain —$(CH_2)_m$—$(OCH_2CH_2)_q$—$NR_{21}R_{22}$ with O linkage.

| $R_1'$ | $R_1''$ | $R_1'''$ | $R_1''''$ | $R_2$ | $R_3$ | $R_4$ | $R_5$ | $R_8$ | m | q | $NR_{21}R_{22}$ |
|---|---|---|---|---|---|---|---|---|---|---|---|
| H | H | propyl | —OCH₃ | H | H | H | H | H | 1 | 1 | NH(CH₂)₂—C₆H₃(Cl)(Cl) |
| H | H | H | —OCH₃ | H | H | H | H | H | 1 | 2 | piperazinyl—C₆H₄—Cl |
| OCH₃ | OCH₃ | H | H | H | H | H | H | H | 1 | 3 | tetrahydroisoquinolinyl with two CH₃ |
| H | OC₂H₅ | H | H | H | H | H | H | H | 2 | 1 | piperazinyl—C(=O)—CH₃ |
| H | OCH₃ | OCH₃ | OCH₃ | H | H | H | H | H | 2 | 2 | tetrahydropyridinyl—C₆H₅ |
| —OCH₃ | —OH | H | H | H | H | H | H | H | 2 | 3 | piperidinyl(OH)(C₆H₅) |

TABLE 17-continued

Structure:
$R_1''-$ cyclohexane ring with $R_1'$, $R_1'''$, $R_1''''$, $R_8$ substituents, bearing $-C(R_2)(R_3)-C(R_4)(R_5)-O-$ and $-(CH_2)_m-(OCH_2CH_2)_q-NR_{21}R_{22}$

| $R_1'$ | $R_1''$ | $R_1'''$ | $R_1''''$ | $R_2$ | $R_3$ | $R_4$ | $R_5$ | $R_8$ | m | q | $NR_{21}R_{22}$ |
|---|---|---|---|---|---|---|---|---|---|---|---|
| H | —OCH₃ | Br | H | H | H | H | H | H | 3 | 1 | 4-hydroxy-4-phenylpiperidinyl |
| H | —OCH₃ | Cl | Cl | H | H | H | H | H | 3 | 2 | 4-(4-fluorophenyl)piperazinyl |
| H | —OCH₃ | —CF₃ | H | H | H | H | H | H | 3 | 3 | 7-chloro-1,2,3,4-tetrahydroisoquinolin-2-yl |
| H | —O—CH₂—O— (on $R_1''$/$R_1'''$) | | H | H | H | H | H | H | 1 | 1 | 1-(2-oxo-2,3-dihydro-1H-benzimidazol-1-yl)piperidin-4-yl |
| H | —OCH₃ | H | H | CH₃ | H | H | H | H | 2 | 1 | 4-(pyrimidin-2-yl)piperazinyl |
| H | OCH₃ | H | OCH₃ | CH₃ | H | CH₃ | H | H | 3 | 2 | 4-(2-methylphenyl)piperazinyl |
| H | OCH₃ | OCH₃ | OCH₃ | OCH₃ | H | OCH₃ | H | H | 2 | 3 | 4-(4-fluorophenyl)piperazinyl |
| H | H | H | OCH₃ | H | H | H | C₆H₅ | H | 1 | 3 | 4-(2-methoxyphenyl)piperazinyl |
| H | OH | H | H | H | H | F | H | H | 1 | 1 | 6,7-dimethoxy-1,2,3,4-tetrahydroisoquinolin-2-yl |
| H | OCH₃ | OCH₃ | H | CH₃ | CH₃ | H | H | H | 2 | 2 | —NH(CH₂)₂-(3,4-dichlorophenyl) |
| H | OCH₃ | OCH₃ | H | H | H | CH₃ | CH₃ | H | 3 | 3 | 4-(3-bromophenyl)piperazinyl |
| H | OCH₃ | OCH₃ | H | cyclopentyl (R₂/R₃) | | H | H | H | 3 | 1 | 6,7-dimethyl-1,2,3,4-tetrahydroisoquinolin-2-yl |

TABLE 17-continued

Structure:

$$R_1''' \text{-benzene ring with } R_1', R_1'', R_1''''', R_2, R_3, R_4, R_5, R_8 \text{ substituents; } -O-(CH_2)_m-(OCH_2CH_2)_q-NR_{21}R_{22}$$

| $R_1'$ | $R_1''$ | $R_1'''$ | $R_1''''$ | $R_2$ | $R_3$ | $R_4$ | $R_5$ | $R_8$ | m | q | $NR_{21}R_{22}$ |
|---|---|---|---|---|---|---|---|---|---|---|---|
| H | OC$_3$H$_7$ | OC$_3$H$_7$ | H | H | H | cyclobutyl | H | H | 1 | 1 | piperazinyl-phenyl-C$_2$H$_5$ |
| H | H | OCH$_3$ | OCH$_3$ | H | H | cyclopentyl | H | H | 1 | 1 | 7-hydroxy-1,2,3,4-tetrahydroisoquinolinyl |
| H | OH | OH | H | H | H | C$_3$H$_7$ | H | H | 1 | 1 | NH(CH$_2$)$_2$-(3,4-dimethoxyphenyl) |
| H | —OCH$_3$ | —OCH$_3$ | H | H | H | CH$_3$ | H | CH$_3$ | 1 | 3 | —N(CH$_3$)$_2$ |
| H | —OCH$_3$ | —OCH$_3$ | H | C$_2$H$_5$ | H | H | H | CH$_3$ | 1 | 4 | morpholino |
| H | -OCH$_3$ | -OCH$_3$ | H | cyclopentyl | H | H | H | CH$_3$ | 1 | 4 | -N-H butyl |
| H | OCH$_3$ | -OCH$_3$ | H | cyclohexyl | H | H | H | CH$_3$ | 2 | 3 | piperazinyl-phenyl-F |
| H | OCH$_3$ | OCH$_3$ | H | CH$_3$ | H | H | H | C$_6$H$_5$ | 1 | 3 | -NH-$\underline{t}$-butyl |
| H | OCH$_3$ | OCH$_3$ | H | H | H | CH$_3$ | H | C$_6$H$_5$ | 1 | 3 | -NH$_2$ |

Example 25:
4-(4-Chlorophenyl)-1-[2-(3,4-dihydro-4,4-dimethyl-6,7-dimethoxy-1H-2-benzothiopyran-1-yl)-methyl]-1,2,3,6-tetrahydropyridine, monohydrochloride.

A mixture of 4-(4-chlorophenyl)-1,2,3,6-tetrahydropyridine and (3,4-dihydro-4,4-dimethyl-6,7-dimethoxy-1H-2-benzothiopyran-1-yl)methyl chloride are heated in toluene. The mixture is partitioned between methyline chloride and sodium carbonate. The product stated above is isolated from the organic phase by chromatography and crystallization.

Example 26

Following the procedures similar to those used in Examples 20–22 and 25, but substituting the appropriate (Isothiochroman-1-yl)alkyl halide for (isochroman-1-yl)alkyl halide and the appropriate amines, the following compounds can be prepared (Table 18).

TABLE 18

Structure: benzene ring with $R_1'$, $R_1''$, $R_1'''$, $R_1''''$, $R_2$, $R_3$, $R_4$, $R_5$, $R_8$ substituents; S in ring; $-(CH_2)_n NR_9R_{10}$

| $R_1'$ | $R_1''$ | $R_1'''$ | $R_1''''$ | $R_2$ | $R_3$ | $R_4$ | $R_5$ | $R_8$ | n | $NR_9R_{10}$ |
|---|---|---|---|---|---|---|---|---|---|---|
| H | H | propyl | —OCH$_3$ | CH$_3$ | H | H | H | H | 1 | NH(CH$_2$)$_2$-(3,4-dichlorophenyl) |
| H | H | H | —OCH$_3$ | CH$_3$ | H | H | H | H | 1 | piperazinyl-(4-chlorophenyl) |
| OCH$_3$ | —OCH$_3$ | H | H | CH$_3$ | H | H | H | H | 1 | 6,7-dimethyl-1,2,3,4-tetrahydroisoquinolinyl |

TABLE 18-continued
| R1' | R1'' | R1''' | R1'''' | R2 | R3 | R4 | R5 | R8 | n | NR9R10 |
|---|---|---|---|---|---|---|---|---|---|---|
| H | OH | H | H | H | H | F | H | H | 4 | 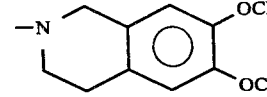 |
| H | OCH3 | OCH3 | H | CH3 | CH3 | H | H | H | 5 | 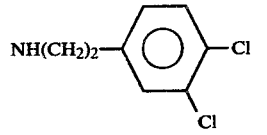 |
| H | OCH3 | OCH3 | H | H | H | CH3 | CH3 | H | 5 | 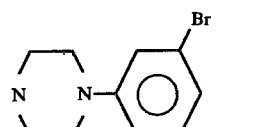 |
| H | OCH3 | OCH3 | H |  | | H | H | H | 5 | 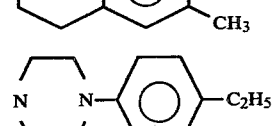 |
| H | OC3H7 | OC3H7 | H | C2H5 | H | H |  | H | 5 | 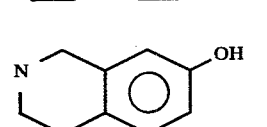 |
| H | H | OCH3 | OCH3 | C3H7 | H | | H | H | 2 | 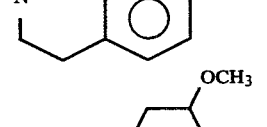 |
| H | OH | OH | H | C3H7 | H | C3H7 | H | H | 2 | 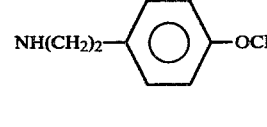 |
| H | OCH3 | OCH3 | CF3 | C3H7 | H | H | H | H | 1 | 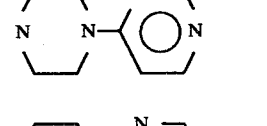 |
| H | —OCH3 | —OCH3 | H | C3H7 | H | H | H | H | 2 | 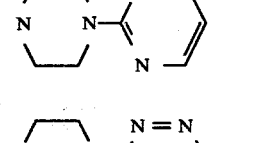 |
| H | —OCH3 | OCH3 | H | C3H7 | H | H | H | H | 2 | 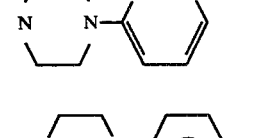 |
| H | —OCH3 | —OCH3 | H | CH3 | H | H | H | H | 2 | 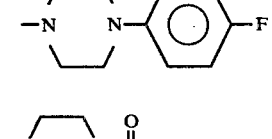 |
| H | OC2H5 | H | H | C2H5 | H | H | H | H | 1 | 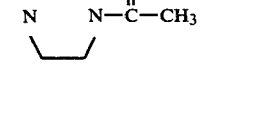 |

TABLE 18-continued
| R1' | R1" | R1''' | R1'''' | R2 | R3 | R4 | R5 | R8 | n | NR9R10 |
|---|---|---|---|---|---|---|---|---|---|---|
| H | OCH3 | OCH3 | OCH3 | C2H5 | H | H | H | H | 1 | 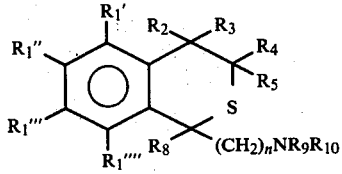 |
| —OCH3 | —OH | H | H | C2H5 | H | H | H | H | 1 | 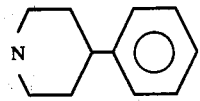 |
| H | —OCH3 | Br | H | C2H5 | H | H | H | H | 1 | 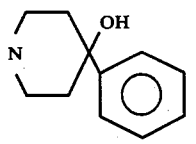 |
| H | —OCH3 | Cl | Cl | C2H5 | H | H | H | H | 1 | 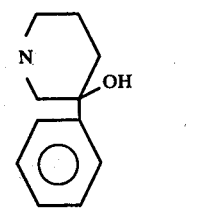 |
| H | —OCH3 | —CF3 | H | CH3 | H | H | H | H | 2 | 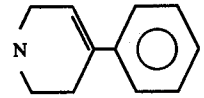 |
| H | \<—OCH2O—\> | | H | H | H | H | H | H | 3 | 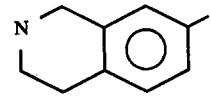 |
| H | OCH3 | H | H | CH3 | H | H | H | H | 3 | 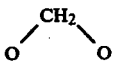 |
| H | OCH3 | H | OCH3 | CH3 | H | CH3 | H | H | 3 | 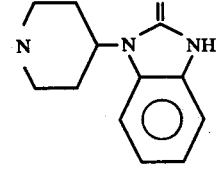 |
| H | OCH3 | OCH3 | OCH3 | OCH3 | H | OCH3 | H | H | 4 | 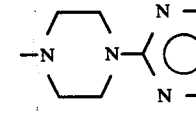 |
| H | H | H | OCH3 | H | H | H | 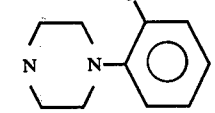 | H | 4 | 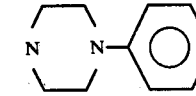 |

TABLE 18-continued
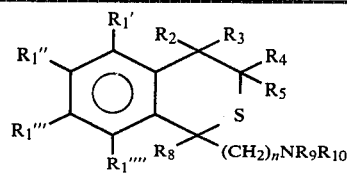
| R$_1$' | R$_1$'' | R$_1$''' | R$_1$'''' | R$_2$ | R$_3$ | R$_4$ | R$_5$ | R$_8$ | n | NR$_9$R$_{10}$ |
|---|---|---|---|---|---|---|---|---|---|---|
| H | OCH$_3$ | OCH$_3$ | H | CH$_3$ | H | H | H | H | 2 | 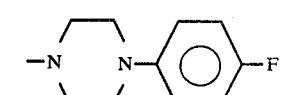 |
| H | OCH$_3$ | OCH$_3$ | H | CH$_3$ | H | H | H | H | 2 | 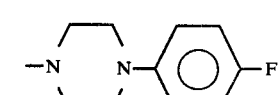 |
| H | OCH$_3$ | OCH$_3$ | H | CH$_3$ | H | H | H | H | 2 | 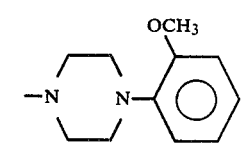 |
| H | OCH$_3$ | OCH$_3$ | H | C$_2$H$_5$ | H | H | H | H | 2 | 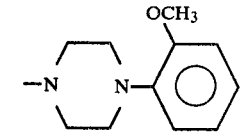 |
| H | —OCH$_2$O— | | H | C$_2$H$_5$ | H | H | H | H | 2 | 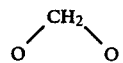 |
| H | —OCH$_3$ | —OCH$_3$ | H | C$_3$H$_7$ | H | H | H | H | 2 | 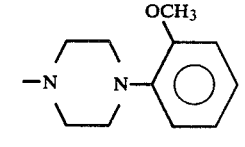 |
| H | OCH$_3$ | OCH$_3$ | H | CH$_3$ | H | H | H | H | 2 | 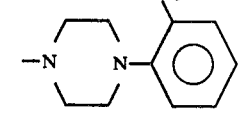 |
| H | OCH$_3$ | OCH$_3$ | H | CH$_3$ | H | CH$_3$ | H | H | 2 | 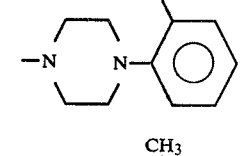 |
| H | OCH$_3$ | OCH$_3$ | H | OCH$_3$ | H | OCH$_3$ | H | H | 2 | 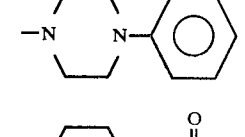 |
| H | OCH$_3$ | OCH$_3$ | H | H | H | H | 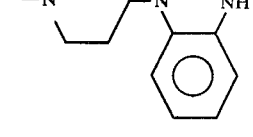 | H | 2 |  |

TABLE 18-continued

| R₁' | R₁'' | R₁''' | R₁'''' | R₂ | R₃ | R₄ | R₅ | R₈ | n | NR₉R₁₀ |
|---|---|---|---|---|---|---|---|---|---|---|
| H | OCH₃ | OCH₃ | H | phenyl | H | F | H | H | 2 | 6,7-dimethoxy-1,2,3,4-tetrahydroisoquinolin-2-yl |
| H | OCH₃ | OCH₃ | H | CH₃ | CH₃ | H | H | H | 2 | 4-(1,3,5-triazin-2-yl)piperazin-1-yl |
| H | OCH₃ | OCH₃ | H | phenyl | H | CH₃ | CH₃ | CH₃ | 2 | 4-(4-hydroxypyrimidin-2-yl)piperazin-1-yl |
| H | —OCH₃ | OCH₃ | H | cyclopentyl | | H | H | CH₃ | 2 | 4-(6-hydroxypyrimidin-2-yl)piperazin-1-yl |
| H | —OCH₃ | —OCH₃ | H | CH₃ | H | cyclobutyl | H | CH₃ | 2 | 4-(6-hydroxypyridazin-3-yl)piperazin-1-yl |
| H | —OCH₃ | —OCH₃ | H | H | H | cyclopentyl | H | CH₃ | 3 | 4-(4-fluorophenyl)piperazin-1-yl |
| H | —OCH₃ | —OCH₃ | H | C₂H₅ | H | C₃H₇ | H | CH₃ | 2 | 4-(4-fluorophenyl)piperazin-1-yl |
| H | OCH₃ | OCH₃ | H | CH₃ | H | CH₃ | H | 4-fluorophenyl | 2 | 4-(4-fluorophenyl)piperazin-1-yl |
| H | OCH₃ | OCH₃ | H | OCH₃ | H | OCH₃ | H | 4-fluorophenyl | 2 | 4-(2-methoxyphenyl)piperazin-1-yl |
| H | OCH₃ | OCH₃ | H | H | H | H | phenyl | 4-fluorophenyl | 2 | 4-(2,6-dimethoxyphenyl)piperazin-1-yl |
| H | OCH₃ | OCH₃ | H | H | H | Cl | H | 4-fluorophenyl | 2 | 4-(2-methoxyphenyl)piperazin-1-yl |

TABLE 18-continued
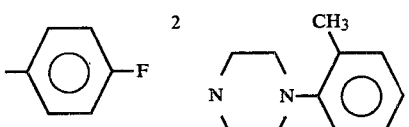
| $R_1{}'$ | $R_1{}''$ | $R_1{}'''$ | $R_1{}''''$ | $R_2$ | $R_3$ | $R_4$ | $R_5$ | $R_8$ | n | $NR_9R_{10}$ |
|---|---|---|---|---|---|---|---|---|---|---|
| H | $OCH_3$ | $OCH_3$ | H | $CH_3$ | $CH_3$ | H | H | 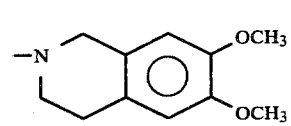 | 2 | 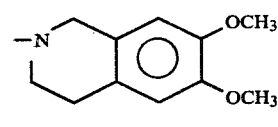 |
| H | $OCH_3$ | $OCH_3$ | H | H | H | H | H | $CH_3$ | 2 | 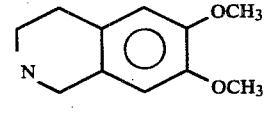 |
| H | $OCH_3$ | $OCH_3$ | H | H | H | H | H | $CH_3$ | 2 | 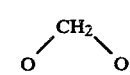 |
| H | $OCH_3$ | $OCH_3$ | H | H | H | H | H | $CH_3$ | 2 | 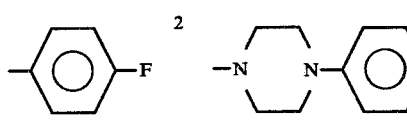 |
| H | \multicolumn{2}{c}{$-O-CH_2-O-$} | H | H | H | H | H | 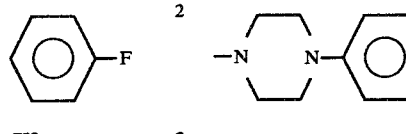 | 2 | 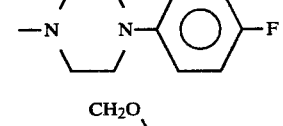 |
| H | $OCH_3$ | $OCH_3$ | H | $CH_3$ | H | H | H | 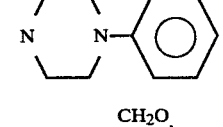 | 2 | 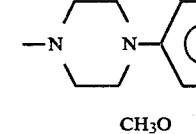 |
| H | $OCH_3$ | $OCH_3$ | H | H | H | H | H | $CH_3$ | 2 | 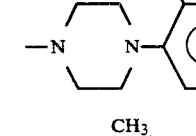 |
| H | $OCH_3$ | $OCH_3$ | H | H | H | H | H | $CH_3$ | 2 | 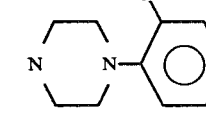 |
| H | $OCH_3$ | $OCH_3$ | H | H | H | H | H | $CH_3$ | 2 |  |
| H | $OCH_3$ | $OCH_3$ | H | H | H | H | H | $CH_3$ | 2 |  |
| H | $OCH_3$ | $OCH_3$ | H | H | H | H | H | $CH_3$ | 3 |  |

TABLE 18-continued

| $R_1'$ | $R_1''$ | $R_1'''$ | $R_1''''$ | $R_2$ | $R_3$ | $R_4$ | $R_5$ | $R_8$ | (aryl) | n | $NR_9R_{10}$ |
|---|---|---|---|---|---|---|---|---|---|---|---|
| H | $OCH_3$ | $OCH_3$ | H | H | H | H | H | $CH_3$ | — | 4 | 4-(1-methylpiperidinyl)-N'-(2-aminophenyl)urea |
| H | $OCH_3$ | $OCH_3$ | H | H | H | $CH_3$ | $CH_3$ | — | 4-F-phenyl | 2 | 4-(2-methylphenyl)piperazinyl |
| H | $OCH_3$ | $OCH_3$ | H | $CH_3$ | H | H | H | — | phenyl | 2 | 4-(2-methylphenyl)piperazinyl |
| H | $OCH_3$ | $OCH_3$ | H | $C_2H_5$ | $C_2H_5$ | H | H | — | 4-F-phenyl | 2 | 4-(2-oxo-2,3-dihydro-1H-benzimidazol-1-yl)piperazinyl |
| H | $OCH_3$ | $OCH_3$ | H | H | H | cyclopentyl | H | — | 4-F-phenyl | 2 | 6,7-dimethoxy-1,2,3,4-tetrahydroisoquinolin-2-yl |
| H | $OCH_3$ | $OCH_3$ | H | H | H | $C_3H_7$ | H | — | 4-F-phenyl |  | 6,7-dimethoxy-1,2,3,4-tetrahydroisoquinolin-2-yl |
| H | $OCH_3$ | $OCH_3$ | H | $CH_3$ | $CH_3$ | H | H | $CH_3$ | — | 3 | 1-methyl-4-(4-chlorophenyl)-4-hydroxypiperidinyl |
| H | H | H | $-OCH_3$ | $C_2H_5$ | $C_2H_5$ | H | H | H | — | 3 | 4-(4-chlorophenyl)piperazinyl |
| H | $OCH_3$ | $OCH_3$ | H | $C_3H_7$ | $C_3H_7$ | H | H | H | — | 3 | 6,7-dimethyl-1,2,3,4-tetrahydroisoquinolin-2-yl |
| H | $OC_2H_5$ | H | H | $CH_3$ | $C_2H_5$ | H | H | $CH_3$ | — | 2 | 4-(pyrimidin-2-yl)piperazinyl |

TABLE 18-continued

![Structure: benzene ring with R1', R1'', R1''', R1'''' substituents and a fused S-containing ring with R2, R3, R4, R5, R8 substituents and (CH2)nNR9R10 side chain]

| R1' | R1'' | R1''' | R1'''' | R2 | R3 | R4 | R5 | R8 | n | NR9R10 |
|---|---|---|---|---|---|---|---|---|---|---|
| OH | H | H | H | C2H5 | C3H7 | H | H | H | 3 | 4-hydroxy-4-phenylpiperidine |
| H | OCH3 | OCH3 | H | OCH3 | H | H | H | H | 2 | 3-hydroxy-3-phenylpiperidine |
| H | OCH3 | OCH3 | H | Cl | H | H | H | H | 1 | 4-phenylpiperidine |
| H | OCH3 | CF3 | H | H | H | H | H | CH3 | 3 | 6,7-dimethoxy-1,2,3,4-tetrahydroisoquinolin-2-yl |
| H | —OCH2—O— | H | H | cyclohexyl | H | H | H | H | 1 | 1-(2-oxo-2,3-dihydro-1H-benzimidazol-1-yl)piperidin-4-yl |
| H | OCH3 | OCH3 | H | CH3 | H | H | H | H | 1 | 4-(pyridin-2-yl)piperazin-1-yl |
| H | OCH3 | H | H | H | H | H | H | CH3 | 2 | NH(CH2)2-(3,4-dichlorophenyl) |
| H | —OCH2— | H | H | H | H | H | OCH3 | H | 2 | 4-(4-chlorophenyl)piperazin-1-yl |
| H | —OCH3 | OCH3 | H | H | H | OCH3 | CH3 | H | 2 | 6,7-dimethyl-1,2,3,4-tetrahydroisoquinolin-2-yl |
| H | OC2H5 | H | H | H | OCH3 | CH3 | Cl | H | 2 | 4-acetylpiperazin-1-yl |

TABLE 18-continued

[Structure: benzene ring fused with thio-containing ring, substituents R1', R1'', R1''', R1'''', R2, R3, R4, R5, R8, and (CH2)nNR9R10]

| R1' | R1'' | R1''' | R1'''' | R2 | R3 | R4 | R5 | R8 | n | NR9R10 |
|---|---|---|---|---|---|---|---|---|---|---|
| H | —CH3 | OCH3 | OCH3 | H | CH3 | Cl | H | H | 2 | N-piperidinyl-phenyl |
| H | —OCH3 | H | H | CH3 | Cl | H | H | H | 3 | N-piperidinyl(OH)(phenyl) |
| H | OCH3 | H | H | Cl | H | H | H | H | 3 | —N-piperidinyl-(4-Cl-phenyl) |
| H | OCH3 | Cl | H | CH3 | CF3 | H | H | CH3 | 2 | N-piperidinyl-phenyl |
| H | OCH3 | OCH3 | H | CH3 | H | H | H | H | 2 | —N-piperidinyl-(4-Cl-phenyl) |
| H | H | OCH3 | H | CH3 | H | CH3 | H | CH3 | 5 | —N-piperazinyl-(pyrimidinyl-OH) |
| H | —CH3 | H | H | OCH3 | H | OCH3 | H | CH3 | 5 | —N-piperazinyl-(pyrimidinyl) |
| H | H | H | OCH3 | H | H | H | phenyl | CH3 | 3 | —N-piperazinyl-N-C(=O)-furyl |
| H | —OCH3 | H | H | H | H | Br | H | H | 3 | —N-piperazinyl-N-(pyrrolyl) |
| H | OCH3 | OCH3 | H | CH3 | CH3 | H | H | H | 4 | —N-piperazinyl-N-(tetrazolyl) |

Example 27

Following the procedures similar to those used in Examples 22–23 and 25, but substituting the appropriate (isothiochroman-1-yl)alkyl halides for (isochroman-1-yl)alkyl halides, and the appropriate amines, the following compounds can be made (Table 19).

TABLE 19

| $R_1'$ | $R_1''$ | $R_1'''$ | $R_1''''$ | $R_2$ | $R_3$ | $R_4$ | $R_5$ | $R_8$ | Branch Chain | $NR_9R_{10}$ |
|---|---|---|---|---|---|---|---|---|---|---|
| H | $C_3H_7$ | $C_3H_7$ | $OCH_3$ | $CH_3$ | H | H | H | H | $-C(CH_3)_2-CH_2-$ | piperazinyl-triazine |
| H | H | H | $OCH_3$ | $CH_3$ | $CH_3$ | H | H | H | $-C(CH_3)_2-C(CH_3)_2-CH_2-$ | piperazinyl-pyridazine |
| $OCH_3$ | $OCH_3$ | H | H | H | H | $CH_3$ | $CH_3$ | H | $-C(C_2H_5)_2-CH_2-CH_2-CH_2-$ | piperazinyl-imidazole (NH) |
| H | $OC_2H_5$ | H | H | $CH_3$ | H | H | H | H | $-C(CH_3)(C_2H_5)-CH_2-C(C_2H_5)_2-CH_2-$ | 1-(4-fluorophenyl)piperazinyl |
| H | $OCH_3$ | $OCH_3$ | $OCH_3$ | $CH_3$ | $CH_3$ | H | H | H | $-C(C_2H_5)_2-CH_2-$ | piperazinyl-dihydroquinazoline |
| H | OH | $OCH_3$ | H | $CH_3$ | H | H | H | H | $-CH_2-C(C_2H_5)_2-CH_2-$ | piperazinyl-dihydroquinazoline |
| H | $OCH_3$ | Br | H | $CH_3$ | H | $CH_3$ | H | H | $-C(CH_3)_2-CH_2-CH_2-$ | 1-(2-methylphenyl)piperazinyl |
| H | $OCH_3$ | Cl | Cl | $C_2H_5$ | $C_2H_5$ | H | H | H | $-C(CH_3)_2-CH_2-C(CH_3)_2-CH_2-$ | 1-(2,6-dimethylphenyl)piperazinyl |
| H | $OCH_3$ | $CF_3$ | H | $CH_3$ | $CH_3$ | H | H | H | $-CH(C_2H_5)-C(CH_3)(H)-CH_2-$ | $NH(CH_2)_2$-(3,4-dichlorophenyl) |
| H | $-OCH_2-$ (fused) | H | cyclopentyl | H | H | H | H | - | $-C(C_2H_5)_2-CH_2-CH(C_2H_5)-CH_2-$ | 6,7-dimethyl-tetrahydroisoquinolinyl |
| H | $OCH_3$ | H | H | H | H | cyclopentyl | H | H | $-C(CH_3)_2-CH_2-C(CH_3)(C_2H_5)-CH_2-$ | 7-hydroxy-tetrahydroisoquinolinyl |
| H | $OCH_3$ | H | $OCH_3$ | $CH_3$ | $CH_3$ | H | H | H | $-C(CH_3)_2-CH_2CH_2CH_2CH_2-$ | 1-(4-fluorophenyl)piperazinyl |
| H | $OCH_3$ | $OCH_3$ | $OCH_3$ | H | H | $CH_3$ | $CH_3$ | H | $-CH(CH_3)-C(CH_3)_2-CH_2-CH_2-$ | 1-(2-methoxyphenyl)piperazinyl |

TABLE 19-continued

Structure:

$$R_1', R_1'', R_1''', R_1''''$$ on benzene ring, fused with ring containing $R_2, R_3, R_4, R_5, R_8$ and S; Branched Chain —$NR_9R_{10}$

| $R_1'$ | $R_1''$ | $R_1'''$ | $R_1''''$ | $R_2$ | $R_3$ | $R_4$ | $R_5$ | $R_8$ | Branch Chain | $NR_9R_{10}$ |
|---|---|---|---|---|---|---|---|---|---|---|
| H | H | H | OCH$_3$ | H | H | CH$_3$ | H | H | —CH$_2$—C(CH$_3$)(CH$_3$)—CH$_2$CH$_2$— | piperazinyl-pyridyl-Cl |
| H | OH | H | H | C$_2$H$_5$ | H | H | H | H | —CH(CH$_3$)—CH(C$_2$H$_5$)—CH$_2$CH— | piperidinyl-benzimidazolinone |
| H | OCH$_3$ | OCH$_3$ | H | (cyclopentyl) | | H | H | CH$_3$ | —CH(CH$_3$)—CH$_2$—CH(CH$_3$)—CH$_2$— | piperazinyl-phenyl-F |
| H | OCH$_3$ | OCH$_3$ | H | (cyclohexyl) | | H | H | CH$_3$ | —CH$_2$CH(CH$_3$) CH(CH$_3$)CH$_2$— | piperidinyl-(4-Cl-phenyl)-OH |
| H | OCH$_3$ | OCH$_3$ | H | Me | H | H | H | CH$_3$ | CH$_2$—CH(C$_2$H$_5$)—CH$_2$ | piperazinyl-phenyl-Br |
| H | OC$_3$H$_7$ | OC$_3$H$_7$ | H | H | H | Me | H | F-phenyl | —CH$_2$—CH$_2$—C(CH$_3$)(C$_2$H$_5$)—CH$_2$— | piperidinyl-(3-Cl-phenyl)-OH |

Example 28:
1-[2-{(1-methyl-6,7-dimethoxy-3,4-dihydro-1H-2-benzothiopyran-1-yl)methoxy}ethyl]piperidine.

A mixture of 2-[[1-methyl-6,7-dimethoxy-3,4-dihydro-1H-2-benzothiopyran-1-yl]methoxy]ethanol-4-nitrobenzenesulfonate and piperidine is stirred at room temperature in THF. The mixture is then partitioned between methylene chloride and aqueous sodium carbonate. The title compound is isolated by chromatography and is crystallized.

The compounds of Table 20 can be prepared using the procedures of Examples 13–18, 19, and 24 starting from the appropriate [3,4-dihydro-1H-2-benzothiopyran-1-yl]alkoxy alkanols or their benzenesulfonates, or the corresponding chlorides and the appropriate amines.

TABLE 20

Structure: benzene ring with substituents R₁', R₁'', R₁''', R₁'''', and side chain with R₂, R₃, R₄, R₅, R₈, S—(CH₂)$_m$—(OCH₂CH₂)$_q$—NR₂₁R₂₂

| R₁' | R₁'' | R₁''' | R₁'''' | R₂ | R₃ | R₄ | R₅ | R₈ | m | q | NR₂₁R₂₂ |
|---|---|---|---|---|---|---|---|---|---|---|---|
| H | H | propyl | —OCH₃ | H | H | H | H | H | 1 | 1 | NH(CH₂)₂-(3,4-dichlorophenyl) |
| H | H | H | —OCH₃ | H | H | H | H | H | 1 | 2 | 4-(4-chlorophenyl)piperazin-1-yl |
| OCH₃ | OCH₃ | H | H | H | H | H | H | H | 1 | 3 | 6,7-dimethyl-1,2,3,4-tetrahydroisoquinolin-2-yl |
| H | OC₂H₅ | H | H | H | H | H | H | H | 2 | 1 | 4-acetylpiperazin-1-yl |
| H | OCH₃ | OCH₃ | OCH₃ | H | H | H | H | H | 2 | 2 | 4-phenylpiperidin-1-yl |
| —OCH₃ | —OH | H | H | H | H | H | H | H | 2 | 3 | 4-hydroxy-4-phenylpiperidin-1-yl |
| H | —OCH₃ | Br | H | H | H | H | H | H | 3 | 1 | 2-hydroxy-2-phenylpiperidin-1-yl |
| H | —OCH₃ | Cl | Cl | H | H | H | H | H | 3 | 2 | 4-(4-fluorophenyl)piperidin-1-yl |
| H | —OCH₃ | —CF₃ | H | H | H | H | H | H | 3 | 3 | 7-chloro-1,2,3,4-tetrahydroisoquinolin-2-yl |
| H | O—CH₂—O (methylenedioxy) | | H | H | H | H | H | H | 1 | 1 | 4-(2-oxo-2,3-dihydro-1H-benzimidazol-1-yl)piperidin-1-yl |
| H | —OCH₃ | H | H | CH₃ | H | H | H | H | 2 | 1 | 4-(pyrimidin-2-yl)piperazin-1-yl |
| H | OCH₃ | H | OCH₃ | CH₃ | H | CH₃ | H | H | 3 | 2 | 4-(2-methylphenyl)piperazin-1-yl |

TABLE 20-continued

Structure:

R₁''—[benzene with R₁', R₁''', R₁'''']—[C(R₂)(R₃)—C(R₄)(R₅)]—S—[C(R₈)](CH₂)ₘ—(OCH₂CH₂)q—NR₂₁R₂₂

| R₁' | R₁'' | R₁''' | R₁'''' | R₂ | R₃ | R₄ | R₅ | R₈ | m | q | NR₂₁R₂₂ |
|---|---|---|---|---|---|---|---|---|---|---|---|
| H | OCH₃ | OCH₃ | OCH₃ | OCH₃ | H | OCH₃ | H | H | 2 | 3 | N-piperazinyl-(4-F-phenyl) |
| H | H | H | OCH₃ | H | H | H | phenyl | H | 1 | 3 | N-piperazinyl-(2-OCH₃-phenyl) |
| H | OH | H | H | H | H | F | H | H | 1 | 1 | 6,7-dimethoxy-tetrahydroisoquinolinyl |
| H | OCH₃ | OCH₃ | H | CH₃ | CH₃ | H | H | H | 2 | 2 | NH(CH₂)₂-(3,4-dichlorophenyl) |
| H | OCH₃ | OCH₃ | H | H | H | CH₃ | CH₃ | H | 3 | 3 | N-piperazinyl-(3-Br-phenyl) |
| H | OCH₃ | OCH₃ | H | cyclopentyl | | H | H | H | 3 | 1 | 6,7-dimethyl-tetrahydroisoquinolinyl |
| H | OC₃H₇ | OC₃H₇ | H | H | H | cyclobutyl | H | H | 1 | 1 | N-piperazinyl-(4-C₃H₅-phenyl) |
| H | H | OCH₃ | OCH₃ | H | H | cyclopentyl | H | H | 1 | 1 | 7-hydroxy-tetrahydroisoquinolinyl |
| H | OH | OH | H | H | H | C₃H₇ | H | H | 1 | 1 | NH(CH₂)₂-(3,4-dimethoxyphenyl) |
| H | —OCH₃ | —OCH₃ | H | H | H | CH₃ | H | CH₃ | 1 | 3 | —N(CH₃) |
| H | —OCH₃ | —OCH₃ | H | C₂H₅ | H | H | H | CH₃ | 1 | 4 | morpholino |
| H | —OCH₃ | —OCH₃ | H | cyclopentyl | | H | H | CH₃ | 1 | 4 | —N—H butyl |
| H | OCH₃ | —OCH₃ | H | cyclohexyl | | H | H | CH₃ | 2 | 3 | N-piperazinyl-(4-F-phenyl) |
| H | OCH₃ | OCH₃ | H | CH₃ | H | H | H | C₆H₅ | 1 | 3 | —NH-t-butyl |
| H | OCH₃ | OCH₃ | H | H | H | CH₃ | H | C₆H₅ | 1 | 3 | —NH₂ |

Example 29

A lot of 10,000 tablets, each containing 25 mg of 1-[2-(6,7-dimethoxy-4,4-dimethylisochroman-1-yl)ethyl]-4-(2-methyl)piperazine is prepared from the following types and amounts of ingredients:

| | |
|---|---|
| 1-[2-(6,7-dimethoxy-4,4-dimethylisochroman-1-yl)ethyl]-4-(2-methylphenyl)piperazine | 250 g |
| Dicalcium Phosphate | 1000 g |
| Methylcellulose, U.S.P. (15 cps) | 60 g |
| Talc | 150 g |
| Corn Starch | 200 g |
| Magnesium stearate | 10 g |

The compound and dicalcium phosphate are mixed well, granulated with 7.5 percent solution of methyl cellulose in water, passed through a No. 8 screen and dried carefully. The dried granules are passed through a No. 12 screen, mixed thoroughly with the talc, starch and magnesium stearate, and compressed into tablets.

These tablets are useful in treating hypertension at a dose of two tablets per day.

Example 30

A lot of 10,000 tablets, each containing 50 mg of N-[(7,8-dimethoxy-2-benzoxepin-1-yl)methyl]-(6,7-dimethoxy-1,2,3,4-tetrahydroquinoline) is prepared from the following types and amounts of ingredients

| | |
|---|---|
| N-[(7,8-dimethoxy-2-benzoxepin-1-yl)methyl]-(6,7-dimethoxy-1,2,3,4-tetrahydroquinoline) | 500 g |
| Dicalcium Phosphate | 1000 g |
| Methylcellulose, U.S.P. (15 cps) | 60 g |
| Talc | 150 g |
| Corn starch | 200 g |
| Magnesium stearate | 10 g |

The compound and dicalcium phosphate are mixed well, granulated with 7.5 percent solution of methyl cellulose in water, passed through a No. 8 screen and dried carefully. The dried granules are passed through a No. 12 screen, mixed thoroughly with the talc, starch and magnesium stearate, and compressed into tablets.

These tablets are useful in treating CNS disorders, particularly psychosis, at a dose of one tablet every eight hours.

Example 31

A sterile preparation suitable for intramuscular injection and containing 25 mg of 1-[2-(6,7-dimethoxy-4,4-dimethylisochroman-1-yl)ethyl]-4-(2-methylphenyl)-piperazine hydrochloride in each milliliter is prepared from the following types and amounts of ingredients:

| | |
|---|---|
| 1-[2-(6,7-dimethoxy-4,4-dimethylisochroman-1-yl)ethyl]-4-(2-methylphenyl)piperazine hydrochloride | 25 g |
| Benzyl benzoate | 200 ml |
| Methylparaben | 1.5 g |
| Propylparaben | 0.5 g |
| Cottonseed oil q.s. to | 1000 ml |

One milliliter of this sterile preparation is injected for treatment of hypertension two times a day.

Example 32

A sterile preparation suitable for intramuscular injection and containing 60 mg of N-[(7,8-dimethoxy-2-benzoxepin-1-yl)methyl]-(6,7-dimethoxy-1,2,3,4-tetrahydroquinoline) hydrochloride in each milliliter is prepared from the following ingredients:

| | |
|---|---|
| N-[(7,8-dimethoxy-2-benzoxepin-1-yl)methyl]-(6,7-dimethoxy-1,2,3,4-tetrahydroisoquinoline) hydrochloride | 60 g |
| Benzyl benzoate | 200 ml |
| Methylparaben | 1.5 g |
| Propylparaben | 0.5 g |
| Cottonseed oil q.s. to | 1000 ml |

One milliliter of this sterile preparation is injected for the treatment of psychosis at intervals of 8 hours.

Example 33

One thousand two-piece hard gelatin capsules for oral use, each containing 30 mg of 1-[2-(6,7-dimethoxy-4,4-dimethylisochroman-1-yl)ethyl]-4-(2-methylphenyl)piperazine are prepared from the following ingredients:

| | |
|---|---|
| 1-[2-(6,7-dimethoxy-4,4-dimethylisochroman-1-yl)ethyl]-4-(2-methylphenyl)piperazine | 30 g |
| Lactose, U.S.P. | 50 g |
| Starch, U.S.P. | 15 g |
| Talc, U.S.P. | 3.5 g |
| Calcium stearate | 1.5 g |

The micronized active ingredient is mixed with the starch-lactose mixture followed by the talc and calcium stearate. The final mixture is then encapsulated in the usual manner.

One capsule every 12 hours is administered to treat hypertension.

Example 34

One thousand two-piece hard gelatin capsules for oral use, each containing 60 mg of N-[(7,8-dimethoxy-2-benzoxepin-1-yl)methyl]-(6,7-dimethoxy-1,2,3,4-tetrahydroisoquinoline) are prepared from the following ingredients:

| | |
|---|---|
| N-[(7,8-dimethoxy-2-benzoxepin-1-yl)methyl]-(6,7-dimethoxy-1,2,3,4-tetrahydroisoquinoline) | 60 g |
| Lactose, U.S.P. | 50 g |
| Starch, U.S.P | 15 g |
| Talc, U.S.P. | 3.5 g |
| Calcium stearate | 1.5 g |

The micronized active ingredient is mixed with the starch-lactose mixture followed by the talc anc calcium stearate. The final mixture is then encapsulated in the usual manner. One capsule is used every 8 hours to treat CNS disorders, particularly psychosis.

Example 35

An aqueous preparation for oral use containing in each 5 ml (1 teaspoon) 50 mg of 1-[2-(6,7-dimethoxy-4,4-dimethylisochroman-1-yl)ethyl]-4-(2-methylphenyl)piperazine is prepared from the following ingredients:

| | |
|---|---|
| 1-[2-(6,7-dimethoxy-4,4-dimethylisochroman-1-yl)-ethyl]-4-(2-methylphenyl)piperazine hydrochloride | 55 g |
| Methylparaben, U.S.P. | 0.75 g |
| Propylparaben, U.S.P. | 0.25 g |
| Saccharin sodium | 1.25 g |
| Cyclamate sodium | 0.25 g |
| Glycerin | 300 ml |
| Tragacanth powder | 1.0 g |
| Orange oil flavor | 1.0 g |
| F.D. and C. orange dye | 0.75 g |
| Deionized water, q.s. to | 1000 ml |

A dose of one teaspoon per day is useful for treating hypertension.

Example 36

An aqueous preparation for oral use containing in each teaspoon (5 ml) 75 mg of N-[(7,8-dimethoxy-2-benzoxepin-1-yl)methyl]-(6,7-dimethoxy-1,2,3,4-tetrahydroisoquinoline) for use in treating psychotic disorders is prepared from the following ingredients:

| | |
|---|---|
| N-[(7,8-dimethoxy-2-benzoxepin-1-yl)methyl]-(6,7-dimethoxy-1,2,3,4-tetrahydroisoquinoline) hydrochloride | 85 g |
| Methylparaben, U.S.P. | 0.75 g |
| Propylparaben, U.S.P. | 0.25 g |
| Saccharin sodium | 1.25 g |
| Cyclamate sodium | 0.25 g |
| Glycerin | 300 ml |
| Tragacanth powder | 1.0 g |
| Orange oil flavor | 1.0 g |
| F.D. and C. orange dye | 0.75 g |
| Deionized water, q.s. to | 1000 ml |

A dose of one to two teaspoons per day is useful in treating CNS diseases, particularly psychosis.

I claim:

1. A method of treating psychosis in humans which comprises administering systemically to a psychotic human an antipsychotic dose of a compound selected from the group consisting of compounds having the formula:

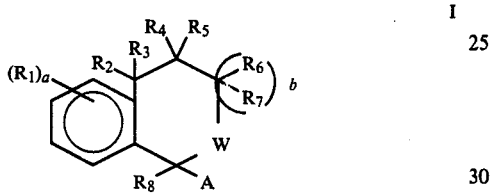

wherein
R$_1$ is the same or different and is selected from the group consisting of alkyl of one through three carbons, inclusive, alkoxy and one through three;
a is one through three;
b is zero or one;
R$_2$ through R$_7$ are the same or different and are selected from the group consisting of hydrogen, alkyl of one through three carbons, inclusive, hydroxy, alkoxy of one through three carbons; phenyl; halo; cycloalkyl of three through six carbons when R$_2$ and R$_3$, R$_4$ and R$_5$, or R$_6$ and R$_7$ are taken together with the carbon to which they are attached; cycloalkyl of four through seven carbons when R$_2$ and R$_4$ or R$_4$ and R$_6$ are taken together with the carbons to which they are attached; and cycloalkyl of five or six carbons, with the overall provisos that no more than one ring may be attached to any one carbon and that at least two of R$_2$ through R$_7$ are hydrogen.
R$_8$ is alkyl of one through three carbons, hydrogen, or phenyl unsubstituted or substituted with a maximum of three substituents selected from the group consisting of alkyl of one through three carbons, halo, alkoxy of one through three carbons, and trihaloalkyl of one to two carbons;
W is oxygen;
and A is selected from the group consisting of:
(i) —(CH$_2$)$_n$NR$_9$R$_{10}$, wherein n is one to five with the proviso that when b is zero, and n is one or two, R$_2$ through R$_5$ cannot all be hydrogen at the same time;
(ii) —(CH$_2$)$_m$—(OCH$_2$CH$_2$)$_q$—NR$_{21}$R$_{22}$, wherein m and q are each one to three, and R$_{21}$ and R$_{22}$ can be the same or different and are selected from the group consisting of H, alkyl of one through four carbons, and together with the N to which they are attached form heterocyclic rings of four to six ring atoms, morpholine, and NR$_9$R$_{10}$,

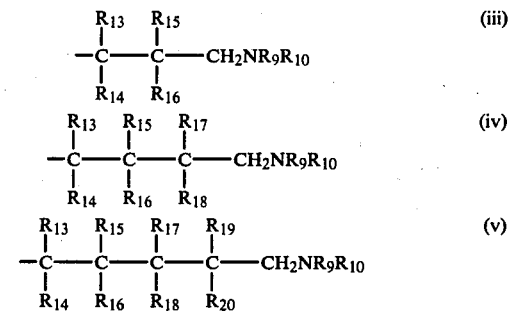

wherein NR$_9$R$_{10}$ is a heterocyclic amine selected from the group consisting of

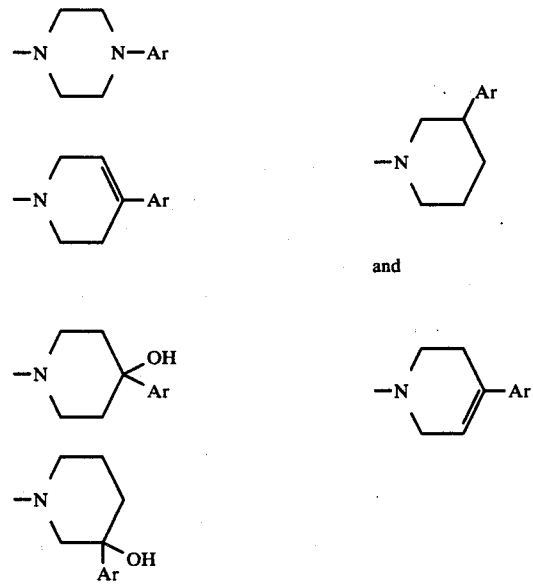

R$_{13}$ through R$_{20}$ may be the same or different and are selected from the group hydrogen and alkyl of from 1 or 2 carbon atoms, inclusive;
Ar is phenyl unsubstituted or substituted with one through three substituents selected from the group consisting of alkyl or alkoxy of one through three carbons, hydroxy, halo, and trihaloalkyl or trihaloalkoxy of one or two carbons and pharmaceutically acceptable acid addition salts thereof.

2. A method according to claim 1 wherein the compound administered is selected from the group consisting of compounds having the formula:

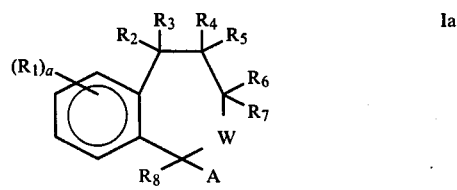

wherein $R_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one $R_1$ is hydroxy, alkoxy or o-methylenedioxy;

a is one through three;

$R_2$ through $R_7$ are the same or different and are selected from the group consisting of hydrogen, alkyl of one through three carbons, inclusive, hydroxy, alkoxy of one through three carbons; phenyl; halo; cycloalkyl of three through six carbons when $R_2$ and $R_3$, $R_4$ and $R_5$, or $R_6$ or $R_7$ are taken together with the carbon to which they are attached; cycloalkyl of four through seven carbons when $R_2$ and $R_4$ or $R_4$ and $R_6$ are taken together with the carbons to which they are attached; and cycloalkyl of five or six carbons, with the overall provisos that no more than one ring may be attached to any one carbon and that at least two of $R_2$ through $R_7$ are hydrogen $R_8$ is alkyl of one through three carbons, hydrogen, or phenyl unsubstituted or substituted with a maximum of three substituents selected from the group consisting of alkyl of one through three carbons, halo, alkoxy of one through three carbons, and trihaloalkyl of one to two carbons;

W is oxygen;

and A is selected from the group consisting of:

(i) —$(CH_2)_nNR_9R_{10}$, wherein n is one to five with the proviso that when b is zero, and n is one or two, $R_2$ through $R_5$ cannot all be hydrogen at the same time;

(ii) —$(CH_2)_m$—$(OCH_2CH_2)_q$—$NR_{21}R_{22}$, wherein m and q are each one to three, and $R_{21}$ and $R_{22}$ can be the same or different and are selected from the group consisting of H, alkyl of one through four carbons, and together with the N to which they are attached form heterocyclic rings of four to six ring atoms, morpholine, and $NR_9R_{10}$,

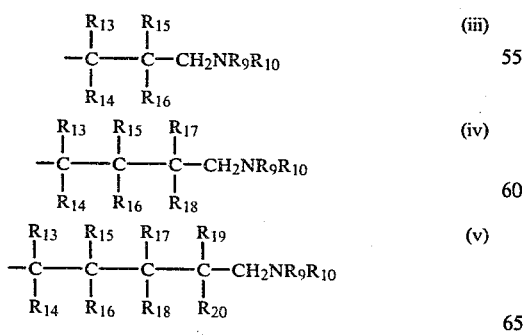

wherein $NR_9R_{10}$ is a heterocyclic amine selected from the group consisting of

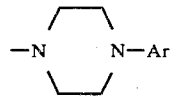

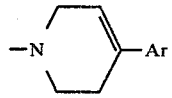

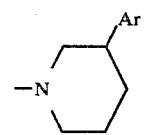

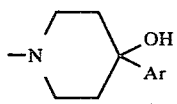

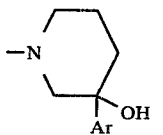

and $R_{13}$ through $R_{20}$ may be the same or different and are selected from the group hydrogen and alkyl of from 1 or 2 carbon atoms, inclusive;

Ar is phenyl unsubstituted or substituted with one through three substituents selected from the group consisting of alkyl or alkoxy of one through three carbons, hydroxy, halo, and trihaloalkyl or trihaloalkoxy of one or two carbons and pharmaceutically acceptable acid addition salts thereof.

3. A method of treating psychosis in humans which comprises administering systemically to a psychotic human an antipsychotic dose of a compound selected from the group consisting of compounds having the formula

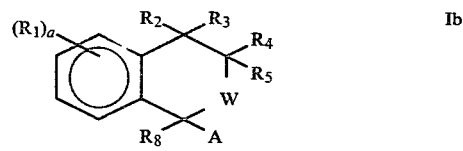

wherein $R_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one $R_1$ is hydroxy, alkoxy or o-methylenedioxy;

a is one through three;

$R_2$ through $R_5$ are the same or different and are selected from the group consisting of hydrogen, alkyl of one through three carbons, inclusive, hydroxy, alkoxy of one through three carbons; phenyl; halo; cycloalkyl of three through six carbons when $R_2$ and $R_3$, $R_4$ and $R_5$, or $R_6$ and $R_7$ are taken together with the carbon to which they are attached; cycloalkyl of four through seven carbons when $R_2$ and $R_4$ or $R_4$ and $R_6$ are taken together with the carbons to which they are attached; and cycloalkyl of five or six carbons, with the overall provisos that no more than one ring may be attached to any one carbon and that at least two of $R_2$ through $R_7$ are hydrogen.

$R_8$ is alkyl of one through three carbon, hydrogen, or phenyl unsubstituted or substituted with a maximum of three substituents selected from the group consisting of alkyl of one through three carbons, halo, alkoxy of one through three carbons, and trihaloalkyl of one to two carbons;

W is oxygen;

and A is selected from the group consisting of:

(i) —$(CH_2)_n NR_9 R_{10}$, wherein n is one to five with the proviso that when b is zero, and n is one or two, $R_2$ through $R_5$ cannot all be hydrogen at the same time;

(ii) —$(CH_2)_m$—$(OCH_2CH_2)_q$—$NR_{21}R_{22}$, wherein m and q are each one to three, and $R_{21}$ and $R_{22}$ can be the same or different and are selected from the group consisting of H, alkyl of one through four carbons, and together with the N to which they are attached form heterocyclic rings of four to six ring atoms, morpholine, and $NR_9R_{10}$,

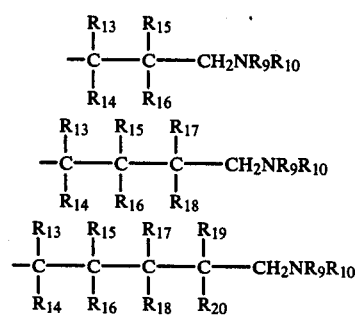

wherein $NR_9R_{10}$ is a heterocyclic amine selected from the group consisting of

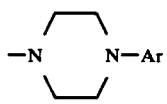

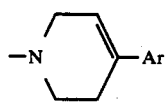

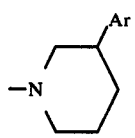

and

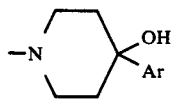

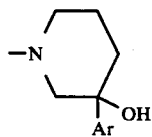

$R_{13}$ through $R_{20}$ may be the same or different and are selected from the group hydrogen and alkyl of from 1 to 2 carbon atoms, inclusive;

Ar is phenyl unsubstituted or substituted with one through three substituents selected from the group, consisting of alkyl or alkoxy of one through three carbons, hydroxy, halo, and trihaloalkyl or trihaloalkoxy of one or two carbons and pharmaceutically acceptable acid addition salts thereof.

4. A method according to claim 2 when A is the group —$(CH_2)_n NR_9 R_{10}$.

5. A method according to claim 3 when A is the group —$(CH_2)_n NR_9 R_{10}$.

6. A method according to claim 2 wherein W is oxygen and A is the group —$(CH_2)_m$—$(OCH_2CH_2)_q NR_9R_{10}$.

7. A method according to claim 3 wherein W is oxygen and A is the group —$(CH_2)_m$—$(OCH_2CH_2)_q NR_9R_{10}$.

8. A method according to claim 4 wherein W is oxygen, $R_1$ through $R_7$ are the same or different and are selected from the group consisting of hydrogen, alkyl of one through three carbon atoms, inclusive and cycloalkyl of four through seven carbon atoms, inclusive, when $R_2$ and $R_4$ or $R_4$ and $R_6$ are taken together with the carbon atom to which they are attached.

9. A method according to claim 5 wherein a is two or three, $R_2$ through $R_5$ are the same or different and are selected from the group consisting of hydrogen, alkyl of one through three carbon atoms, inclusive, and cycloalkyl of four through seven carbon atoms, inclusive, when $R_2$ and $R_4$ are taken together with the carbon atom to which they are attached, with the proviso that when $R_3$ through $R_5$ are hydrogen, $R_2$ cannot be hydrogen.

10. A method according to claim 8 wherein $R_2$ through $R_7$ are the same or different and are selected from the group cnsisting of hydrogen alkyl of one to three carbon atoms, inclusive, and cycloalkyl of four through seven carbon atoms, inclusive, when $R_2$ and $R_4$ are taken together with the carbon atom to which they are attached.

11. A method according to claim 9 wherein $NR_9R_{10}$ is selected from the group consisting of

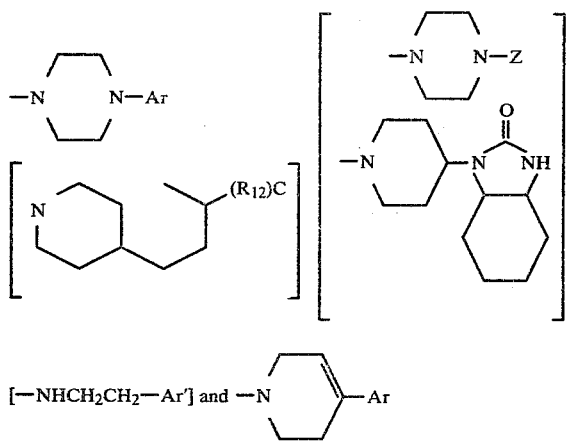

Ar is phenyl unsubstituted or substituted with one through three substituents selected from the group consisting of alkyl or alkoxy of one through three carbons, hydroxy, halo, and trihaloalkyl or trihaloalkoxy of one or two carbons.

12. A method according to claim 9 wherein $(R_1)a$ is dilower alkoxy of from one to four carbon atoms, inclusive; $R_2$ and $R_3$ are both lower alkyl of from one to four carbon atoms, inclusive; and $R_4$ and $R_5$ are both hydrogen.

13. A method according to claim 12 wherein the compound administered is selected from the group consisting of 4-(4-chloro-1-[(3,4-dihydro-6,7-dimethoxy-4,4-dimethyl-1H-2-benzopyran-1-yl)methyl]-1,2,3,6-tetrahydropyridine and the monohydrochloride acid addition salt thereof.

14. A method according to claim 12 wherein the compound administered is selected from the group consisting of
1-[2-(6,7-dimethoxy-4,4-dimethyl-isochroman-1-yl)ethyl]-4-[2-pyridyl]piperazine,
1-[2-(6,7-dimethoxy-4,4-dimethyl-isochroman-1-yl)ethyl]-4-(4-chlorophenyl)piperazine,
1-[2-(6,7-dimethoxy-4,4-dimethyl-isochroman-1-yl)ethyl]-4-(2-methylphenyl)piperazine,
4-phenyl-1-[2-(6,7-dimethoxy-4,4-dimethyl-isochroman-1-yl)ethyl]-1,2,3,6-tetrahydropyridine,
1-[2-(6,7-dimethoxy-4,4-dimethyl-isochroman-1-yl)ethyl]-4-(4-fluorophenyl)piperazine,
1-[3-(3,4-dihydro-6,7-dimethoxy-1-methyl-1H-2-benzopyran-1-yl)propyl]-4-(2-methyl)phenylpiperazine and the monohydrochloride salt thereof,
4-phenyl-1-[2-(3,4-dihydro-4,4-dimethyl-6,7-dimethoxy-1H-2-benzopyran-1-yl)ethyl]piperazine, dihydrate,
4-(2-pyridyl)-1-[3-(3,4-dihydro-1-methyl-6,7-dimethoxy-1H-2-benzopyran-1-yl)propyl]piperidine
4-(4-fluorophenyl)-1-[3-(3,4-dihydro-1-(4-fluorophenyl)-6,7-dimethoxy-1H-2-benzopyran-1-yl)propyl]piperazine,
4-(4-fluorophenyl)-1-[3-(3,4-dihydro-1-(4-fluorophenyl)-6,7-dimethoxy-1H-2-benzopyran-1-yl)propyl]piperazine, trihydrate hydrochloride,
4-(2-methylphenyl)-1-[3-(3,4-dihydro-1-(4-fluorophenyl)-6,7-dimethoxy-1H-2-benzopyran-1-yl)propyl]piperazine,
4-(2-methylphenyl)-1-[3-(3,4-dihydro-1-(4-fluorophenyl)-6,7-dimethoxy-1H-2-benzopyran-1-yl)propyl]piperazine, hydrochloride salt hydrate.
4-(phenyl)-1-[3-(3,4-dihydro-1-(4-fluorophenyl)-6,7-dimethoxy-1H-2-benzopyran-1-yl)propyl]-1,2,3,6-tetrahydropyridine.
1-[3-(3,4-dihydro-1-(4-fluorophenyl)-6,7-dimethoxy-1H-2-benzopyran-1-yl)propyl]-4-phenylpiperazine,
1-[3-(3,4-dihydro-1-(4-fluorophenyl)-6,7-dimethoxy-1H-2-benzopyran-1-yl)propyl]-4-phenylpiperazine.

15. A method according to claim 3 wherein a is two or three.

16. A method according to claim 15 wherein the compound administered is
1-[3-(3,4-dihydro-6,7-dimethoxy-1-methyl-1H-2-benzopyran-1-yl)propyl]-2-methyl-4-phenyl-piperazine, monohydrochloride.

* * * * *